United States Patent [19]
Valley et al.

[11] Patent Number: 5,814,016
[45] Date of Patent: Sep. 29, 1998

[54] ENDOVASCULAR SYSTEM FOR ARRESTING THE HEART

[75] Inventors: Kirsten L. Valley, Mountain View; David W. Snow, Woodside; Timothy C. Corvi, Belmont; Brian S. Donlon, Los Altos Hills; Stephen W. Boyd, Redwood City; Sylvia W. Fan, San Francisco; Alex T. Roth, Redwood City; William S. Peters, Woodside; Richard J. Mueller, Jr., Byron; Hanson S. Gifford, III, Woodside, all of Calif.

[73] Assignee: Heartport, Inc., Redwood City, Calif.

[21] Appl. No.: 797,229

[22] Filed: Feb. 7, 1997

Related U.S. Application Data

[62] Division of Ser. No. 486,216, Jun. 7, 1995, which is a continuation of Ser. No. 282,192, Jul. 28, 1994, Pat. No. 5,584,803, which is a continuation of Ser. No. 162,742, Dec. 3, 1993, abandoned, which is a continuation of Ser. No. 123,411, Sep. 17, 1993, abandoned, which is a continuation of Ser. No. 991,188, Dec. 15, 1992, abandoned, which is a continuation of Ser. No. 730,559, Jul. 16, 1991, Pat. No. 5,370,685, and a continuation-in-part of Ser. No. 159,815, Nov. 30, 1993, Pat. No. 5,433,700, and a continuation-in-part of Ser. No. 281,962, Jul. 28, 1994, abandoned, which is a continuation-in-part of Ser. No. 163,241, Dec. 6, 1993, Pat. No. 5,571,215, which is a continuation-in-part of Ser. No. 23,778, Feb. 22, 1993, Pat. No. 5,452,733, and a continuation-in-part of Ser. No. 281,981, Feb. 28, 1994, which is a continuation-in-part of Ser. No. 23,778, Feb. 22, 1993, Pat. No. 5,452,733, and a continuation-in-part of Ser. No. 213,760, Mar. 16, 1994, Pat. No. 5,458,574.

[51] Int. Cl.[6] .................................................. A61M 29/00
[52] U.S. Cl. .................................................. 604/96; 604/4
[58] Field of Search .............................. 604/96, 101, 102, 604/4; 606/192, 194; 600/16–18

[56] References Cited

U.S. PATENT DOCUMENTS 3,671,979 6/1972 Moulopoulos .

(List continued on next page.)

FOREIGN PATENT DOCUMENTS 218275 4/1987 European Pat. Off. .
0 350 302 7/1989 European Pat. Off. .

(List continued on next page.)

OTHER PUBLICATIONS

Bourassa, Cardiovascular Catheters Sterile, USCI, 4 pages.

(List continued on next page.)

Primary Examiner—Corrine M. McDermott
Attorney, Agent, or Firm—Jeffry J. Grainger; Jens E. Hoekendijk

[57] ABSTRACT

Devices and methods are provided for temporarily inducing cardioplegic arrest in the heart of a patient and for establishing cardiopulmonary bypass in order to facilitate surgical procedures on the heart and its related blood vessels. Specifically, a catheter based system is provided for isolating the heart and coronary blood vessels of a patient from the remainder of the arterial system and for infusing a cardioplegic agent into the patient's coronary arteries to induce cardioplegic arrest in the heart. The system includes an endoaortic partitioning catheter having an expandable balloon at its distal end which is expanded within the ascending aorta to occlude the aortic lumen between the coronary ostia and the brachiocephalic artery. Means for centering the catheter tip within the ascending aorta include specially curved shaft configurations, eccentric or shaped occlusion balloons and a steerable catheter tip, which may be used separately or in combination. The shaft of the catheter may have a coaxial or multilumen construction. The catheter may further include piezoelectric pressure transducers at the distal tip of the catheter and within the occlusion balloon. Means to facilitate nonfluoroscopic placement of the catheter include fiberoptic transillumination of the aorta and a secondary balloon at the distal tip of the catheter for atraumatically contacting the aortic valve. The system further includes a dual purpose arterial bypass cannula and introducer sheath for introducing the catheter into a peripheral artery of the patient.

4 Claims, 32 Drawing Sheets

U.S. PATENT DOCUMENTS

| | | | |
|---|---|---|---|
| 3,769,960 | 11/1973 | Robinson . | |
| 3,788,328 | 1/1974 | Alley et al. . | |
| 3,903,895 | 9/1975 | Alley et al. . | |
| 4,000,739 | 1/1977 | Stevens . | |
| 4,056,854 | 11/1977 | Boretos et al. . | |
| 4,122,858 | 10/1978 | Schiff . | |
| 4,173,981 | 11/1979 | Mortensen et al. . | |
| 4,276,874 | 7/1981 | Wolvek et al. . | |
| 4,285,341 | 8/1981 | Pollack . | |
| 4,287,892 | 9/1981 | Schiff . | |
| 4,327,709 | 5/1982 | Hanson et al. . | |
| 4,527,549 | 7/1985 | Gabbay . | |
| 4,531,936 | 7/1985 | Gordon . | |
| 4,540,399 | 9/1985 | Litzie et al. . | |
| 4,592,340 | 6/1986 | Boyles . | |
| 4,601,713 | 7/1986 | Fuqua . | |
| 4,664,125 | 5/1987 | Pinto . | |
| 4,697,574 | 10/1987 | Karcher et al. . | |
| 4,705,507 | 11/1987 | Boyles . | |
| 4,741,328 | 5/1988 | Gabbay . | |
| 4,770,652 | 9/1988 | Mahurkar . | |
| 4,771,777 | 9/1988 | Horzewski et al. . | |
| 4,785,795 | 11/1988 | Singh . | |
| 4,790,825 | 12/1988 | Berstein et al. . | |
| 4,804,365 | 2/1989 | Litzie et al. . | |
| 4,877,035 | 10/1989 | Bogen et al. . | |
| 4,889,137 | 12/1989 | Kolobow . | |
| 4,902,272 | 2/1990 | Milder et al. . | |
| 4,902,273 | 2/1990 | Choy et al. . | |
| 4,921,478 | 5/1990 | Solano et al. . | |
| 4,943,275 | 7/1990 | Stricker . | |
| 4,944,729 | 7/1990 | Buckberg et al. . | |
| 5,009,636 | 4/1991 | Wortley et al. . | |
| 5,011,469 | 4/1991 | Buckberg et al. . | |
| 5,013,296 | 5/1991 | Buckberg et al. . | |
| 5,024,668 | 6/1991 | Peters et al. . | |
| 5,041,098 | 8/1991 | Loiterman et al. . | |
| 5,069,661 | 12/1991 | Trudell . | |
| 5,071,406 | 12/1991 | Jang | 604/96 |
| 5,104,377 | 4/1992 | Levine . | |
| 5,106,368 | 4/1992 | Uldall et al. . | |
| 5,116,305 | 5/1992 | Milder et al. . | |
| 5,120,323 | 6/1992 | Shockey et al. . | |
| 5,163,905 | 11/1992 | Don Michael . | |
| 5,167,628 | 12/1992 | Boyles . | |
| 5,171,218 | 12/1992 | Fonger et al. . | |
| 5,171,232 | 12/1992 | Castillo et al. . | |
| 5,176,619 | 1/1993 | Segalowitz . | |
| 5,186,713 | 2/1993 | Riable . | |
| 5,195,942 | 3/1993 | Weil et al. . | |
| 5,219,326 | 6/1993 | Hattler . | |
| 5,224,923 | 7/1993 | Bromander . | |
| 5,224,933 | 7/1993 | Bromander . | |
| 5,226,427 | 7/1993 | Buckberg et al. . | |
| 5,250,038 | 10/1993 | Melker et al. . | |
| 5,254,097 | 10/1993 | Schock et al. . | |
| 5,270,005 | 12/1993 | Raible . | |
| 5,304,132 | 4/1994 | Jang . | |
| 5,308,320 | 5/1994 | Safar et al. . | |
| 5,312,343 | 5/1994 | Krog et al. . | |
| 5,312,344 | 5/1994 | Grinfeld et al. . | |
| 5,312,355 | 5/1994 | Lee . | |
| 5,322,509 | 6/1994 | Rickerd . | |
| 5,328,468 | 7/1994 | Kaneko et al. . | |
| 5,330,433 | 7/1994 | Fonger et al. . | |
| 5,334,142 | 8/1994 | Paradis . | |
| 5,338,314 | 8/1994 | Ryan . | |
| 5,370,640 | 12/1994 | Kolff . | |
| 5,374,245 | 12/1994 | Mahurkar . | |
| 5,395,330 | 3/1995 | Marcadis et al. | 604/96 |
| 5,395,332 | 3/1995 | Ressemann et al. . | |
| 5,395,352 | 3/1995 | Penny . | |
| 5,411,027 | 5/1995 | Wiklund et al. . | |
| 5,417,657 | 5/1995 | Hauer . | |
| 5,421,825 | 6/1995 | Farcot . | |
| 5,423,763 | 6/1995 | Helland . | |
| 5,433,700 | 7/1995 | Peters . | |
| 5,451,207 | 9/1995 | Yock . | |
| 5,453,076 | 9/1995 | Kiyota et al. | 600/18 |
| 5,478,309 | 12/1995 | Sweezer et al. | 604/4 |
| 5,487,730 | 1/1996 | Marcadis et al. . | |
| 5,505,698 | 4/1996 | Booth et al. . | |
| 5,525,388 | 6/1996 | Wand et al. . | |
| 5,527,292 | 6/1996 | Adams et al. . | |
| 5,569,199 | 10/1996 | Solar . | |

FOREIGN PATENT DOCUMENTS

| Number | Date | Source |
|---|---|---|
| 0 414 350 A1 | 6/1990 | European Pat. Off. . |
| WO 91/01689 | 2/1991 | WIPO . |
| WO 91/08791 | 6/1991 | WIPO . |
| 91/17720 | 11/1991 | WIPO . |
| 92/17118 | 10/1992 | WIPO . |

OTHER PUBLICATIONS

Buckberg, G.D. "Strategies and logic of cardioplegic delivery to prevent, avoid, and reverse ischemic and reperfusion damage" *J Thorac Cardio Vasc Surg*, 93:127–129 (1987).

Yamaguchi, A., "A case of reoperation using a balloon catheter with blocked pars ascendes aortae" *Kyobu Geka*, 42(11):961–964 (1991).

Peters, W.S. "The promise of cardioscopic surgery" *AustralAs J Cardiac Thorac Surg* 2(3):152–154 (1993).

Rossi, F., "Long–term cardiopulmonary bypass by peripheral cannulation in a model of total heart failure" *J Thorac Cardio Vasc Surg* 100:914–921 (1990).

Razi, D.M., "The challenge of calcific aortitis" *J Cardiac Thorac Surg*, 8:102–107 (1993).

Ogawa, K., "Aortic arch reconstruction without aortic cross–clamping using separate extracorporeal circulation" *J Jpn Assn Thorac Surg*, pp. 2185–2190 (1993).

Gundry et al. "A comparison of retrograde of cardioplegia versus antegrade cardioplegia in the presence of coronary artery obstruction" *Ann Thorac Surg* 38(2):124–127 (1984).

Lust et al. "Improved protection of chronically inflow–limited myocardium with retrograde coronary sinus cardioplegia" *Circulation III*, 78(5):217–223 (1988).

Crooke et al. "Biventricular distribution of cold blood cardioplegic solution administered by different retrograde techniques" *J Cardiac Thorac Surg.* 102(4):631–636 (1991).

Sabiston, D.C. Textbook of Surgery, 10th Ed. 1972, pp. 2021–2023, 2114–2121.

Ishizaka "Myocardial protection by retrograde cardiac perfusion with cold modified Krebs solution through coronary sinus during complete ischemic arrest for 120 min." *J Jpn Assn Thorac Surg*, 25(12):1592–1601 (1977).

Takahashi, M. "Retrograde coronary sinus perfusion for myocardial protection in aortic valve surgery" *J Jpn Assn Thorac Surg* 30(3):306–318 (1982).

Uchida et al., "Percutaneous cardiomyotomy and valvulotomy with angioscopic guidance" *American Heart Journal* 121(4, part 1):1221–1224 (1991).

Andersen et al., "Transluminal implantation of artificial heart valves. . . " *European Heart Journal*, 13:704–708 (1992).

Uchida et al., "Percutaneous fiberoptic angioscopy of the cardiac valves" *Am Heart J* 121(6, part 1):1791–98 (1991).

"Occlusion Balloon Catheters: Instructions for Use" *Medio-Tech, Boston Scientific Corporation,* Rev. Mar. 1991.

Cosgrove, D.M. "Management of the calcified aorta: An alternative method of occlusion" *Ann Thorac Surg.* 36:718–719 (1983).

Foster and Threlkel "Proximal Control of Aorta with a Balloon Catheter" *Surg, Gynecology & Obstetrics* pp. 693–694 (1971).

Erath and Stoney "Balloon catheter occlusion of the ascending arota" *Ann Thorac Surg.* 35:560–561 (1983).

Sakaguchi et al. "Aortic valve replacement and coronary artery bypass" *J. Jap Assoc for Thoracic Surg* 41(6):1063–1068 (1993).

Okita et al., "Utilization of Triple–Lumen Balloon Catheter for Occlusion of the Ascending Aorta During Distal Aortic Arch Surgery with Hypothermic Retorgrade Cerebral Circulation Technique Through Left Thoracotomy," 1995; 10:699–702.

Bourassa Cardiovascular Catheters Sterile USCI Catalog Rev. 6–72/5070017.

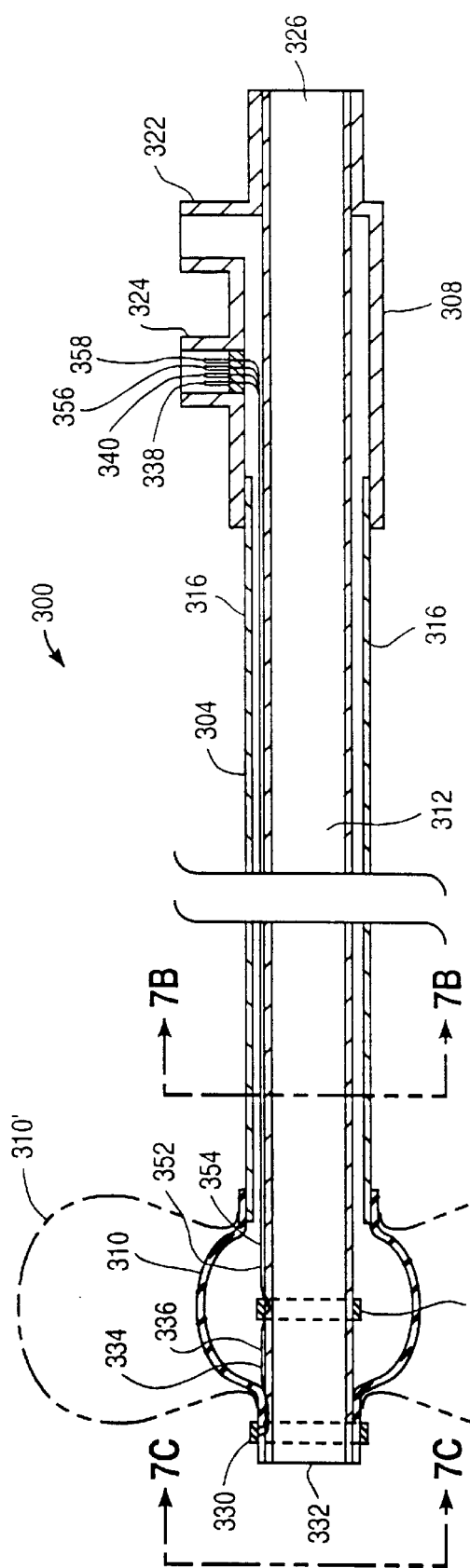
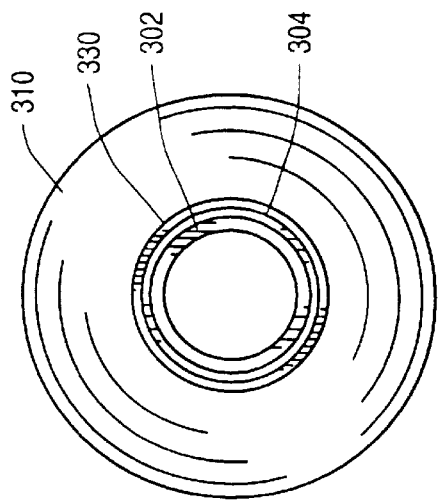
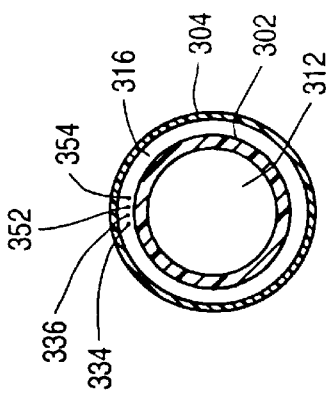
FIG. 7A
FIG. 7B
FIG. 7C

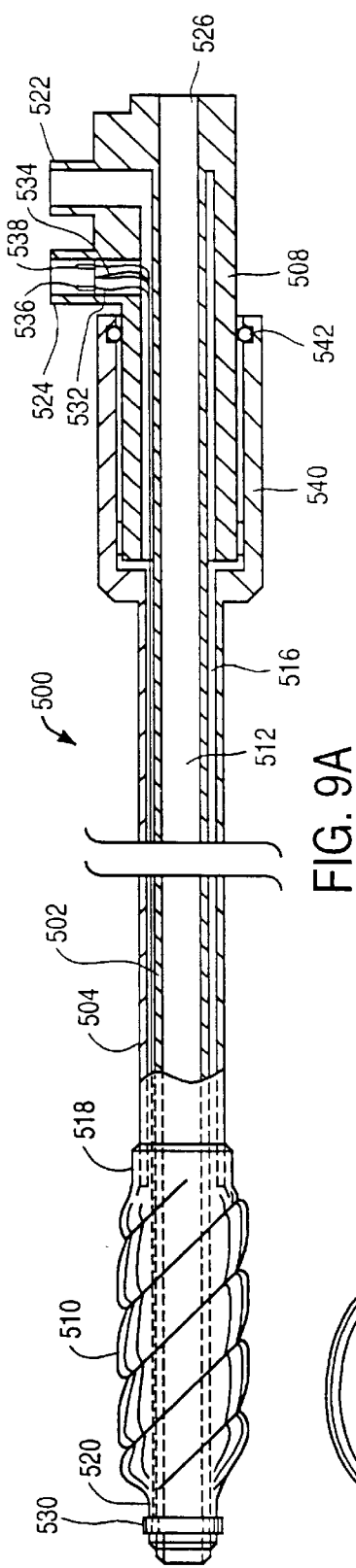
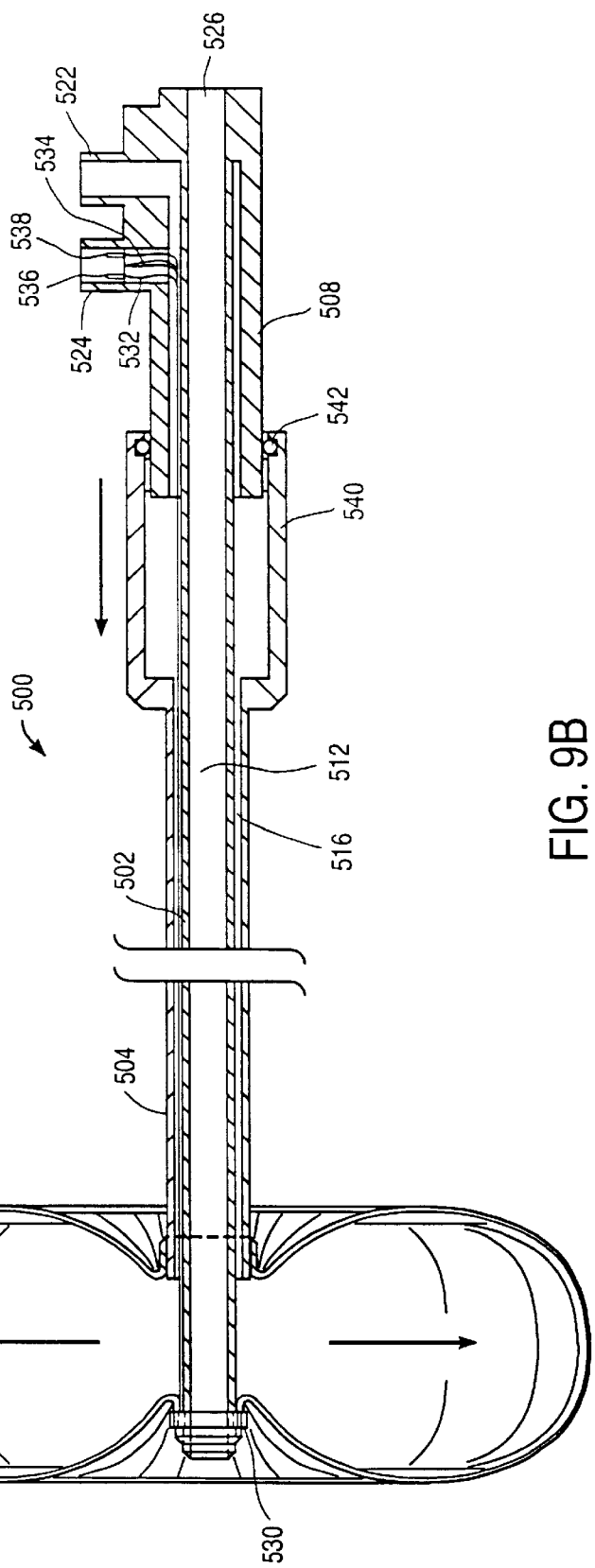
FIG. 9A
FIG. 9B

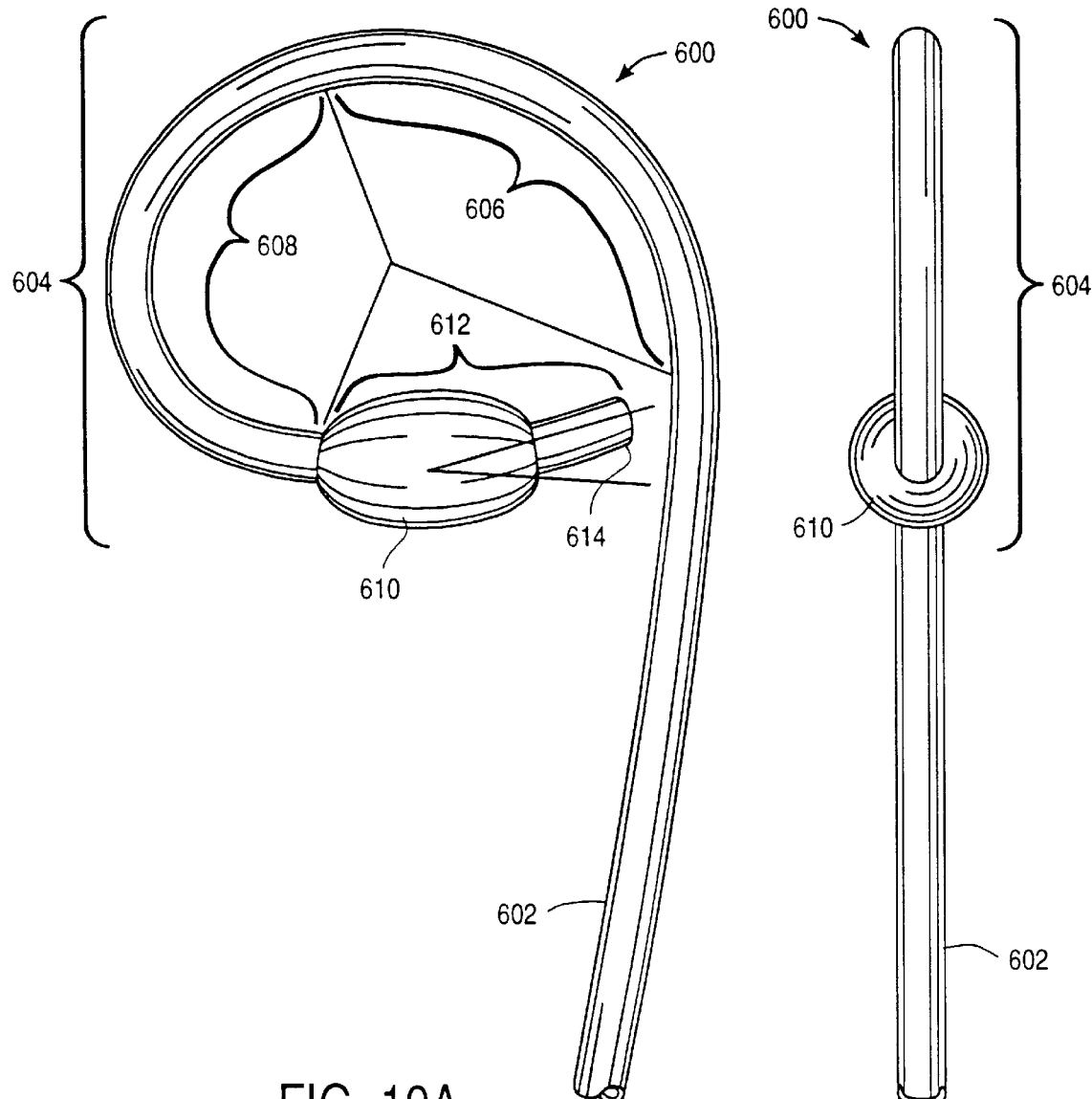
FIG. 10A
FIG. 10B
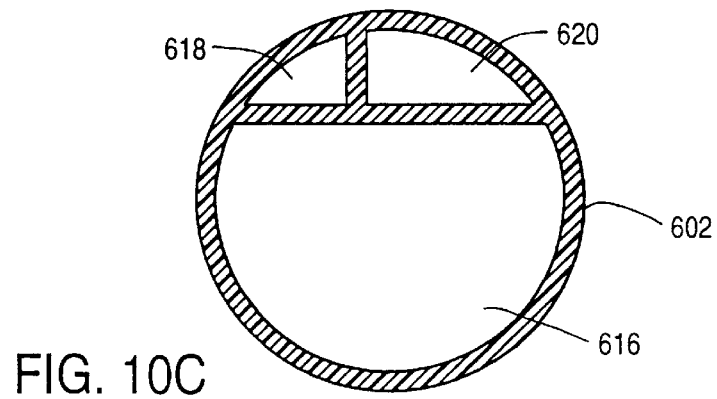
FIG. 10C

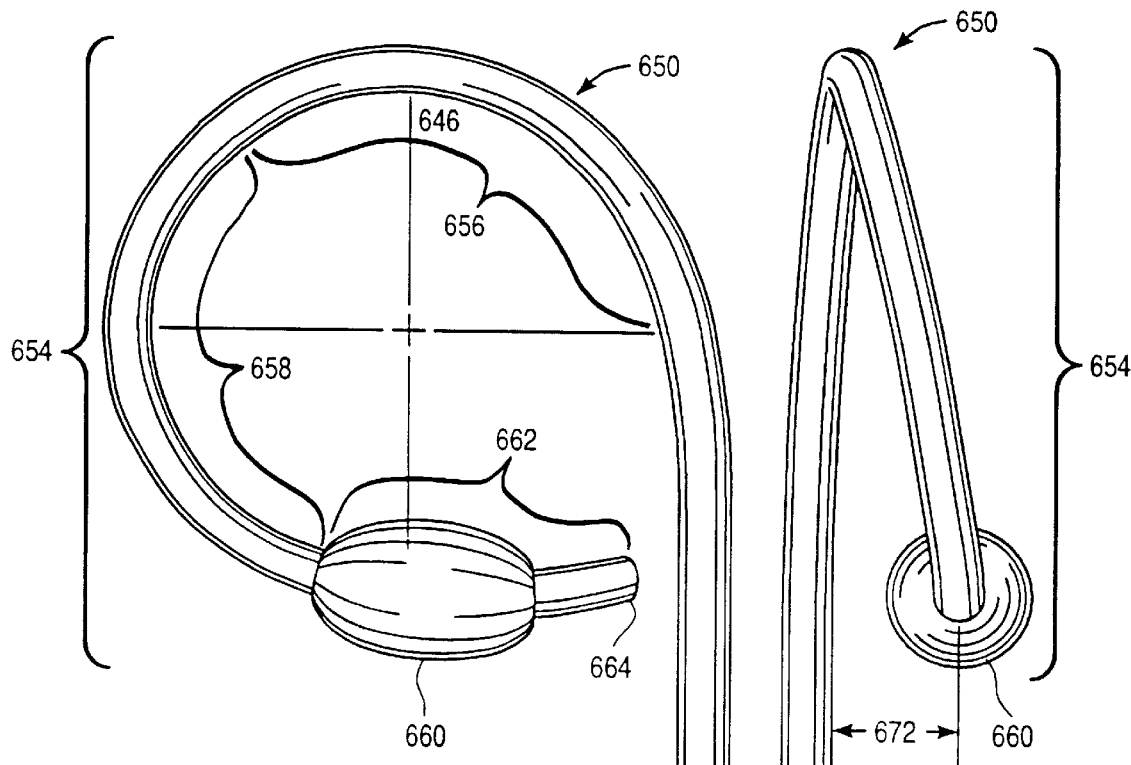
FIG. 12A
FIG. 12B
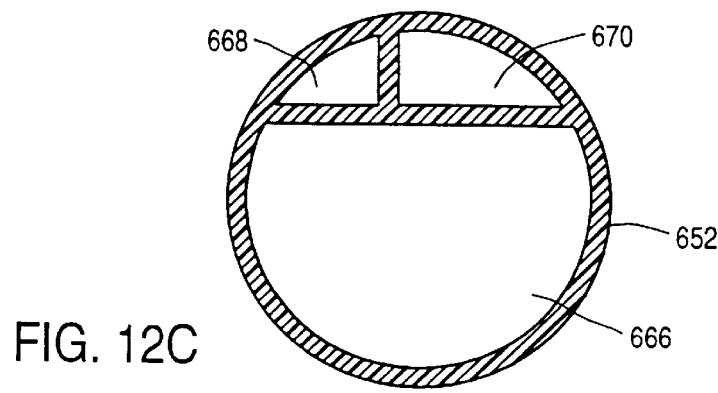
FIG. 12C

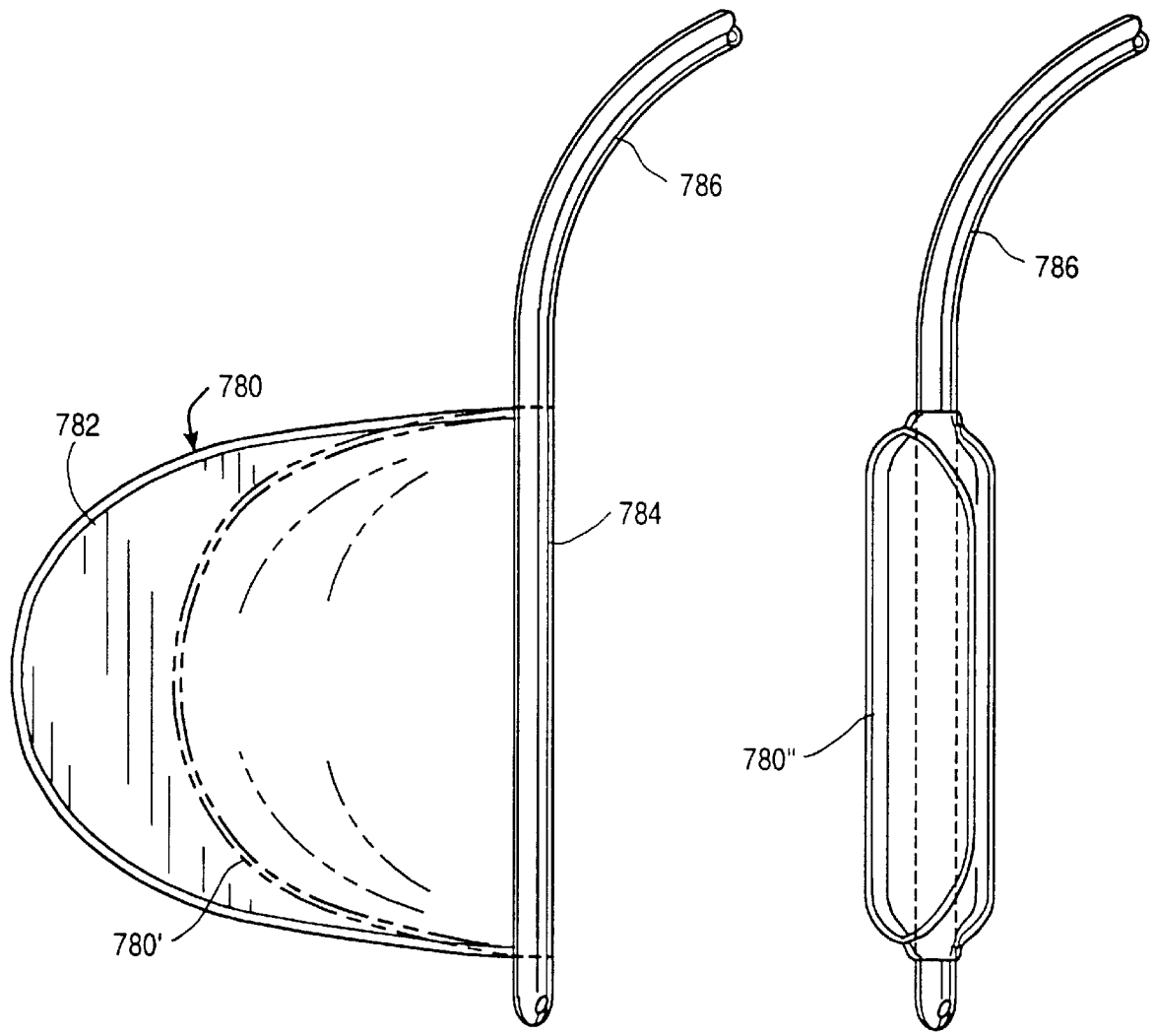
FIG. 20A
FIG. 20C
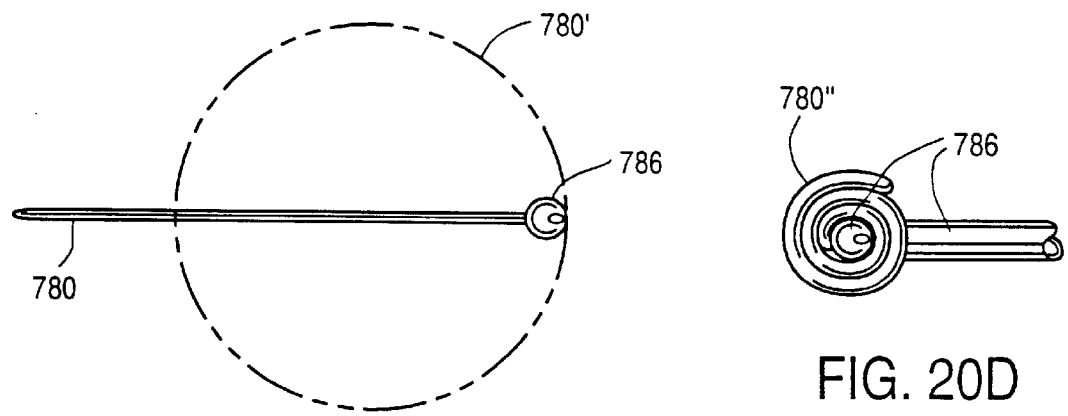
FIG. 20B
FIG. 20D

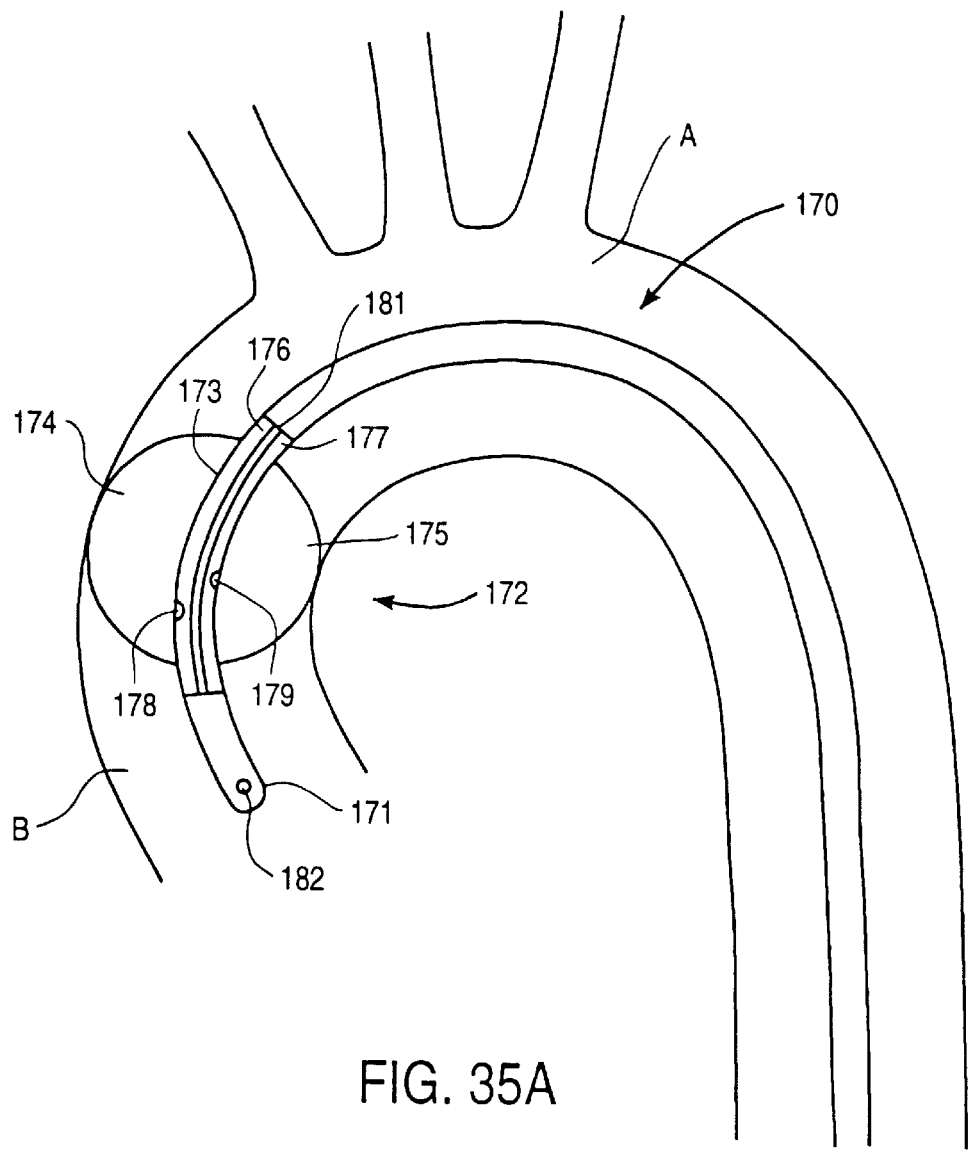
FIG. 35A
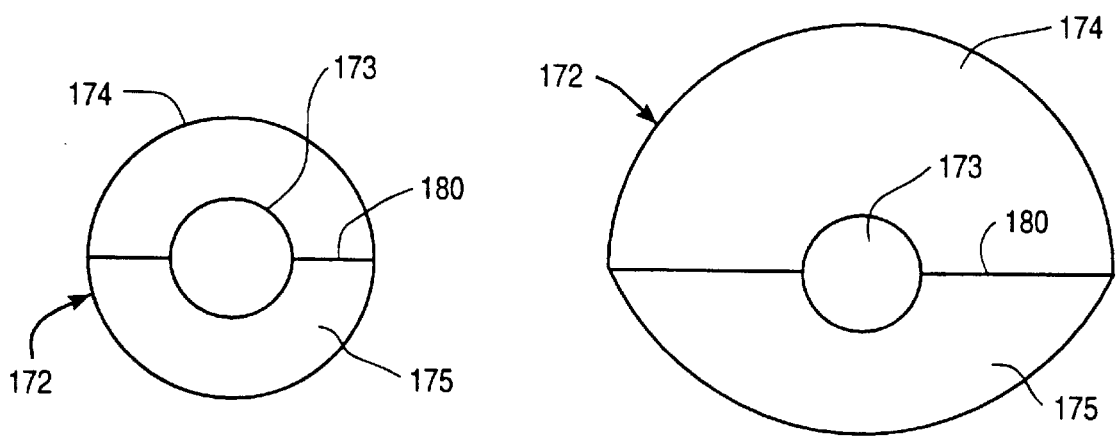
FIG. 35B
FIG. 35C

ENDOVASCULAR SYSTEM FOR ARRESTING THE HEART

CROSS REFERENCE TO RELATED APPLICATIONS

This is a Division of application Ser. No. 08/486,216 filed Jun. 7, 1995, which is a continuation-in-part of application of U.S. patent application Ser. No. 08/282,192, filed Jul. 28, 1994 now U.S. Pat. No. 5,584,803, which is a continuation-in-part of application Ser. No. 08/162,742, filed Dec. 3, 1993 now abandoned, which is a continuation-in-part of application Ser. No. 08/123,411, filed Sep. 17, 1993 now abandoned, which is a continuation-in-part of application Ser. No. 07/991,188, filed Dec. 15, 1992 now abandoned, which is a continuation-in-part of application Ser. No. 07/730,559, filed Jul. 16, 1991, which issued as U.S. Pat. No. 5,370,685 on Dec. 6, 1994. This application is also a continuation-in-part of copending U.S. patent application Ser. No. 08/159,815, filed Nov. 30, 1993, now U.S. Pat. No. 5,433,700, which is a U.S. counterpart of Australian Patent Application No. PL 6170, filed Dec. 3, 1992. This application is also a continuation-in-part of U.S. patent application Ser. No. 08/281,962, filed Jul. 28, 1994 now abandoned, which is a continuation-in-part of application Ser. No. 08/163,241, filed Dec. 6, 1993 now U.S. Pat. No. 5,571,215, which is a continuation-in-part of application Ser. No. 08/023,778, filed Feb. 22, 1993 now U.S. Pat. No. 5,452,733. This application is also a continuation-in-part of copending U.S. patent application Ser. No. 08/281,981, filed Jul. 28, 1994, which is a continuation-in-part of application Ser. No. 08/023,778, filed Feb. 22, 1993 now U.S. Pat. No. 5,452,733. This application is also a continuation-in-part of U.S. patent application Ser. No. 08/213,760, filed Mar. 16, 1994 now U.S. Pat. No. 5,458,574. The complete disclosures of all of the forementioned related U.S. patent applications are hereby incorporated herein by reference for all purposes.

FIELD OF THE INVENTION

The present invention relates generally to devices and methods for temporarily inducing cardioplegic arrest in the heart of a patient and for establishing cardiopulmonary bypass in order to facilitate surgical procedures on the heart and its related blood vessels. More particularly, it relates to a catheter based system for isolating the heart and coronary blood vessels of a patient from the remainder of the arterial system and for infusing a cardioplegic agent into the patient's coronary arteries to induce cardioplegic arrest in the heart.

BACKGROUND OF THE INVENTION

Various cardiovascular, neurosurgical, pulmonary and other interventional procedures, including repair or replacement of aortic, mitral and other heart valves, repair of septal defects, congenital defect repairs, pulmonary thrombectomy, coronary artery bypass grafting, angioplasty, atherectomy, treatment of aneurysms, electrophysiological mapping and ablation, and neurovascular procedures, may require general anesthesia, cardiopulmonary bypass, and arrest of cardiac function. In such procedures, the heart and coronary blood vessels must be isolated from the remainder of the circulatory system. This serves several purposes. First, such isolation facilitates infusion of cardioplegic fluid into the coronary arteries in order to perfuse the myocardium and thereby arrest cardiac function, without allowing the cardioplegic fluid to be distributed elsewhere in the patient's circulatory system. Second, such isolation facilitates the use of a cardiopulmonary bypass system to maintain circulation of oxygenated blood throughout the circulatory system while the heart is stopped, without allowing such blood to reach the coronary arteries which might resuscitate the heart. Third, in cardiac procedures, such isolation creates a working space into which the flow of blood and other fluids can be controlled or prevented so as to create an optimum surgical environment.

Using current techniques, isolation of the heart and coronary blood vessels is accomplished by placing a mechanical cross-clamp externally on the ascending aorta downstream of the ostia of the coronary arteries, but upstream of the brachiocephalic artery, so as to allow oxygenated blood from the cardiopulmonary bypass system to reach the arms, neck, head, and remainder of the body. A catheter is then inserted directly into the ascending aorta between the cross-clamp and the aortic valve, and cardioplegic fluid is infused through the catheter into the ascending aorta and coronary arteries to perfuse the myocardium and/or to vent or decompress the heart. An additional catheter may be introduced into the coronary sinus for retrograde perfusion of the myocardium with cardioplegic fluid. In addition, the myocardium is usually cooled by irrigating with cold saline solution and/or application of ice or cold packs to the myocardial tissue. Cardiac contractions will then cease.

Known techniques for performing major surgeries such as coronary artery bypass grafting and heart valve repair and replacement have generally required open access to the thoracic cavity through a large open wound, known as a thoracotomy. Typically, the sternum is cut longitudinally (a median sternotomy), providing access between opposing halves of the anterior portion of the rib cage to the heart and other thoracic vessels and organs. An alternate method of entering the chest is via a lateral thoracotomy, in which an incision, typically 10 cm to 20 cm in length, is made between two ribs. A portion of one or more ribs may be permanently removed to optimize access.

In procedures requiring a median sternotomy or other type of thoracotomy, the ascending aorta is readily accessible for placement of an external cross-clamp through this large opening in the chest. However, such surgery often entails weeks of hospitalization and months of recuperation time, in addition to the pain and trauma suffered by the patient. Moreover, while the average mortality rate associated with this type of procedure is about two to fifteen per cent for first-time surgery, mortality and morbidity are significantly increased for reoperation. Further, significant complications may result from such procedures. For example, application of an external cross-clamp to a calcified or atheromatous aorta may cause the release of emboli into the brachiocephalic, carotid or subclavian arteries with serious consequences such as strokes. In up to 6% of the open-chest coronary bypass surgeries performed in the United States, there is noticeable mental deterioration which is commonly attributed to cerebral arterial blockage from emboli released during the bypass procedure. Methods and devices are therefore needed for isolating the heart and coronary arteries from the remainder of the arterial system, arresting cardiac function and establishing cardiopulmonary bypass without the open-chest access provided by a median sternotomy or other type of thoracotomy. Further, the methods and devices should facilitate such isolation of the heart and coronary arteries without the high risk of embolus production associated with external aortic cross-clamps.

One medical procedure of particular interest to the present invention is the treatment of heart valve disease. Co-owned, copending patent application Ser. No. 08/281,962, which has been incorporated by reference, describes a method of performing closed-chest or thoracoscopic heart valve replacement surgery. Isolating the heart from the systemic blood circulation, inducing cardioplegic arrest and establishing cardiopulmonary bypass are important steps in the performance of the heart valve replacement procedure. The devices, systems and methods of isolating and arresting the heart described in the present patent application will find particular utility in the performance of that procedure.

Of additional interest to the invention are techniques for establishing cardiopulmonary bypass and for performing interventional procedures in the heart and great vessels which minimize trauma and risk of complications resulting from vascular penetrations, whether percutaneous punctures or surgical cutdowns. To establish cardiopulmonary bypass according to conventional techniques, a venous cannula is introduced into a major vein such as the inferior vena cava, or into the heart itself, to withdraw deoxygenated blood from the patient and deliver the deoxygenated blood to a CPB system for oxygenation. An arterial cannula is introduced into a major artery such as the aorta, an iliac artery, or a femoral artery, for delivering oxygenated blood from the CPB system to the patient's arterial system.

For endovascular procedures such as angioplasty, atherectomy, valvuloplasty, cardiac mapping and ablation, and the like, interventional devices are introduced into a peripheral artery and transluminally positioned at the treatment site where the procedure is performed. For example, in angioplasty or atherectomy, a catheter is introduced into a femoral artery and advanced through the aorta into a coronary artery to treat an occluded region therein. In some circumstances, the use of CPB may be desirable during such procedures. If CPB is utilized during these procedures, the arterial and venous CPB cannulae are usually introduced into a femoral artery and femoral vein, respectively, by means of a surgical cutdown in the groin area on one side of a patient's body. The endovascular interventional devices may then be introduced into a femoral artery in the groin area on the other side of the patient's body.

In order to minimize trauma and the risk of complications such as infection, it is generally desirable to minimize the number of vascular penetrations or "sticks" which are made in a patient during a procedure. Such penetrations are a significant cause of morbidity and mortality in cardiac procedures. The risks are greater where the penetrations are either surgical cutdowns or large percutaneous penetrations, as are usually required for introduction of venous and arterial CPB cannulae and for some types of endovascular interventional devices. The risks are particularly high when such penetrations are made on arterial vessels.

Moreover, in some cases, one or more of a patient's femoral arteries, femoral veins, or other vessels for arterial and venous access may not be available for introduction of cannulae, due to inadequate vessel diameter, vessel stenosis, vascular injury, or other conditions. In such cases, there may not be sufficient arterial and venous access to permit the use of femoral arterial and venous CPB cannulae as well as other interventional devices, such as an angioplasty catheter, atherectomy catheter or other device, introduced through a femoral vein or artery contemporaneously as part of a single surgical procedure. Therefore, unless alternate arterial or venous access for one or more of these catheters can be found, the procedure cannot be performed using endovascular techniques.

What have been needed and heretofore unavailable are methods and systems for satisfactorily performing various cardiovascular procedures, particularly procedures for heart valve placement or removal and replacement, which do not require a thoracotomy. Improved methods and devices are also needed for establishing CPB and performing interventional procedures that reduce the number of arterial and venous penetrations required for CPB cannulae and other endovascular devices. The methods and devices will preferably facilitate isolating the heart and coronary arteries from the remainder of the arterial system, arresting cardiac function, and establishing cardiopulmonary bypass without the open-chest access provided by a thoracotomy. The methods and devices should minimize the number of arterial and venous penetrations required in such closed-chest procedures, and desirably, should require no more than one femoral arterial penetration and one femoral venous penetration. In addition to procedures requiring arrest of cardiac function, the methods and devices should be useful for a variety of closed-chest interventional procedures that require the use of cardiopulmonary bypass, even where cardiac function is not arrested. The present invention satisfies these and other needs.

The descriptive terms downstream and upstream, when used herein in relation to the patient's vasculature, refer to the direction of blood flow and the direction opposite that of blood flow, respectively. In the arterial system, downstream refers to the direction further from the heart, while upstream refers to the direction closer to the heart. The terms proximal and distal, when used herein in relation to instruments used in the procedure, refer to directions closer to and farther away from the operator performing the procedure.

SUMMARY OF THE INVENTION

The present invention is directed to a method and system for an endovascular approach for preparing a patient's heart for cardiac procedures which does not require a grossly invasive thoracotomy. The invention contemplates, at least in its preferred embodiments, the possibility of effective ascending aortic occlusion, cardioplegia, venting, right heart deflation and topical cooling in association with extracorporeal cardiopulmonary bypass all without necessitating a median sternotomy or other thoracic incision.

The endovascular system of the invention includes an elongated aortic partitioning catheter having proximal and distal ends and an occluding member on a distal portion of the catheter adapted to occlude a patient's ascending aorta. The catheter preferably has an inner lumen extending within the catheter to a port in the distal end of the catheter. The catheter is adapted to be inserted into the patient's arterial system (e.g. through the femoral or brachial arteries) and to be advanced to the ascending aorta where the occluding member is expanded to occlude the aorta at that location. In so doing the left ventricle of the heart and an upstream portion of the ascending aorta are separated from the rest of the patient's arterial system. This catheter thus constitutes an endovascularly inserted, internal vascular clamp, similar in function to the external "cross-clamp" used in open cardiac surgical procedures. The internal clamp is less traumatic to the clamped vessel, and provides a lumen or working channel through which instruments or fluids may be passed into or withdrawn from the area upstream of the distal end of the clamp. The occluding member on the elongated catheter should be dimensioned so that upon expansion it will be located downstream from the ostia for the coronary arteries and upstream from the brachiocephalic artery so as to avoid blocking these arteries.

Also included with the system is a cardiopulmonary bypass system which withdraws blood from the patient's venous system, e.g. the femoral or jugular vein, removes $CO_2$ from and adds oxygen to the withdrawn blood, and then returns the oxygenated blood to the patient's arterial system, e.g. the femoral or brachial artery. The system is also provided with means to deliver a fluid containing cardioplegic material (e.g. an aqueous solution of KCl and/or magnesium procaine and the like) through the coronary arteries so as to temporarily paralyze the myocardium.

In a further aspect the present invention consists of a method for inducing cardioplegic arrest of a heart in situ in a patient's body, comprising the steps of:

(a) maintaining systemic circulation with peripheral cardiopulmonary bypass;

(b) partitioning the coronary arteries from the ascending aorta by, e.g., occluding the ascending aorta through a percutaneously placed arterial balloon catheter;

(c) introducing a cardioplegic agent into the coronary circulation; and (d) venting the heart.

The method according to the present invention may be carried out on humans or other mammalian animals. The method is of particular applicability in humans as it allows an alternative approach to open heart surgery and the development of closed cardioscopic surgery. The method according to the invention enables a percutaneous bypass system to be associated with cardioplegia, venting and cooling of the heart which subverts the need for median sternotomy. This may, in turn, reduce the complications of the surgery.

In one preferred embodiment, the occluding member of the aortic partitioning catheter constitutes an inflatable cuff or balloon of sufficient size that upon being inflated it is able to completely occlude the ascending aorta. The length of the balloon should preferably not be so long as to impede the flow of blood or other solution to the coronary arteries or to the brachiocephalic, left carotid or left subclavian arteries. A balloon length of about 40 mm and diameter of about 35 mm is suitable in humans. The balloon may be of a cylindrical, spherical, ellipsoidal or other appropriate shape to fully and evenly accommodate the lumen of the ascending aorta. This maximizes the surface area contact with the aorta, and allows for even distribution of occlusive pressure.

The balloon of the catheter is preferably inflated with a saline solution, or more preferably with saline solution mixed with a radiopaque contrast agent, to avoid the possibility of introducing into the patient an air embolism in the event that the balloon ruptured. The balloon should be inflated to a pressure sufficient to prevent regurgitation of blood into the aortic root and to prevent migration of the balloon into the root whilst not being so high as to cause damage or dilation to the aortic wall. An intermediate pressure of the order of 350 mmHg, for example, has been proven effective.

The aortic partitioning catheter is preferably introduced under fluoroscopic guidance over a suitable guidewire. Transoesophageal echocardiography can alternatively be used for positioning the aortic catheter. The catheter may serve a number of separate functions and the number of lumina in the catheter will depend upon how many of those functions the catheter is to serve. The catheter can be used to introduce the cardioplegic agent, normally in solution, into the aortic root via one lumen. The luminal diameter will preferably be such that a flow of the order of 250–500 ml /min of cardioplegic solution can be introduced into the aortic root under positive pressure to perfuse adequately the heart by way of the coronary arteries. The same lumen can, by applying negative pressure to the lumen from an outside source, effectively vent the left heart of blood or other solutions. It may also be desirable to introduce medical instruments and/or a cardioscope into the heart through another lumen in the catheter. The lumen should be of a diameter suitable to pass a fiberoptic light camera of no greater than 3 mm diameter. It is however, preferable that the diameter and cross-sectional design of the internal lumina are such that the external diameter of the catheter in its entirety is small enough to allow its introduction into the adult femoral artery by either percutaneous puncture or direct cutdown.

The oxygenated blood returning to the body from the bypass system may be conveyed into the aorta from another lumen in the cannula carrying the balloon. In this case the returning blood is preferably discarded from the catheter in the external iliac artery. In another embodiment of the invention, and in order to reduce the diameter of the catheter carrying the balloon, a separate arterial catheter of known type may be used to return blood to the patient from the bypass system. In this case a short catheter is positioned in the other femoral artery to provide systemic arterial blood from the bypass system. The control end of the catheter, i.e. that end that remains outside of the body, should have separate ports of attachment for the lumina. The catheter length should be approximately 900 mm for use in humans.

The cardioplegic agent may be any of the known materials previously known to be useful, or in the future found to be useful, as cardioplegic agents. The agent is preferably infused as a solution into the aortic root through one of the lumina of the aortic catheter.

With the heart paralyzed, the expandable member of the aortic catheter expanded within the ascending aorta, and the cardiopulmonary bypass operating, the heart is prepared for a cardiac procedure. While a particularly attractive feature of the invention is that it prepares the heart for endovascular, thoracoscopic, and other minimally-invasive procedures, the invention can also be used to prepare the heart for conventional open-heart surgery via a thoracotomy. It should also be noted that, if during an endovascular cardiac procedure in accordance with the invention it becomes necessary to perform an open-heart procedure, the patient is already fully prepared for the open-heart procedure. All that is necessary is to perform a median sternotomy to expose the patient's heart for the conventional surgical procedure.

In a further aspect, the invention provides endovascular devices and methods for partitioning a patient's ascending aorta between the coronary ostia and the brachiocephalic artery to isolate the heart and coronary arteries from the remainder of the arterial system, arrest cardiac function, and establish cardiopulmonary bypass. The invention also provides a system and method for arresting the heart that facilitate isolating the heart and coronary arteries from the remainder of the arterial system, arresting cardiac function, and establishing cardiopulmonary bypass without the need for a thoracotomy or an external aortic cross-clamp.

Using the device, system and method of the invention, all blood flow through the ascending aorta may be blocked and cardioplegic fluid may be introduced through the coronary arteries to perfuse the myocardium. With the patient connected to cardiopulmonary bypass equipment to maintain circulation of oxygenated blood while the heart is stopped, surgical procedures may be performed on the heart, coronary blood vessels and other body structures using thoracoscopic and/or endovascular tools, without the need for a thoracotomy. Moreover, by partitioning the aorta by endovascular occlusion rather than by external cross-clamping, the device of the invention may substantially reduce the risk of embolus release associated with such cross-clamping.

In a particular aspect of the invention, an endovascular device for partitioning the ascending aorta between the coronary ostia and the. brachiocephalic artery comprises a flexible shaft having a distal end, a proximal end, and a first inner lumen therebetween with an opening at the distal end in communication with the first inner lumen. The shaft has a distal portion which is shaped so as to be positionable within the aortic arch such that the distal end is disposed in the ascending aorta pointing toward the aortic valve. Preferably, the distal portion will be shaped so that the distal end of the shaft is spaced apart from any interior wall of the aorta, and particularly, so that the distal end is aligned with the center of the aortic valve. Expandable means are disposed near the distal end of the shaft proximal to the opening at the distal end for occluding the ascending aorta between the coronary ostia and the brachiocephalic artery, thereby blocking substantially all systolic and diastolic blood flow. The first inner lumen of the shaft may be used to withdraw blood or other fluids from the ascending aorta, to introduce cardioplegic fluid into the coronary arteries for paralyzing the myocardium, and/or to introduce surgical instruments into the ascending aorta, the coronary arteries, or the heart for performing cardiac procedures.

By "shaped," it is meant that the distal portion of the shaft is preset in a permanent, usually curved or bent shape in an unstressed condition to facilitate positioning the distal portion within at least a portion of the aortic arch, or that such a shape is imparted to the distal portion of the shaft by means of a shaping or deflecting element positioned over or within the shaft, as described in detail below.

In one preferred embodiment, the distal portion of the shaft is preshaped so as to have a generally U-shaped configuration which subtends approximately 180°±45° of arc in an unstressed condition. Preferably, the U-shaped distal portion has a curvature corresponding to the curvature of the patient's aortic arch, usually having a radius of curvature in a range of 20 to 80 mm. In this way, when the preshaped distal portion is positioned in the aortic arch, the distal end will be disposed in the ascending aorta spaced apart from the interior wall thereof. Alternatively, the distal portion may have straight or curved segments with bends of relatively small radius between each segment to achieve a general "U" shape. The bends and/or segments of the preshaped distal portion may be configured to engage the interior wall of the aortic arch to deflect the distal end into a desired position in the ascending aorta. In one particular embodiment of the aortic partitioning catheter, the end of the catheter distal to the U-shaped curve has a straight segment which resides in the ascending aorta with an eccentrically shaped occlusion balloon mounted near the distal end of the straight segment. The eccentric balloon is preferably mounted on the catheter so that the larger side of the balloon is oriented toward the outside of the U-shaped curve, that is, facing toward the right side of the patient. Because the ascending aorta in the human is typically curved, rather than straight like the distal segment of the catheter, the eccentric balloon compensates for the mismatch of the curves and serves to center the tip of the catheter within the ascending aorta just above the aortic root.

In other preferred embodiments, the distal portion is preshaped to have a compound curve which subtends an arc of approximately 270°±45°, preferably in the range of 270°–300°. The compound curve, which may be made up of a combination of arc-shaped portions, angular bends and straight segments, serves to correctly position the distal end of the catheter within the ascending aorta with the catheter tip centered in the aortic lumen just above the aortic root and to stabilize the catheter in that position. The preshaped distal portion of the shaft may further have a distal segment which is positioned in the ascending aorta and a proximal segment which is positioned in the descending aorta, wherein the distal segment is skewed (non-coplanar) relative to the proximal segment. Such a configuration mirrors the orientation of the ascending aorta relative to the aortic arch and descending aorta, facilitating more accurate placement of the distal end in the ascending aorta, spaced apart from the interior wall thereof, and preferably, aligned with the center of the aortic valve.

The invention preferably includes means in the shaft for straightening the preshaped distal portion. Usually, the straightening means comprises a straightening element slidably disposed in the first inner lumen having a stiffness greater than the stiffness of the preshaped distal portion. The straightening element may comprise a relatively stiff portion of a flexible guidewire extending through the first inner lumen, or a stylet having an axial passage through it for receiving a movable guidewire.

In an exemplary embodiment, the occluding means has a collapsed profile for insertion into an artery such as a femoral and an expanded profile for occluding the ascending aorta, with the expanded profile diameter being about 2 to 10 times, and preferably 5 to 10 times, the collapsed profile diameter. In one preferred embodiment, the occluding means comprises an inflatable balloon made of an elastomeric material, such as polyurethane, silicone or latex. In other embodiments, the occlusion means comprises an inflatable balloon made of a nondistensible balloon material, such as polyethylene, polyethylene terephthalate polyester, polyester copolymers, polyamide or polyamide copolymers. The balloon is further configured to maximize contact with the aortic wall to resist displacement and prevent leakage around the balloon, preferably having a working surface for contacting the aortic wall with a length in the range of about 1 to about 7 cm, more preferably in the range of about 2 to 5 cm, when the balloon is expanded to fully occlude the vessel.

Where a balloon is used for the occluding means, the endovascular device has an inflation lumen extending through the shaft from the proximal end to the interior of the balloon, and means connected to the proximal end of the inflation lumen for delivering an inflation fluid to the interior of the balloon. In one preferred embodiment, the inflation lumen is configured to allow inflation of the balloon with a liquid, such as a mixture of saline solution and a radiographic contrast agent, in less than 40 seconds, preferably in approximately 20 seconds or less. In another preferred embodiment, the inflation fluid delivery means and the inflation lumen are configured to inflate the balloon with a gas such as carbon dioxide or helium in order to inflate the balloon in less than about 0.5 seconds. In this way, the balloon may be fully inflated between systolic contractions of the heart, reducing the likelihood of balloon displacement caused by high pressure blood flow during systole.

The shaft of the endovascular device of the invention may have a variety of configurations. The first inner lumen and inflation lumen may be coaxial, or a multilumen design may be employed. The shaft may further include a third lumen extending from the proximal end to the distal end of the shaft, allowing pressure distal to the occluding means to be measured through the third lumen. The shaft may also include means for maintaining the transverse dimensions of the first inner lumen, which may comprise a wire coil or braid embedded in at least the distal portion of the shaft to develop radial rigidity without loss of longitudinal flexibility. The shaft preferably has a soft tip at its distal end to prevent damage to the heart valve if the catheter comes into contact with the delicate valve leaflets.

The shaft preferably has a length of at least about 80 cm, usually about 90–125 cm, to allow transluminal positioning of the shaft from the femoral and iliac arteries to the ascending aorta. Alternatively, the shaft may have a shorter length, e.g. 20–60 cm, for introduction through the iliac artery, through the brachial artery, through the carotid artery, or through a penetration in the aorta itself.

Because of its proximity to the left ventricle, the occluding means of the device is subject to significant forces from the outflow of blood during systole. Such forces could threaten to displace the occluding means either downstream where it might occlude the ostium of the brachiocephalic or other artery, or upstream (in a recoil effect) where the occluding means might damage the aortic valve or occlude the coronary ostia. Advantageously, the endovascular device of the invention is configured to maintain the position of the occluding means in the ascending aorta against the force of systolic outflow as the occluding means is expanded and retracted, as well as during the period in which the occluding means fully occludes the aorta but the heart remains beating.

In addition, the shaped distal portion of the device maintains the distal end in a radial position spaced apart from the interior wall of the ascending aorta such that the distal opening is unobstructed and generally aligned with the center of the aortic valve. This facilitates aspiration of blood, other fluids, or debris, infusion of fluids, or introduction of instruments through the distal opening in the endovascular device without interference with the aortic wall or aortic valve tissue.

In a further preferred embodiment, the invention provides a system for selectively arresting the heart which includes an endovascular aortic partitioning device as just described, along with means for paralyzing the patient's myocardium. Usually, the means for paralyzing the myocardium comprises means connected to the proximal end of the shaft for delivering cardioplegic fluid through the first inner lumen and out of the opening at the distal end of the device upstream of the occluding means. In this way, the occluding means may be expanded to stop blood flow through the ascending aorta, and cardioplegic fluid may be delivered through the first inner lumen to the aortic root and the coronary arteries to perfuse the myocardial tissue, thereby arresting the heart. The system may further include a cardiopulmonary bypass system having means for withdrawing blood from a venous location upstream of the heart, means for oxygenating the withdrawn blood, and means for directing the oxygenated blood to an arterial location downstream of the occluding means.

According to the method of the invention, the distal end of the shaft of the endovascular partitioning device is introduced into a blood vessel downstream of the patient's aortic arch. The shaft is transluminally positioned so that the distal end is in the ascending aorta and the expandable occluding member attached to the shaft near the distal end is disposed between the coronary ostia and brachiocephalic artery. The occluding member is then expanded within the ascending aorta to completely block blood flow therethrough for a plurality of cardiac cycles.

In those embodiments in which the shaft of the partitioning device has a preshaped distal portion, the method will usually include the step of straightening the preshaped distal portion to facilitate introduction into the blood vessel, usually by positioning a stylet or guidewire in an inner lumen in the shaft. The stylet may be withdrawn from the shaft as the distal portion is advanced into the ascending aorta to allow the distal portion to resume its preshaped configuration. In a particular embodiment, the method may further include, before the step of introducing the shaft into the blood vessel, the steps of determining a size of the patient's aortic arch, and selecting a shaft having a shaped distal portion corresponding to the dimensions and geometry of the aortic arch.

Preferably, the shaft of the partitioning device is introduced through a femoral or iliac artery, brachial artery, carotid artery or other artery which is percutaneously accessible without a thoracotomy. In this way, the device may be introduced and advanced into position with the patient's sternum and rib cage intact.

When the occluding member is an inflatable balloon, the method further includes the step of delivering an inflation fluid to the balloon through an inner lumen in the shaft of the device. The inflation fluid may be either a liquid or a gas. In one embodiment, the inflation medium is an aqueous liquid containing a radiopaque contrast agent which is delivered at a rate to inflate the balloon in 40 seconds or less, preferably 20 seconds or less. In another embodiment, the inflation medium is a gas which is delivered at a rate to completely occlude the aorta between systolic contractions of the heart, usually in less than about 0.5 second.

The method may further include paralyzing the patient's myocardium while the occluding means is expanded in the ascending aorta. Usually, this will be accomplished by infusing cardioplegic fluid through an inner lumen in the shaft of the partitioning device into the ascending aorta upstream of the occluding member. The cardioplegic fluid perfuses the myocardium through the coronary arteries to arrest heart contractions. In this embodiment, the method further includes the steps of withdrawing blood from a venous location upstream of the patient's heart, oxygenating the withdrawn blood, and directing the oxygenated blood to an arterial location downstream of the occluding member, thereby maintaining circulation of oxygenated blood throughout the remainder of the patient's arterial system.

Thus, using the system and method of the invention, a patient's heart can be arrested and the patient placed on cardiopulmonary bypass without a thoracotomy, thereby reducing mortality and morbidity, decreasing patient suffering, reducing hospitalization and recovery time, and lowering medical costs relative to previous open-chest procedures. The endovascular partitioning device of the invention permits blood flow through the ascending aorta to be completely blocked between the coronary ostia and the brachiocephalic artery in order to isolate the heart and coronary arteries from the remainder of the arterial system. This has significant advantages over the aortic cross-clamps used in current cardiac procedures, not only obviating the need for a thoracotomy, but providing the ability to stop blood flow through the aorta even when calcification or other complications would make the use of an external cross-clamp undesirable.

With the endovascular partitioning device in place, the heart arrested and cardiopulmonary bypass established, the patient is prepared for a variety of surgical and diagnostic procedures, including repair or replacement of aortic, mitral and other heart valves, repair of septal defects, pulmonary thrombectomy, coronary artery bypass grafting, angioplasty, atherectomy, electrophysiological mapping and ablation, treatment of aneurysms, myocardial drilling, as well as neurovascular and neurosurgical procedures. While such procedures may be performed through a thoracotomy in the conventional manner, the invention provides the capability for performing procedures such as heart valve replacement or coronary artery bypass grafting using minimally-invasive techniques, either by means of surgical tools introduced endovascularly through the partitioning device itself, or by means of thoracoscopic tools introduced through small incisions in the chest wall.

In an alternate method of the present invention, the cardioplegic fluids may be delivered to the myocardium by retrograde perfusion of the coronary circulation. Using this technique, a physician will percutaneously introduce a catheter through a major vein, e.g. the right internal jugular vein, and advance the catheter in the venous system until the distal end of the catheter extends into the coronary sinus through the discharge opening thereof in the right atrium. Preferably, the catheter has an inflatable balloon on the distal end thereof, such as those shown in U.S. Pat. No. 4,689,041, U.S. Pat. No. 4,943,277, and U.S. Pat. No. 5,021,045, which are incorporated herein by reference. When inflated, the balloon blocks the discharge opening of the coronary sinus to preclude loss of cardioplegic fluid therefrom. With the discharge opening of the coronary sinus blocked off, aqueous liquid or other fluid containing cardioplegic material is delivered through the catheter into the coronary sinus at sufficient pressure so that it passes into the myocardium via the capillary bed between the venous and arterial systems therein so as to paralyze the entire myocardium. Typically, cardioplegic solution pressure within the coronary sinus should be less than 50 mm Hg to avoid tissue damage. After passing through the myocardium, the cardioplegic liquid will pass through the coronary arteries in a retrograde fashion to be discharged through the coronary ostia into the upstream portion of the ascending aorta. The cardioplegic fluid which discharges from the coronary ostia will initially be very opaque due to blood being flushed out of the coronary circulation, but eventually the fluid will become clear and may be conveniently used to form and maintain the body of clear fluid at the surgical site to facilitate the imaging thereof during the procedure. In some instances, cardioplegic liquid may instead be delivered through the coronary arteries in an antegrade fashion, either via catheters placed through the coronary ostia into the coronary arteries or by delivery via the aortic catheter directly into the aortic root.

The present invention further provides endovascular devices and methods for establishing cardiopulmonary bypass and performing interventional procedures within the heart and great vessels with a minimum of arterial and venous penetrations. Using the devices and methods of the invention, all blood flow through the ascending aorta may be blocked, cardioplegic fluid may be introduced through the coronary arteries to perfuse the myocardium, and oxygenated blood from a CPB system may be infused into the arterial system downstream from the point of aortic occlusion, all through a single femoral arterial penetration. Moreover, blood may be vented from the heart to prevent distension of the myocardium, and deoxygenated blood withdrawn from a venous location for oxygenation by the CPB system, all through a single femoral or jugular venous penetration.

In an additional aspect of the invention, a cardiopulmonary bypass cannula is provided which is adapted to allow endovascular introduction of the endoaortic partitioning catheter through a lumen of the cannula so as to reduce the number of cutdowns or percutaneous arterial or venous punctures necessary for establishing cardiopulmonary bypass. The shaft of the endoaortic partitioning catheter is slidably disposed in the blood flow lumen of the bypass cannula, and may be removable from the bypass cannula, and/or limited in its movement relative to the bypass cannula. The bypass cannula may further be provided with a plurality of ports along a distal portion of its length in fluid communication with the blood flow lumen to enhance the flow of blood into or out of the blood flow lumen. In the arterial embodiment, the blood flow lumen is preferably configured to facilitate a fluid flow of at least about 4 liters/minute at a pressure of less than about 250 mmHg.

The bypass cannula may further have an adapter assembly mounted to its proximal end. The adapter assembly has first and second access ports in communication with the blood flow lumen, the first access port being configured to receive the catheter shaft, and the second access port being configured for connection to the oxygenated blood delivery means (in the arterial embodiment) or a means for receiving and oxygenating deoxygenated blood (in the venous embodiment). Usually, a hemostasis valve or other sealing means is mounted in the first access port to prevent leakage of blood therefrom, both when the catheter shaft is inserted through the first access port as well as when the catheter shaft is removed from the first access port. In the arterial embodiment, the bypass cannula has a length between about 10 cm and 60 cm, and preferably about 15 cm to 30 cm, such that the outflow port at the distal end of the bypass cannula is disposed a substantial distance downstream of the occluding member on the catheter shaft. If it is used on the venous side, the bypass cannula is preferably about 50 cm to 90 cm in length so as to extend from a femoral vein to a point in the inferior vena cava near the heart, to a point within the right atrium of the heart, or to a point in the superior vena cava near the heart. Alternatively, the venous bypass cannula may be configured for introduction into the internal jugular vein and positioning therefrom into the superior vena cava, the right atrium, or the inferior vena cava.

According to the method of the invention, a distal end of a bypass cannula is positioned in a blood vessel of a patient, and a proximal end of the bypass cannula is connected to a CPB system to permit blood flow through a blood flow lumen in the bypass cannula between the blood vessel and the CPB system. An interventional device is then introduced through the blood flow lumen of the bypass cannula into the blood vessel and advanced into the heart or into a great vessel near the heart to perform an interventional procedure therein.

In a particular embodiment, the bypass cannula is introduced into an artery downstream of the patient's ascending aorta, and a distal end of a catheter shaft is introduced into the artery through the blood flow lumen in the bypass cannula. The catheter shaft is transluminally positioned so that an expandable occluding member attached to the catheter shaft near the distal end is disposed between the patient's coronary ostia and the patient's brachiocephalic artery. Oxygenated blood is infused into the artery downstream of the occluding member through a lumen in the bypass cannula. The occluding member is expanded within the ascending aorta to completely block blood flow therethrough for a plurality of cardiac cycles. The patient's myocardium is then paralyzed.

In most embodiments, the bypass cannula will be connected to a CPB system which withdraws blood from a venous location in the patient, oxygenates the blood, and delivers the oxygenated blood to the blood flow lumen in the bypass cannula on the arterial side. The deoxygenated blood may be withdrawn through a blood flow lumen in a venous cannula positioned in a vein such as a femoral vein or internal jugular vein. Also, a cardiac venting catheter may be positioned in the heart, usually in the pulmonary artery, to withdraw blood therefrom and deliver it to the CPB system. In an exemplary embodiment, the cardiac venting catheter is introduced through the blood flow lumen in the venous cannula. Preferably, the venous and arterial bypass cannulae are introduced into a femoral vein and femoral artery, respectively, in the groin area on the same side of the patient. In this way, both the venous and arterial bypass cannulae, as well as the devices introduced therethrough, may be introduced through a single surgical cutdown or percutaneous punctures on a single side of the patient.

Thus, using the system and method of the invention, a patient's heart can be arrested and the patient placed on cardiopulmonary bypass without a conventional gross thoracotomy, thereby reducing mortality and morbidity, decreasing patient suffering, reducing hospitalization and recovery time, and lowering medical costs relative to previous open-chest procedures. The endovascular partitioning device of the invention permits blood flow through the ascending aorta to be completely blocked between the coronary ostia and the brachiocephalic artery in order to isolate the heart and coronary arteries from the remainder of the arterial system. This has significant advantages over the aortic cross-clamps used in current cardiac procedures, not only obviating the need for a gross thoracotomy, but providing the ability to stop blood flow through the aorta even when calcification or other complications would make the use of an external cross-clamp undesirable. Moreover, the device and method of the invention accomplish this with a minimum of arterial penetrations, thereby minimizing trauma and the risk of complications such as infection.

The system and method of the invention may further be useful to provide cardiopulmonary bypass during endovascular interventional procedures in which cardiac function may or may not be arrested. Such procedures may include angioplasty, atherectomy, heart valve repair and replacement, septal defect repair, treatment of aneurysms, myocardial mapping and ablation, myocardial drilling, and a variety of other procedures wherein endovascular interventional devices are introduced through the bypass cannula of the invention and advanced into the heart or great vessels. In this way, the invention facilitates cardiopulmonary bypass during such procedures without requiring additional arterial or venous penetrations.

The occluding aortic catheter with an expandable occluding member on the distal end, coupled with cardiopulmonary bypass, cardioplegia, and decompression of the left atrium, provides for a unique endovascular approach to a wide variety of cardiac procedures, an approach which does not require invasive thoracic or abdominal surgery. In addition the system may be used in minimally invasive cardiac procedures under thoracoscopic guidance, working through incisions in the patient's chest from outside the patient's body. In these instances the occluding catheter need not have an inner lumen for delivery of fluids and the like. The catheter and method according to the present invention can be used to induce cardioplegic arrest and may be used in a number of surgical procedures.

Moreover, as mentioned, the system may even be employed in conventional open-heart procedures. These and other advantages of the invention will become more apparent from the following detailed description of the invention when taken in conjunction with the accompanying exemplary drawings.

BRIEF DESCRIPTION OF THE DRAWINGS

FIG. 7A is a longitudinal cross section of a third embodiment of the endoaortic partitioning catheter having piezoelectric pressure transducers.

FIG. 7B is a lateral cross section of the catheter of FIG. 7A taken along the lines 7B—7B.

FIG. 7C is a lateral cross section of the catheter of FIG. 7A taken along the lines 7C—7C.

FIG. 9A is a side view, partially in section, of a fifth embodiment of the endoaortic partitioning catheter having a twisted low-profile occlusion balloon.

FIG. 9B is a longitudinal cross section of the catheter of FIG. 9A with the occlusion balloon inflated.

FIG. 10A is a front view of a sixth embodiment of the endoaortic partitioning catheter having a precurved distal end.

FIG. 10B is a side view of the catheter of FIG. 10A.

FIG. 10C is a lateral cross section of the catheter of FIG. 10A taken along the lines 10C—10C.

FIG. 12A is a front view of a seventh embodiment of the endoaortic partitioning catheter having a precurved distal end.

FIG. 12B is a side view of the catheter of FIG. 12A.

FIG. 12C is a lateral cross section of the catheter of FIG. 12A taken along the lines 12C—12C.

FIG. 20A is a front view of a twelfth embodiment of the endoaortic partitioning catheter having a nondistensible aortic occlusion balloon.

FIG. 20B is an end view of the catheter of FIG. 20A.

FIG. 20C is a side view of the catheter of FIG. 20A with the occlusion balloon wrapped around the catheter shaft.

FIG. 20D is an end view of the catheter of FIG. 20C.

FIGS. 35A–35C illustrate an endoaortic partitioning catheter having a steerable distal tip with a multichamber balloon for centering the catheter tip within the ascending aorta.

DETAILED DESCRIPTION OF THE INVENTION

The invention provides a cardiac access system including an endovascular device for partitioning the ascending aorta, as well as a system for selectively arresting the heart, which are useful in performing a variety of cardiovascular, pulmonary, neurosurgical, and other procedures. The procedures with which the invention will find use include repair or replacement of aortic, mitral, and other heart valves, repair of septal defects, pulmonary thrombectomy, electrophysiological mapping and ablation, coronary artery bypass grafting, angioplasty, atherectomy, treatment of aneurysms, myocardial drilling and revascularization, as well as neurovascular and neurosurgical procedures. The invention is especially useful in conjunction with minimally-invasive cardiac procedures, in that it allows the heart to be arrested and the patient to be placed on cardiopulmonary bypass using only endovascular devices, obviating the need for a thoracotomy or other large incision. Moreover, even in conventional open-chest procedures, the endovascular aortic partitioning device of the invention will frequently find use where an external cross-clamp would raise substantial risks of embolus release due to calcification or other aortic conditions.

Figure 1:
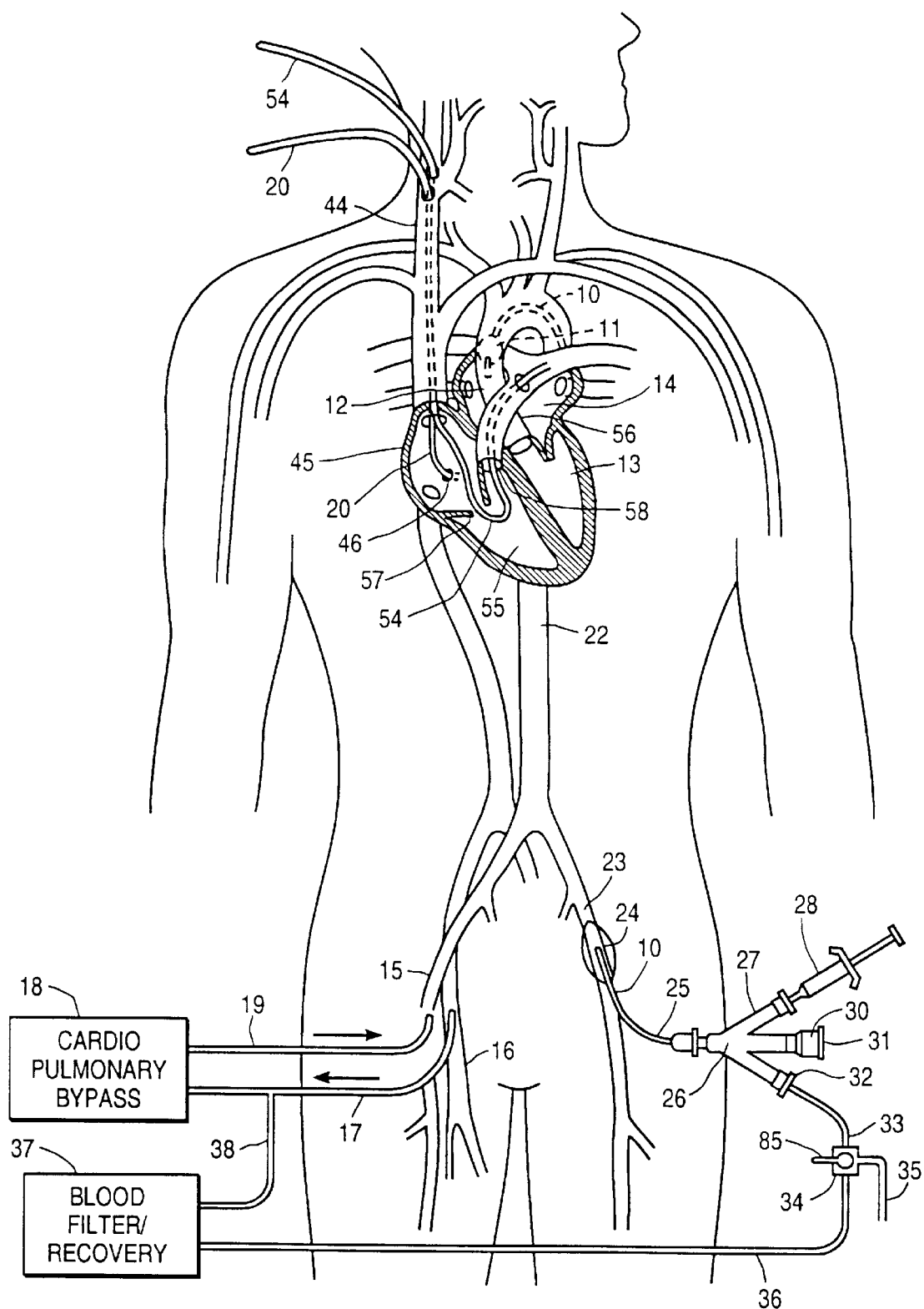
FIG. 1 schematically illustrates a cardiac access system employing the endoaortic partitioning catheter of the present invention.

Reference is made to FIG. 1 which schematically illustrates the overall cardiac accessing system of the invention and the individual components thereof. The accessing system includes an elongated aortic occlusion or endoaortic partitioning catheter 10 which has an expandable member 11 on a distal portion of the catheter which, when inflated as shown, occludes the ascending aorta 12 to separate or partition the left ventricle 13 and upstream portion of the ascending aorta from the rest of the patient's arterial system and securely positions the distal end of the catheter within the ascending aorta. A cardiopulmonary bypass system 18 removes venous blood from the femoral vein 16 through the blood withdrawal catheter 17 as shown, removes $CO_2$ from the blood, oxygenates the blood, and then returns the oxygenated blood to the patient's femoral artery 15 through the return catheter 19 at sufficient pressure so as to flow throughout the patient's arterial system except for the portion blocked by the expanded occluding member 11 on the aortic occluding catheter 10. The aortic occluding catheter 10 has an infusion lumen 40 for antegrade delivery of a fluid containing cardioplegic agents directly into the aortic root 12 and subsequently into the coronary arteries 52, 53 (shown in FIG. 2) to paralyze the patient's myocardium. Optionally, a retrograde cardioplegia balloon catheter 20 may be disposed within the patient's venous system with the distal end of the catheter extending into the coronary sinus 21 (shown in FIG. 4) to deliver a fluid containing cardioplegic agents to the myocardium in a retrograde manner through the patient's coronary venous system to paralyze the entire myocardium.

The elongated occluding catheter 10 extends through the descending aorta to the left femoral artery 23 and out of the patient through a cut down 24. The proximal extremity 25 of the catheter 10 which extends out of the patient is provided with a multi-arm adapter 26 with one arm 27 adapted to receive an inflation device 28. The adapter 26 is also provided with a second arm 30 with main access port 31 through which passes instruments, a valve prosthesis, an angioscope, or to direct blood, irrigation fluid, cardioplegic agents and the like to or from the system. A third arm 32 is provided for monitoring aortic root infusion pressure at the distal end of the catheter and/or for directing blood, irrigation fluid, and the like to or from the system. In the system configuration of FIG. 1, the third arm 32 of the multi-arm adapter 26 is connected to a cardioplumonary bypass line 33 to vent the patient's heart, particularly the left ventricle, and to recover the blood removed and return it to the patient via the cardiopulmonary bypass system. A suitable valve 34 is provided to open and close the bypass line 33 and direct the fluid passing through the bypass line to a discharge line 35 or a line 36 to a blood filter and recovery unit 37. A return line may be provided to return any filtered blood to the cardiopulmonary bypass system 18 or other blood conservation system.

Figure 3:
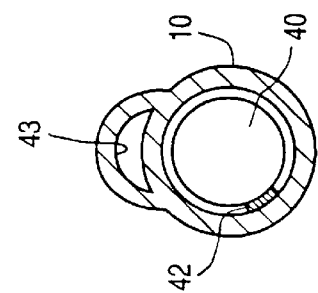
FIG. 3 is a transverse cross-sectional view of the occluding catheter shown in FIG. 2 taken along the lines 3—3.
Figure 2:
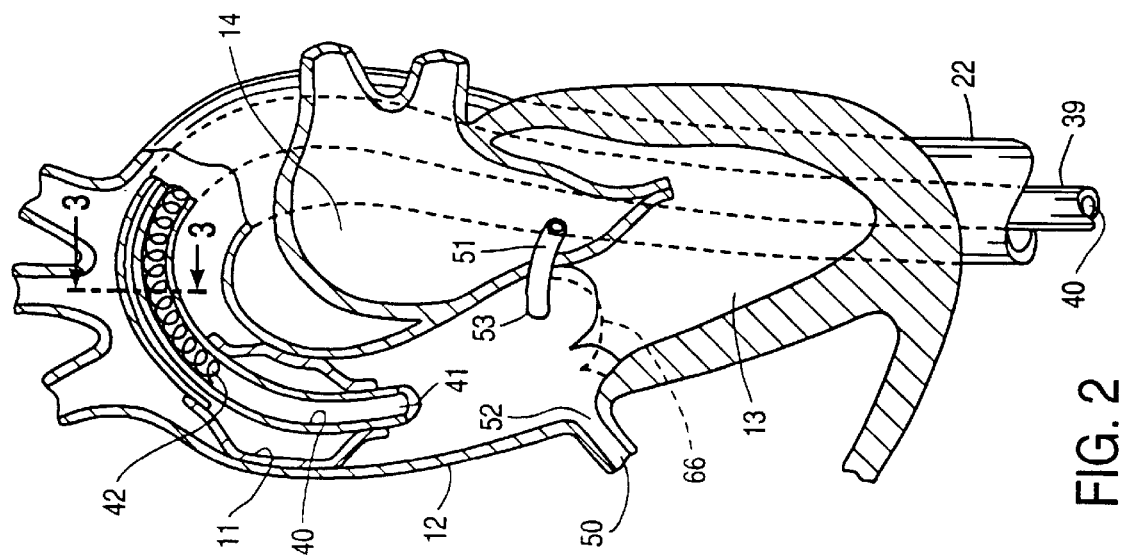
FIG. 2 is a schematic partly cut-away representation of a patient's heart with the endoaortic partitioning catheter of the present invention placed within the ascending aorta.

The details of the aortic occlusion catheter 10 and the disposition of the distal extremity thereof within the aorta are best illustrated in FIGS. 2 and 3. As indicated, the catheter 10 includes an elongated catheter shaft 39 which has a first inner lumen 40 for infusion of a cardioplegic agent in fluid communication with the main access port 31 in the second arm of the adapter 26. Additionally, the infusion lumen 40 may be adapted to facilitate the passage of instruments, a valve prosthesis, an angioscope, irrigation fluid, and the like therethrough and out the distal port 41 in the distal end thereof. A supporting coil 42 may be provided in the distal portion of the first inner lumen 40 to prevent the catheter shaft 39 from kinking when it straightened for initial introduction into the arterial system or when it is advanced through the aortic arch. The shaft 39 is also provided with a second inner lumen 43 which is in fluid communication with the interior of the occluding balloon 11.

Figure 4:
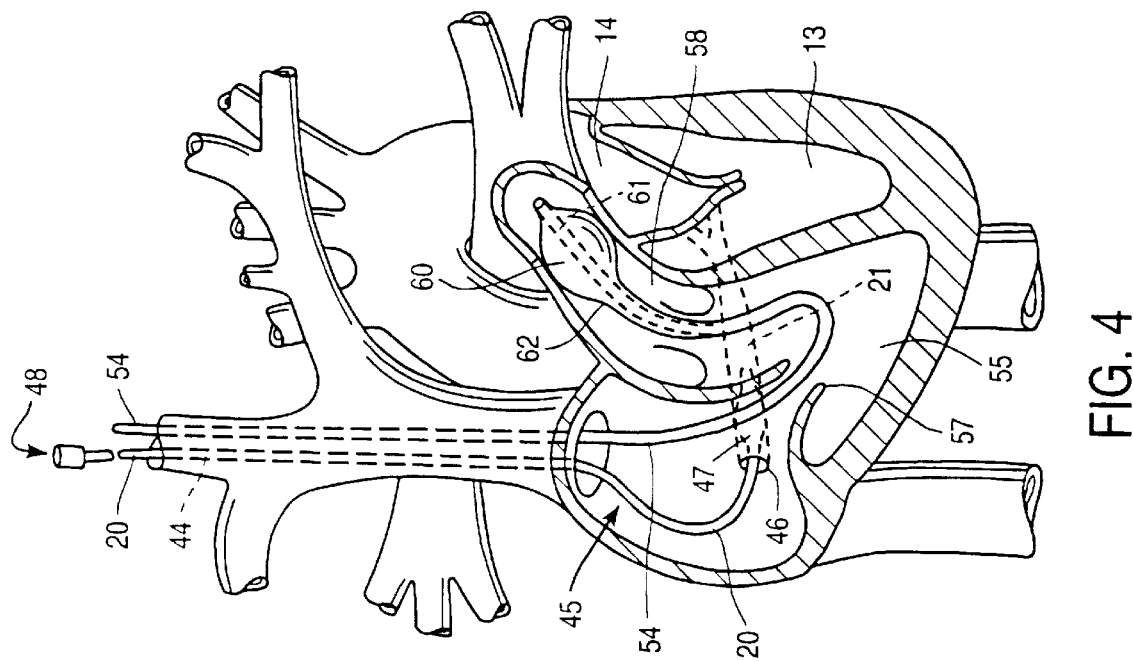
FIG. 4. is an enlarged view, partially in section, of the retrograde cardioplegia delivery catheter and the pulmonary venting catheter shown in FIG. 1.

In one embodiment of the system, a retrograde cardioplegia balloon catheter 20, which is shown in more detail in FIG. 4, is introduced into the patient's venous system through the right internal jugular vein 44 and is advanced through the right atrium 45 and into the coronary sinus 21 through the coronary sinus discharge opening 46 in the right atrium. The retrograde catheter 20 is provided with a balloon 47 on a distal portion of the catheter 20 which is adapted to occlude the coronary sinus 21 when inflated. A liquid containing a cardioplegic agent, e.g. an aqueous KCl solution, is introduced into the proximal end 48 of the catheter 20, which extends outside of the patient, under sufficient pressure so that the fluid containing the cardioplegic agent can be forced to pass through the coronary sinus 21, through the capillary beds (not shown) in the patient's myocardium, through the coronary arteries 50 and 51 and ostia 52 and 53 associated with the respective coronary arteries into the blocked off portion of the ascending aorta 12 as shown.

A pulmonary venting catheter 54 is also shown in FIG. 4 disposed within the right internal jugular vein 44 and extending through the right atrium 45 and right ventricle 55 into the pulmonary trunk 56. The catheter 54 passes through tricuspid valve 57 and pulmonary valve 58. An inflatable occluding balloon 60 may be provided as shown on a distal portion of the pulmonary venting catheter 54 which is inflated to occlude the pulmonary trunk 56 as shown. The pulmonary venting catheter 54 has a first inner lumen 61 which extends from the distal end of the catheter to the proximal end of the catheter which vents fluid from the pulmonary trunk 56 to outside the patient's body either for discharge or for passage to the blood recovery unit and thereby decompresses the left atrium 14 through the pulmonary capillary beds (not shown). The catheter 54 has a second inner lumen 62 which is adapted to direct inflation fluid to the interior of the inflatable balloon 60.

To set up the cardiac access system, the patient is initially placed under light general anesthesia. The withdrawal catheter 17 and the return catheter 19 of the cardiopulmonary bypass system 18 are percutaneously introduced into the right femoral vein 16 and the right femoral artery 15, respectively. An incision 24 is also made in the left groin to expose the left femoral artery 23 and the aortic occluding catheter 10 is inserted into the left femoral artery through an incision therein and advanced upstream until the balloon 11 on the distal end of the occluding catheter 10 is properly positioned in the ascending aorta 12. Note that bypass could similarly be established in the left groin and the aortic occlusion catheter put into the right femoral artery. The retrograde perfusion catheter 20 is percutaneously inserted by a suitable means such as the Seldinger technique into the right internal jugular vein 44 or the subclavian vein and advanced into the right atrium 45 and guided through the discharge opening 46 into the coronary sinus.

The pulmonary venting catheter 54 is advanced through the right internal jugular vein 44 or the subclavian vein (whichever is available after introduction of retrograde perfusion catheter 20) into the right atrium 45, right ventricle 55, and into the pulmonary trunk 56. The occluding balloon 60 may be inflated if necessary by inflation with fluid passing through the lumen 62 to block the pulmonary trunk 56 and vent blood therein through the lumen 61 where it is discharged through the proximal end of the catheter which extends outside of the patient. Alternatively, the occluding balloon 60 may be partially inflated with air or $CO_2$ during introduction for flow-assisted placement. The venting of the pulmonary trunk 56 results in the decompressing of the left atrium 14 and, in turn, the left ventricle. In the alternative, the venting catheter 54 may be provided with means on the exterior thereof, such as expanded coils as described in U.S.

Pat. No. 4,889,137 (Kolobow), which hold open the tricuspid and pulmonary valves and perform the same function of decompressing the left atrium. See also the article written by F. Rossi et. al. in the Journal of Thoracic Cardiovascular Surgery, 1900;100:914–921, entitled "Long-Term Cardiopulmonary Bypass By Peripheral Cannulation In A Model Of Total Heart Failure", which is incorporated herein in its entirety by reference.

The operation of the cardiopulmonary bypass unit 18 is initiated to withdraw blood from the femoral vein 16 through catheter 17, remove $CO_2$ from and add oxygen to the withdrawn blood and then pump the oxygenated blood through the return catheter 19 to the right femoral artery 15. The balloon 11 may then be inflated to occlude the ascending aorta 12, causing the blood pumped out of the left ventricle (until the heart stops beating due to the cardioplegic fluid as discussed hereinafter) to flow through the discharge port 41 into the first inner lumen 40 of the occluding catheter. The blood flows through the inner lumen 40 and out the third arm 32 of the adapter 26 into the bypass line 33 and then into the blood filter and blood recovery unit 37 through the valve 34 and line 36. For blood and irrigation fluids containing debris and the like, the position of the valve 34 may be changed to direct the fluid through the discharge line 35.

In a first embodiment of the method, a liquid containing a cardioplegic agent such as KCl is directed through the infusion lumen 40 of the catheter 10 into the aortic root 12 and subsequently into the coronary arteries 52, 53 to paralyze the patient's myocardium. Alternatively, if a retroperfusion catheter 20 is provided for delivery of the cardioplegic agent, the balloon 47 on the distal extremity of the catheter 20 is inflated to occlude the coronary sinus 21 to prevent fluid loss through the discharge opening 46 into the right atrium 45. A liquid containing a cardioplegic agent such as KCl is directed through the catheter 20 into the coronary sinus 21 and the pressure of the cardioplegic fluid within the coronary sinus 21 is maintained sufficiently high, (e. g. 40 mm Hg) so that the cardioplegic fluid will pass through the coronary veins, crossing the capillary beds to the coronary arteries 50 and 51 and out the ostia 52 and 53. The cardioplegic fluid pressure within the coronary sinus 21 should be maintained below 75 mm Hg to avoid pressure damage to the coronary sinus 21. Once the cardioplegic fluid passes through the capillary beds in the myocardium, the heart very quickly stops beating. At that point the myocardium is paralyzed and has very little demand for oxygen and can be maintained in this state for long periods of time with minimal damage.

With the cardiopulmonary bypass system in operation, the heart completely paralyzed and not pumping, the left atrium and ventricle decompressed and the ascending aorta blocked by the inflated balloon 11 on the occluding catheter 10, the heart is appropriately prepared for a cardiac procedure.

Inflation of the inflatable member 11 on the distal end of the delivery catheter 10 fixes the distal end of the occluding catheter 10 within the ascending aorta 12 and isolates the left ventricle 13 and the upstream portion of the ascending aorta from the rest of the arterial system downstream from the inflatable member. The passage of any debris or emboli, solid or gaseous, generated during a cardiovascular procedure to regions downstream from the site would be precluded by the inflated balloon 11. Fluid containing debris or emboli can be removed from the region between the aortic valve and the occluding balloon 11 through the inner lumen 40 of catheter 10. A clear, compatible fluid, e.g. an aqueous based fluid such as saline delivered through the inner lumen 40 or the cardioplegic fluid discharging from the coronary ostia 52 and 53, may be maintained in the region wherein the cardiovascular procedure is to be performed to facilitate use of an angioscope or other imaging means that allows for direct observation of the cardiac procedure. Preferably, the fluid pressure in the left ventricle 13 is maintained sufficiently higher than that in the left atrium to prevent blood from the left atrium from seeping into the left ventricle and interfering with the observation of the procedure.

Figure 5A:
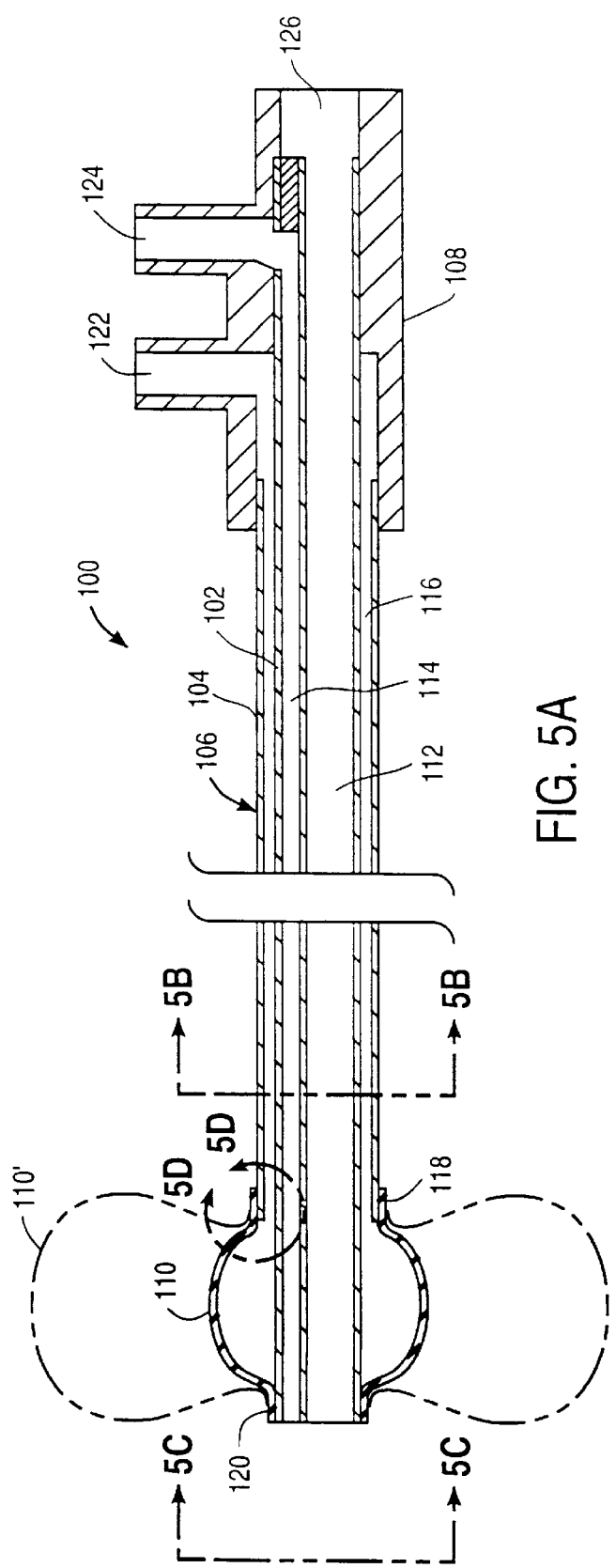
FIG. 5A is a longitudinal cross section of a first embodiment of the endoaortic partitioning catheter of the present invention.

FIG. 5A shows a longitudinal cross section of a first preferred embodiment of the endoaortic partitioning catheter 100 of the present invention. The endoaortic partitioning catheter 100 of FIG. 5A is made with a coaxial construction, which indicates that the catheter 100 is constructed of a first, inner tube 102 within a second, outer tube 104. The inner tube 102 and the outer tube 104 of the catheter 100 combine to form an elongated shaft 106 that runs from a proximal hub 108 to the distal end of the catheter 100 having an aortic occlusion balloon 110 mounted thereon. The length of the shaft 106 is such that the catheter 100 can be introduced into the patient's aorta by way of an arterial cutdown or the Seldinger technique into a peripheral artery, such as the femoral or brachial artery, and advanced into the ascending aorta. For introduction by way of a femoral artery or iliac artery the length of the shaft 106 is preferably 80 to 125 cm. For introduction by way of a brachial artery, the carotid artery or through a penetration directly into the aorta, the length of the shaft 106 is preferably 20 to 80 cm.

Figure 5D:
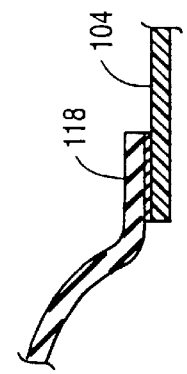
FIG. 5D is a detail drawing showing the construction of section 5D—5D of the catheter of FIG. 5A.
Figure 5C:
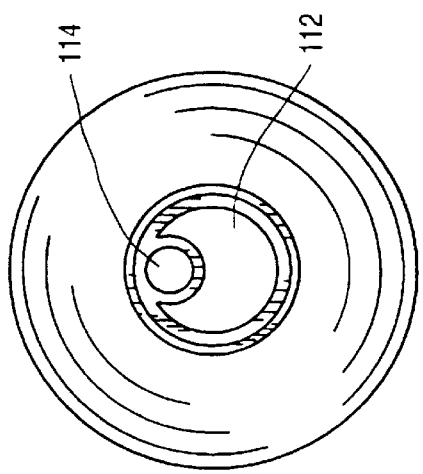
FIG. 5C is a lateral cross section of the catheter of FIG. 5A taken along the lines 5C—5C.
Figure 5B:
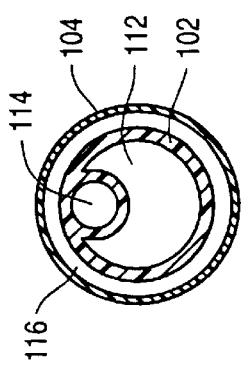
FIG. 5B is a lateral cross section of the catheter of FIG. 5A taken along the lines 5B—5B.

In the embodiment of FIG. 5A, the inner tube 102 of the catheter 100 is a two lumen tube, having a crescent-shaped cardioplegia infusion lumen 112 which wraps around a circular distal pressure lumen 114, as shown in cross section in FIGS. 5B and 5C. The cardioplegia infusion lumen 112 and the distal pressure lumen 114 are open at the distal end of the catheter 100. The cardioplegia infusion lumen 112 preferably has a cross sectional area sufficient for delivering a mixture of warm or cooled, oxygenated blood and cardioplegia solution at a rate of from about 200 ml/min to 400 ml/min with an infusion pressure not to exceed 300 mmHg. In one presently preferred embodiment, the cross sectional area of the cardioplegia infusion lumen 112 is approximately 5.74 $mm^2$ (0.00889 $in^2$) for a catheter with a length of about 120–130 cm. The cross sectional area of the cardioplegia infusion lumen 112 necessary to deliver the desired flow rate will vary somewhat depending on the length of the catheter shaft 106 and the ratio of blood to cardioplegic solution in the mixture. The distal pressure lumen 114 preferably has a cross sectional area sufficient to transmit the pressure within the aortic root along the length of the catheter shaft 106 without excessive damping of the pressure wave. In a preferred embodiment having a shaft length of about 120–130 cm, a distal pressure lumen 114 having an internal diameter of 0.61 mm, and therefore a cross sectional area of 0.29 $mm^2$ (0.00045 $in^2$), provides the desired pressure signal transmission.

The outer tube 104 of the catheter 100 fits coaxially around the inner tube 102 with an annular space between the two tubes providing a balloon inflation lumen 116, as shown in cross section in FIG. 3C. The external diameter of the catheter 100 can be made within the range of 8–23 French (Charrière scale), preferably in the range of 8–12 French. In one preferred embodiment of the catheter 100, the outer tube 104 has an external diameter of 3.4–3.5 mm or approximately 10.5 French (Charrière scale). In a second preferred embodiment of the catheter 100, the outer tube 104 has an external diameter of 3.2–3.3 mm or approximately 10 French (Charrière scale). An aortic occlusion balloon 110 is mounted on the distal end of the catheter 100. The aortic occlusion balloon 110 has a proximal balloon neck 118 which is sealingly attached to the outer tube 104 and a distal balloon neck 120 which is sealingly attached to the inner tube 102 of the catheter 100 so that the balloon inflation lumen 116 communicates with the interior of the balloon 110. Preferably, the balloon inflation lumen 116 has a cross sectional area of approximately 0.5–1.0 mm² (0.00077–0.00155 in²) to allow rapid inflation and deflation of the aortic occlusion balloon 110. In a particular presently preferred embodiment with the described configuration, the balloon inflation lumen 116 has a cross sectional area of approximately 0.626 mm² (0.00097 in²) which allows the occlusion balloon 110 be inflated to a recommended maximum volume of 40 cc with saline solution or saline solution mixed with a radiopaque contrast agent at an inflation pressure of 35 psi in 40 seconds or less, preferably in 20 seconds or less. Whether inflating by hand or using a mechanical inflation device, the inflation of the balloon is preferably volume-limited so that, although the transient, peak inflation pressure reaches approximately 35 psi, the inlation pressure decreases to about 10–12 psi to maintain balloon inflation when the balloon reaches its desired inflation volume. The balloon inflation lumen 116 also allows the occlusion balloon 110 be deflated in 60 seconds or less, preferably in 40 seconds or less. The occlusion balloon 110 can be inflated and deflated by hand using an ordinary syringe or it can be inflated and deflated using an inflation device which provides a mechanical advantage or that is powered by compressed air or an electric motor.

FIG. 5D is a detail drawing showing the construction of section 5D—5D of the catheter 100 of FIG. 5A. The proximal balloon neck 118 is bonded to the distal end of the outer tube 104 in a lap joint. The bond between the proximal balloon neck 118 and the outer tube 104 and the bond between the distal balloon neck 120 and the inner tube 102 can be formed by adhesive bonding, by solvent bonding or by heat bonding depending on the materials chosen for each component. Alternatively, the outer tube 104 can be formed from a single continuous extrusion with the material of the aortic occlusion balloon 110.

The proximal hub 108 of the catheter 100 has a luer fitting balloon inflation port 122 that is sealingly connected to the balloon inflation lumen 116, a luer fitting pressure monitoring port 124 that is sealingly connected to the distal pressure lumen 114, and an infusion port 126 that is sealingly connected to the cardioplegia infusion lumen 112. The proximal hub 108 may be joined to the proximal ends of the inner tube 102 and the outer tube 104 by adhesive bonding, by insert molding or by other known processes.

In the embodiment of FIG. 5A, the aortic occlusion balloon 110 is shown as having a generally spherical geometry in the unexpanded state 110, as well as a generally spherical geometry in the expanded or inflated state 110'. Other possible geometries for the balloon in the unexpanded state 110 include cylindrical, oval or football-shaped, eccentric or other shaped balloons. Some of these variations are further described below. In this preferred embodiment the balloon 110 is made of an elastomeric material that expands elastically from the uninflated to the inflated state. Preferred materials for the balloon 110 include latex, silicone, and polyurethane, chosen for their elasticity, strength and biocompatibility for short term contact with the blood and body tissues.

Figure 6A:
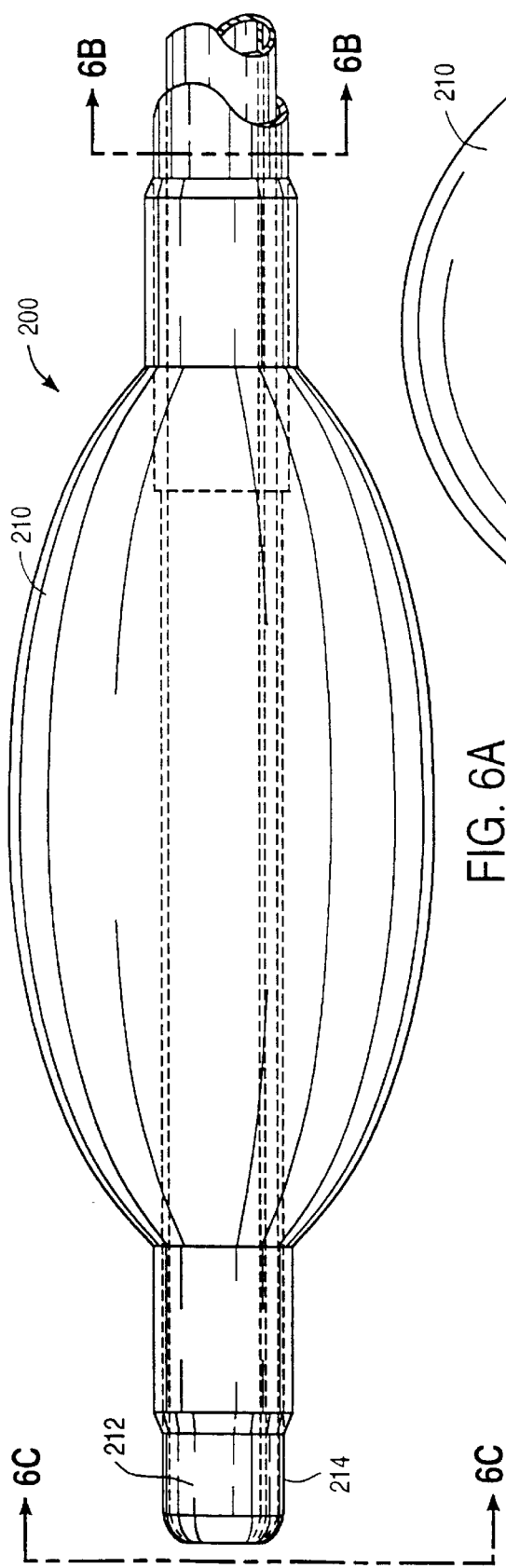
FIG. 6A is a lateral side view of a second embodiment of the endoaortic partitioning catheter.

FIG. 6A shows a lateral side view of a second preferred embodiment of the endoaortic partitioning catheter 200. In this embodiment the inner tube 202 has been made with a D-shaped cardioplegia infusion lumen 212 and a D-shaped distal pressure lumen 214. The choice of D-shaped lumens in the inner tube 202, makes it possible to maximize the diametrical clearance within the cardioplegia infusion lumen 212 for a given cross sectional area, as compared to the crescent-shaped cardioplegia infusion lumen 112 of FIG. 5C. This variation of the catheter 200 may be preferable when catheters or other instruments are to be introduced to the heart and its associated blood vessels through the cardioplegia infusion lumen 212.

As shown in FIG. 6A, the occlusion balloon 210 of this embodiment has an ellipsoidal or football-shaped deflated profile which is imparted by the balloon molding process. The wall thickness of the molded balloon 210 in its deflated state is typically about 0.090–0.130 mm. Typically, the deflated balloon 210 has a diameter of approximately 12 mm before it is folded, although deflated balloon diameters of 3 to 20 mm are possible. The inflated balloon 210' assumes a roughly spherical shape with a maximum diameter of approximately 40 mm when inflated. The football shape of the molded balloon has been shown to be advantageous in that the deflated balloon 210 has a deflated profile which is less bulky and smoother than for other balloon geometries tested. This allows the deflated balloon 210 to be folded and more easily inserted through a percutaneous puncture into the femoral artery or through an introducer sheath or a dual function arterial cannula and introducer sheath. In this embodiment as well, the balloon 210 is preferably made of an elastomeric material such as latex, silicone, or polyurethane. In one particular embodiment, the football-shaped balloon has an internal geometry determined by a positive dip molding mandrel with a radius of curvature in the central portion of the balloon of approximately 1.0 inch with a maximum diameter in the center of the balloon of about 0.5 inch. The curvature of the central portion of the balloon has a smoothly radiused transition, for example with a radius of about 0.25 inch, to the proximal and distal balloon sleeves, which are sized to fit snugly onto the exterior of the chosen diameter catheter shaft.

FIG. 7A shows a longitudinal cross section of a third preferred embodiment of the endoaortic partitioning catheter 300. The catheter 300 of this embodiment has a coaxial construction having a single lumen inner tube 302 surrounded by a single lumen outer tube 304. The single lumen inner tube 302 has a circular cardioplegia infusion lumen 312 that is connected on its proximal end to the infusion port 326 of the proximal hub 308 of the catheter 300. The cardioplegia infusion lumen 312 is open at the distal end of the catheter 300. The single lumen outer tube 304 of the catheter 300 fits coaxially around the inner tube 302 with an annular space between the two tubes providing a balloon inflation lumen 316. The balloon inflation lumen 316 is connected on its proximal end to the balloon inflation port 322 of the proximal hub 308.

In this embodiment, the aortic root pressure monitoring function is fulfilled by a distal pressure transducer 330 mounted at the distal tip 332 of the catheter 300. The distal pressure transducer 330 electronically monitors the aortic root pressure and transmits a signal along signal wires 334 and 336 to electrical connections 338 and 340 within an electrical connector 324 on the proximal hub 308 of the catheter 300. The electrical connector is adapted to be connected to an electronic pressure monitor which displays an analog or digital indication of the pressure at the distal end 332 of the catheter 300. The distal pressure transducer 330 is preferably a piezoelectric pressure transducer which creates a voltage signal indicative of the external fluid pressure exerted on the transducer 330. Examples of piezoelectric materials suitable for construction of the distal pressure transducer 330 include piezoelectric polymers such as polyvinylidene bifluoride or Kynar™ (Elf Atochem SA), or piezoelectric ceramics such as lead barium titanate, zirconium barium titanate or other commercially available piezoelectric materials. The geometry of the distal pressure transducer 330 may be a ring encircling the distal tip 332 of the catheter 300, as shown in FIGS. 7A and 7B. Alternatively, a small patch of the piezoelectric material may be mounted on one side of the distal tip 332 of the catheter 300. The distal pressure transducer 330 preferably has a pressure sensing range from about −75 to 300 mmHg or greater (−1.5 to 5.7 psi) so as to be able to measure root pressure during cardioplegia infusion and during venting of the aortic root.

Optionally, a balloon pressure monitoring transducer 350 may also be mounted within the balloon 310 of the catheter 300 for monitoring the inflation pressure of the balloon 310. The balloon pressure monitoring transducer 350 electronically monitors the balloon inflation pressure and transmits a signal along signal wires 352 and 354 to electrical connections 356 and 358 within the electrical connector 324 on the proximal hub 308 of the catheter 300. The balloon pressure monitoring transducer 350 is preferably a piezoelectric pressure transducer which creates a voltage signal indicative of the external fluid pressure exerted on the transducer 350, made for example from one the piezoelectric polymers or piezoelectric ceramics designated above in connection with the distal pressure transducer 330. The balloon pressure monitoring transducer 350 preferably has a pressure sensing range from about −760 to 300 mmHg or greater (−15 to 35 psi) so as to be able to measure balloon pressure during inflation and deflation of the occlusion balloon 310. The balloon pressure monitoring transducer 350 can be used to monitor internal balloon pressure to make sure that the occlusion balloon 310 has been inflated to proper pressure to insure reliable occlusion of the ascending aorta. The balloon pressure monitoring transducer 350 can also be used to determine when the occlusion balloon 310 has contacted the interior wall of the ascending aorta by monitoring for a spike in the inflation pressure within the balloon or for an inflection point in the pressure/volume curve while inflating. A safe inflation volume can be determined for each individual patient by a protocol wherein the occlusion balloon 310 is inflated until it contacts the interior wall of the ascending aorta, then a set volume of inflation fluid is added to create a reliable seal to occlude the aortic lumen. Alternatively, the protocol for inflation could include determining when the occlusion balloon 310 contacts the aortic wall and incrementally increasing the pressure a set amount to form a seal.

The signal wires 334, 336 from the distal pressure transducer 330 and the signal wires 352, 354 from the balloon pressure monitoring transducer 350 may extend through the annular inflation lumen 316 between the inner tube 302 and the outer tube 304. The signal wires 334, 336, 352, 354 may be laid loosely in the inflation lumen 316 with some slack, or they may be spiraled around the inner tube 302, so that they do not adversely affect the bending characteristics of the catheter 300. Alternatively, the signal wires 334, 336, 352, 354 may be embedded in the wall of the inner tube 302, either during the extrusion process or in a post-extrusion operation. In order to have electrical impedance to match the impedance of the transducers 330, 350 and/or the electronic pressure monitor, the signal wires 334, 336, 352, 354 may be provided as parallel pairs, twisted pairs or coaxial cables, as required.

The use of a distal pressure transducer 330 for monitoring aortic root pressure eliminates the need for a separate pressure monitoring lumen in the catheter as provided in the embodiments of FIGS. 5A and 6A. This allows a reduction in the catheter external diameter without sacrificing catheter performance in terms of the cardioplegia flow rate in the infusion lumen 312 and the speed of balloon inflation and deflation through the balloon inflation lumen 316. A 10 French (3.3 mm external diameter) catheter constructed according to this design provides a flow rate and balloon inflation performance comparable to a 10.5 French (3.5 mm external diameter) catheter constructed with a separate pressure monitoring lumen. Reducing the external diameter of the catheter in this way has a number of clinical advantages. The smaller diameter catheter will be easier to introduce into a patient's femoral, brachial or other artery by either the Seldinger technique or by an arterial cutdown or by insertion through an introducer sheath. It will also be possible to introduce the smaller diameter catheter into smaller arteries, as encountered in smaller patients, particularly female and pediatric patients. This will increase the clinical applicability of the catheter and the method for its use to a greater patient population. In all patients, the smaller diameter catheter will cause less trauma to the artery it is introduced through, thereby reducing the likelihood of complications, such as bleeding or hematoma at the arterial access site. The smaller diameter catheter will also be particularly advantageous when used in conjunction with the dual function arterial cannula and introducer sheath described below in relation to FIGS. 31–34 because the smaller diameter shaft will occupy less of the blood flow lumen of the cannula, allowing higher blood flow rates at lower pressures. With these improvements, the external diameter of an endoaortic partitioning catheter for use with warm blood cardioplegia can be reduced to 8 to 10 French (2.7–3.3 mm external diameter) and for use with crystalloid cardioplegia can be reduced to 7 to 9 French (2.3–3.0 mm external diameter).

Further improvements in reducing the effective diameter of the catheter during introduction or removal of the catheter from the peripheral arterial access site can be accomplished by making the occlusion balloon self-collapsing around the catheter. Two embodiments of coaxial-construction catheters with self-collapsing occlusion balloons are shown in FIGS. 8A–8C and 9A–9B.

Figure 8A:
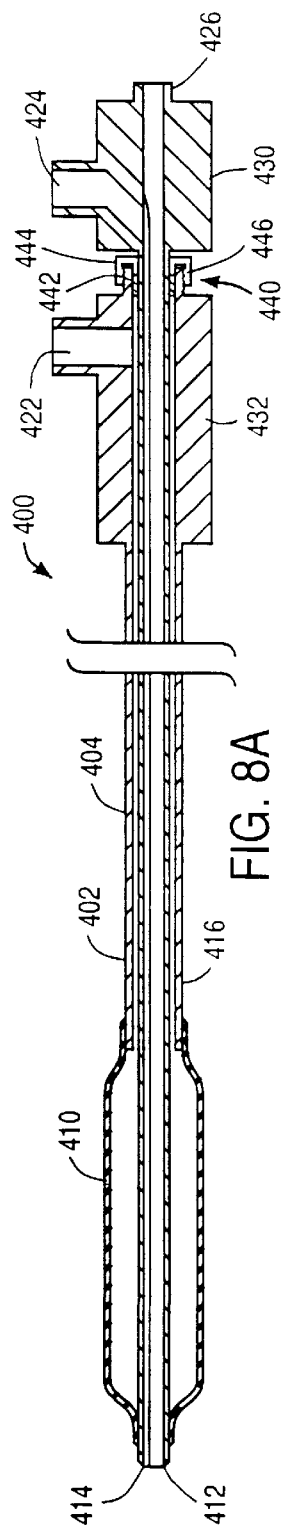
FIG. 8A is a longitudinal cross section of a fourth embodiment of the endoaortic partitioning catheter having a variable length occlusion balloon with the occlusion balloon deflated.
Figure 8B:
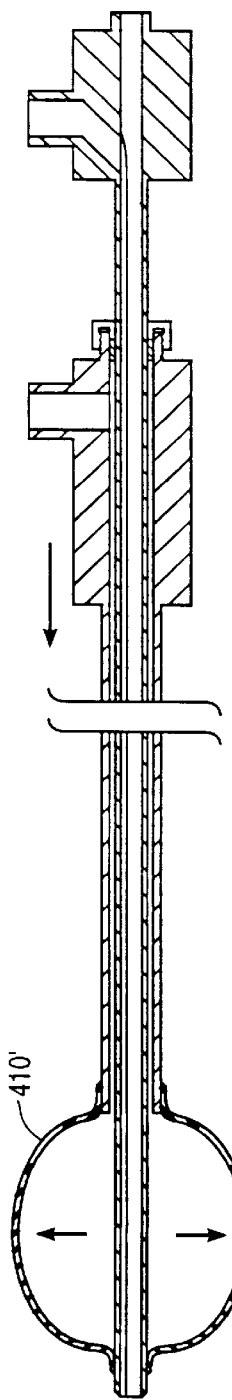
FIG. 8B is a longitudinal cross section of the catheter of FIG. 8A with the occlusion balloon inflated in an elongated position.
Figure 8C:
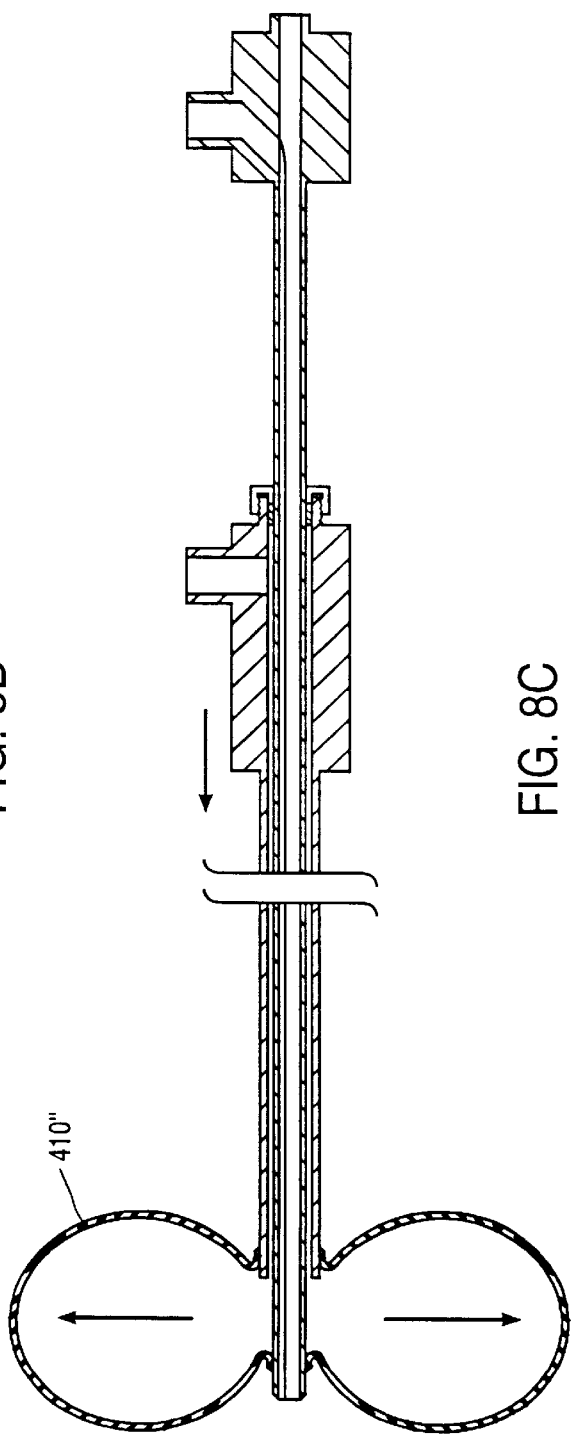
FIG. 8C is a longitudinal cross section of the catheter of FIG. 8A with the occlusion balloon inflated in a shortened position.

FIG. 8A shows a transverse cross section of a coaxial-construction endoaortic partitioning catheter 400 in which the inner tube 402 and the outer tube 404 are axially movable with respect to one another. The inner tube 402 has a cardioplegia infusion lumen 412 and a pressure monitoring lumen 414. The inner tube 402 is connected to a first proximal hub 430 with luer fitting connections 426 and 424 in communication with the cardioplegia infusion lumen 412 and the pressure monitoring lumen 414, respectively. The outer tube 404 fits coaxially around the inner tube 402 with an annular space between the two tubes providing a balloon inflation lumen 416. The outer tube 404 is connected to a second proximal hub 432 with a luer fitting connection 422 for the balloon inflation lumen 416. The inner tube 402 passes through the second proximal hub 432 exiting through a sliding fluid seal 440 that allows axial movement of the inner tube 402 with respect to the second proximal hub 432 and the outer tube 404.

In one preferred embodiment the sliding fluid seal 440 is a type of compression fitting known in the industry as a Tuohy-Borst adapter. The Tuohy-Borst adapter 440 has a compressible tubular or ring-shaped elastomeric seal 442 that fits within a bore 446 on the proximal end of the second proximal hub 432. A threaded compression cap 444 fits onto the proximal end of the second proximal hub 432. When the compression cap 444 is tightened, it compresses the elastomeric seal 442 axially, which causes the lumen 448 of the seal 442 to narrow and seal against the inner tube 402. The Tuohy-Borst adapter 440 can also be used to lock the position of the inner tube 402 with respect to the second proximal hub 432 and the outer tube 404 by tightening the compression cap 444 until the friction between the elastomeric seal 442 and inner tube 402 effectively locks them together to prevent axial movement between the two.

Figure 8D:
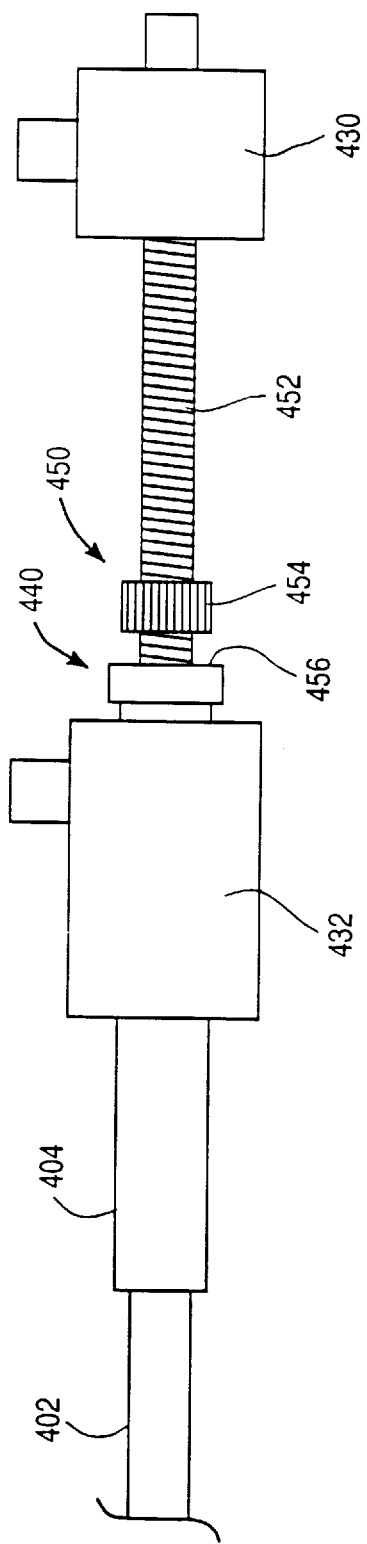
FIG. 8D shows the proximal end of an alternate embodiment of the catheter of FIG. 8A.

In a second preferred embodiment, shown in FIG. 8D, a sliding fluid seal 440 is combined with a locking mechanism 450 to lock the inner tube 402 with respect to the outer tube 404 to prevent axial movement between the two. The locking mechanism 450 may comprise a threaded shaft 452 in alignment with the inner tube 402 and a lock nut 454 threaded onto the shaft 452. By turning the lock nut 454 on the threaded shaft 452, the user can adjust the position of the inner tube 402 relative to the outer tube 404 to increase or decrease the length of the occlusion balloon 410 when inflated. The sliding fluid seal 440 may be a Tuohy-Borst adapter as described above or, because a separate locking mechanism 450 is provided, it may be a simple sliding seal, such as an O-ring or wiper seal 456, as illustrated.

Figure 6C:
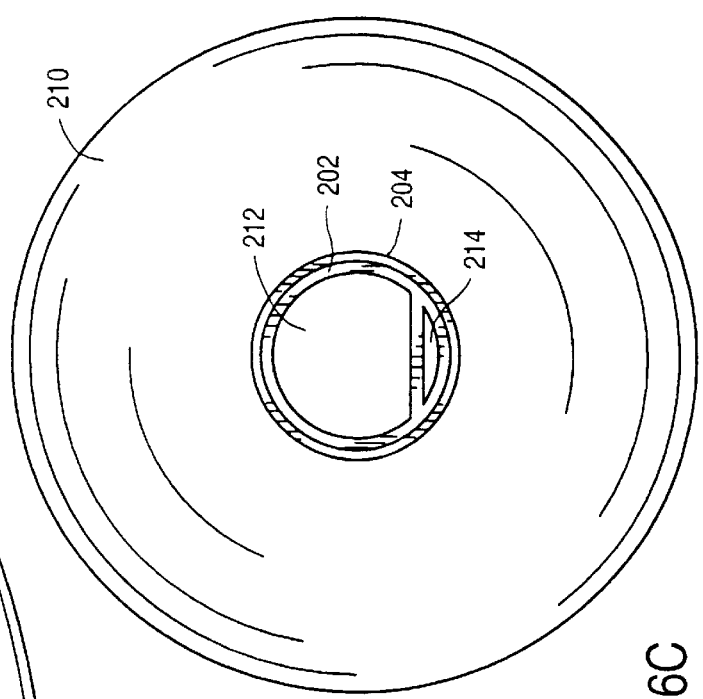
FIG. 6C is a lateral cross section of the catheter of FIG. 6A taken along the lines 6C—6C.
Figure 6B:
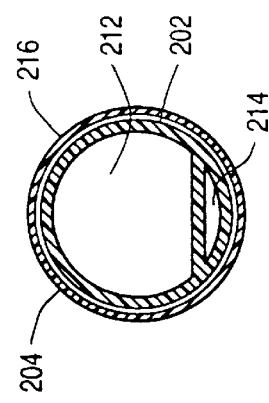
FIG. 6B is a lateral cross section of the catheter of FIG. 6A taken along the lines 6B—6B.

When the balloon 410 is deflated the inner tube 402 can be moved to its furthest distal position and locked with respect to the outer tube 404, as shown in FIG. 6A. This stretches the wall of the occlusion balloon 410 collapsing the deflated balloon tightly around the inner tube 402 to reduce the deflated profile for easy introduction through the peripheral arterial access site or through an introducer sheath. Once the occlusion balloon 410 has been advanced to the desired location in the ascending aorta, the locking mechanism 440 can be released so that the balloon 410 can be inflated. FIG. 6B shows the endoaortic partitioning catheter 400 of FIG. 1A with the inner tube 402 in an intermediate position with respect to the outer tube 404 and the occlusion balloon 410' inflated. In this position, the inner tube 402 and the outer tube 404 keeps a tension on the ends of the occlusion balloon 410' which elongates the balloon somewhat in the axial direction. This results in the balloon 410' having a somewhat oblong inflated profile which is smaller in diameter and longer axially than the typical spherical shape of a freely inflated balloon. FIG. 6C shows the endoaortic partitioning catheter 400 of FIGS. 1A and 1B with the inner tube 402 in its farther proximal position with respect to the outer tube 404 and the occlusion balloon 410" inflated. In this position, the inner tube 402 and the outer tube 404 places a compressive force on the ends of the occlusion balloon 410" which restricts the expansion of the balloon somewhat in the axial direction. This results in the balloon 410" having an inflated profile which achieves the full diameter of a freely inflated balloon diameter, but is somewhat shorter in the axial direction. This feature allows the user to select the inflated diameter of the balloon and the axial length of the balloon, and therefore the length of contact with the aortic wall, within certain ranges, as well as allowing the balloon to be more fully collapsed when deflated for insertion and removal. The range of useful balloon diameters of the occlusion balloon 410 for use in an adult human ascending aorta is from above 20 to 40 cm. Other ranges of balloon diameters may be needed for pediatric patients or nonhuman subjects.

This feature will find particular utility when the endoaortic partitioning catheter 400 is used while performing surgery or other interventional procedures on the aortic valve, or within the aortic root or ascending aorta. To facilitate the surgery, it will be important to provide as much clearance as possible between the inflated occlusion balloon 410" and the aortic valve to allow manipulation of instruments within the ascending aorta while at the same time being sure that the occlusion balloon 410" does not occlude the brachiocephalic artery. In this case, the inner tube 402 would be adjusted to its farthest proximal position with respect to the outer tube 404 before the occlusion balloon 410" is inflated in order to restrict the size of the balloon 410" as much as possible in the axial direction.

FIG. 9A shows a transverse cross section of a coaxial-construction endoaortic partitioning catheter 500 in which the inner tube 502 and the outer tube 504 are rotatable with respect to one another. The inner tube 502 has a cardioplegia infusion lumen 512 connected to a luer fitting connection 526 on the proximal hub 508. The outer tube 504 fits coaxially around the inner tube 502 with an annular space between the two tubes providing a balloon inflation lumen 516 which communicates with a luer fitting connection 522 on the proximal hub 508. The outer tube 504 is connected to a rotating collar 540 which is rotatably and slidably mounted on the distal end of the proximal hub 508. There is an O-ring seal 542 or other type of fluid tight seal between the rotating collar 540 and the proximal hub 508. An aortic occlusion balloon 510 is mounted on the distal end of the catheter 500 with the proximal balloon neck 518 sealingly attached to the outer tube 504 and the distal balloon neck 520 sealingly attached to the inner tube 502 of the catheter 500 so that the balloon inflation lumen 516 communicates with the interior of the balloon 510. The occlusion balloon 510 is preferably made of an elastomeric material, such as latex, silicone or polyurethane. A piezoelectric distal pressure transducer 530 mounted at the distal tip of the catheter 500 electronically monitors the aortic root pressure and transmits a signal along signal wires 532 and 534 to electrical connections 536 and 538 within an electrical connector 524 on the proximal hub 508 of the catheter 500.

In order to collapse the occlusion balloon 510 to its lowest possible deflated profile for introduction or withdrawal of the catheter 500 through a peripheral arterial access site or through an introducer sheath, the rotating collar 540 can be rotated with respect to the proximal hub 508 to twist the deflated occlusion balloon 510 around the inner tube 502. In addition, the rotating collar 540 can also be moved proximally with respect to the proximal hub 508 to tension the balloon to create an even lower deflated profile. After the catheter has been introduced and maneuvered to the desired position, the rotating collar 540 is counter rotated to release the balloon from its twisted state before inflation. The catheter 500 with the fully inflated occlusion balloon 510' is shown in FIG. 9B. When the catheter is to be withdrawn after use, the occlusion balloon 510 is deflated and the rotating collar 540 is again rotated and moved proximally with respect to the proximal hub 508 to twist the deflated occlusion balloon 510 around the inner tube 502 to create a lower deflated profile for removal of the catheter 500.

In each of the previously described embodiments, the shaft of the catheter, whether it has a coaxial construction or a multilumen construction, may take one of a variety of forms. In the simplest form, the shaft of the catheter may be a straight length of flexible tubing, made from a highly flexible plastic or elastomer, such as polyurethane, polyethylene, polyvinylchloride or a polyamide polyether block copolymer, preferably in the range of 35 to 72 Shore D durometer. Another variation of this embodiment would be to provide a straight shaft with zones of varying stiffness graduated from a stiff proximal section to a highly flexible distal section. The variable stiffness shaft could be made by welding tubing segments of different stiffness polymers end-to-end to create two, three or more zones of stiffness. In one illustrative embodiment, the catheter shaft could be made with a stiff proximal section of a polyamide polyether block copolymer with a hardness of 63 to 72 Shore D durometer, an intermediate section of a softer grade of the same polymer with a hardness of 55 to 63 Shore D durometer, and a distal section of a very soft grade of the polymer with a hardness of 35 to 55 Shore D durometer. In addition, an especially flexible soft tip with a hardness of 25 to 35 Shore D durometer may be molded or heat bonded to the distal end of the catheter shaft. Alternatively, the shaft can be made with continuously graduated stiffness from the proximal to distal end using a process such as total intermittent extrusion to gradually change the stiffness along the length of the catheter shaft. In a coaxial-construction catheter either or both of the inner tube and the outer tube may be made with varying stiffness to achieve the overall effect of a graduated stiffness catheter. Furthermore, either or both of the inner tube and the outer tube may be reinforced with wire or filament braiding or coils for increased stiffness, torque control or kink resistance.

The polymeric material of the shaft is preferably loaded with a radiopaque filler, such as bismuth subcarbonate, bismuth oxychloride, bismuth trioxide, barium sulfate or another radiopaque material. The shaft is preferably loaded with a level of between about 10 and 30 percent of radiopaque filler by weight, preferably about 20%. The soft tip may be loaded with a higher percent of radiopaque filler, such as about 30 to 35 percent by weight for greater fluoroscopic visibility. Instead of or in addition to the radiopaque filler, radiopaque markers, for example rings of gold, platinum, tin, tantalum or tungsten alloys may be attached to the catheter shaft at various points along the length, especially at the tip of the catheter for fluoroscopic visibility.

In such an embodiment, the highly flexible catheter would be advanced through the patient's descending aorta and into the ascending aorta with a stiffer guidewire and/and or a dilator placed in the infusion lumen of the catheter to provide stiffness for advancing and maneuvering the catheter into position. With the varying stiffness embodiment, the stiffness of the proximal shaft segment will assist in advancing and maneuvering the catheter into position. If desired, a curved guidewire or dilator may be used to assist in forming the catheter shaft to the curve of the aortic arch. Once the catheter is in position, the balloon would be inflated to occlude the ascending aorta and the guidewire or dilator withdrawn to free the infusion lumen for infusing cardioplegic fluid.

In another approach, the catheter shaft may be made of a somewhat stiffer polymer so that the distal segment of the catheter can be precurved to a configuration that assists in maneuvering the occlusion balloon into the correct position within the ascending aorta. As with the straight catheter shaft previously described, the precurved catheter shaft may also be made with varying degrees of stiffness graduated from a stiff proximal segment to a flexible distal segment. The shaft would be made of slightly higher durometer grades of a flexible plastic or elastomer, such as polyurethane, polyethylene, polyvinylchloride or a polyamide polyether block copolymer, preferably in the range of 55 to 72 Shore D durometer. A short, very flexible tip of a low durometer polymer, preferably in the range of 25 to 35 Shore D durometer, can be added to the distal end to make it less traumatic to the arterial walls and the aortic valve which it may come in contact with. Two variations of precurved catheter shafts are shown in FIGS. 10A–10C and 11A–11C. For the purposes of illustration, these embodiments are shown as built in a multilumen construction, but the precurved shafts can as well be made in one of the coaxial constructions previously described.

One preferred embodiment of an aortic partitioning catheter 600 with a precurved shaft is shown in FIG. 11A. In this embodiment the distal portion 604 of the catheter shaft 602 is configured to facilitate placement of the occlusion balloon 610 into the ascending aorta. The curve of the catheter shaft 602 also stabilizes the catheter in the proper position to prevent migration or dislodgement of the inflated occlusion balloon. The distal portion 604 of the catheter shaft 602 has a curve of approximately 270–300 degrees of arc. The curve of the catheter shaft 602 is a compound curve having a first segment 606 of approximately 135° of arc with a radius of curvature of approximately 75–95 mm. Contiguous with the first segment is a second segment 608 of approximately 135° of arc with a tighter radius of curvature of approximately 40–50 mm. Continuing from the second segment is a third segment 612 of approximately 25–50 mm in length adjacent to the distal end 614 of the catheter. The occlusion balloon 610 is mounted on the third segment 612 of the catheter shaft near the distal end 614 of the catheter 600. The third segment 612 of the catheter 600 may be straight, so that the total arc subtended by the catheter curve 604 is approximately 270°. Alternatively, the third segment 612 of the catheter 600 may be angled upward at a point about midway along the third segment 612, as shown in FIG. 10A, creating a total arc of curvature of about 300°. The upward angle of the third segment 612 helps the catheter 600 to follow a dilator or guidewire as it passes over the curve of the aortic arch during catheter introduction. The angle of the third segment 612 also helps to prevent the distal tip 614 of the catheter 600 from contacting the interior wall of the aorta as it passes over the aortic arch thereby reducing the likelihood of irritating or damaging the aortic wall or of dislodging calculi or other sources of potential emboli. The curve of the catheter is generally coplanar, as shown in the side view in FIG. 10B. The specifics of this catheter curve are given as an illustrative example of one preferred embodiment. The precise angles and lengths of the curve may be varied according to the geometry of the patient's anatomy based on fluoroscopic observation of the aortic arch.

A cross section of the catheter shaft is shown in FIG. 10C. The catheter shaft 602 is made from a multilumen extrusion of a flexible plastic or elastomer, such as polyurethane, polyethylene, polyvinylchloride or a polyamide polyether block copolymer, preferably in the range of 55 to 72 Shore D durometer. In one preferred embodiment, the multilumen catheter shaft 602 has a cardioplegia infusion lumen 616, a distal pressure monitoring lumen 618, and a balloon inflation lumen 620. The balloon inflation lumen 620 is in fluid communication with the interior of the inflatable occlusion balloon 610. The infusion lumen 616 and the distal pressure monitoring lumen 618 each connect with separate ports at or near the distal tip 614 of the catheter 600, distal to the occlusion balloon 610. For use with blood/cardioplegia techniques, the catheter shaft 602 preferably has an external diameter of 3.5 to 4 mm or 10.5 to 12 French (Charrière scale). For use with crystaloid cardioplegia techniques, the catheter shaft 602 may be made smaller, with an external diameter of 3.3 mm or 10 French (Charrière scale) or smaller.

Figure 11:
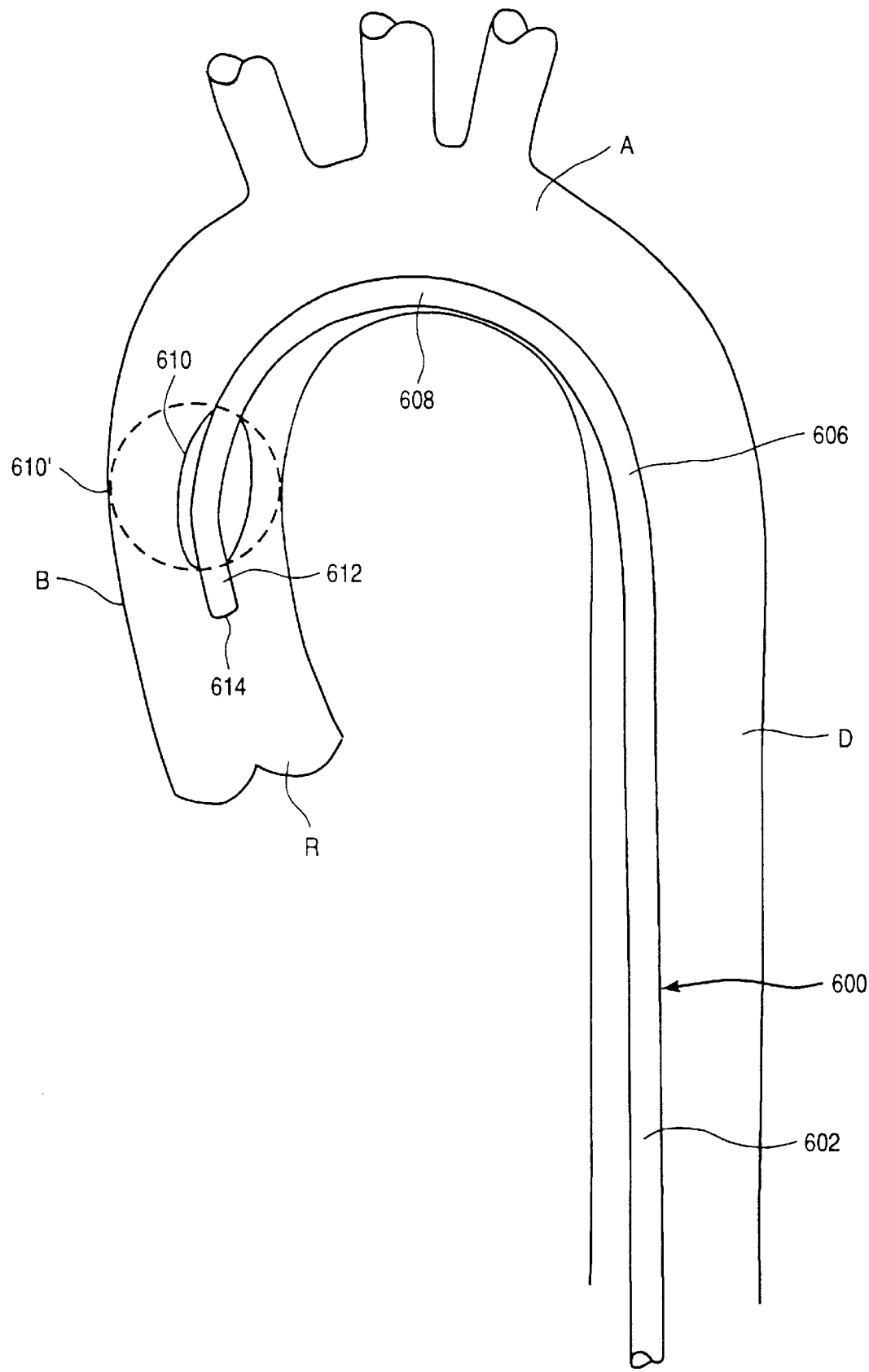
FIG. 11 is a schematic partly cut-away representation of a patient's aortic arch with the endoaortic partitioning catheter of FIG. 10A positioned in the ascending aorta.

FIG. 11 is a schematic partly cut-away representation of a patient's aortic arch A with the endoaortic partitioning catheter 600 of FIG. 10A positioned in the ascending aorta B. In use, the distal curve 604 in the catheter shaft 602 of FIG. 10A is initially straightened out by inserting a guidewire and a dilator (not shown) into the infusion lumen 616 of the catheter 600 to facilitate insertion of the catheter 600 into a peripheral arterial access site such as the femoral artery. The catheter 600 is advanced until the distal end 614 of the catheter 600 is at the apex of the aortic arch A. Then, the dilator is withdrawn as the catheter 600 is advanced over the aortic arch A to allow the curved distal portion 604 of the catheter 600 to resume its curve within the ascending aorta B. When the catheter 600 is in proper position in the ascending aorta B, the second segment 608 of the curved shaft conforms to the aortic arch A to hold the distal tip 614 of the catheter centered just above the aortic root R. The first curved segment 606 of the catheter shaft resides in the descending aorta D, somewhat straightened by its contact with the aortic walls. If the patient has a relatively straight ascending aorta B, as observed fluoroscopically, a straight third segment 612 of the curved shaft is preferred for proper centering of the catheter tip 614 when the occlusion balloon 610' is inflated. If the ascending aorta B is curved, a curved or angled distal segment 612, such as the one illustrated in FIG. 10A, is preferred.

Another preferred embodiment of an aortic partitioning catheter 650 with a precurved shaft is shown in FIG. 12A. In this embodiment also the distal portion 654 of the catheter shaft 652 is configured to facilitate placement of the occlusion balloon 660 into the ascending aorta and to stabilize the catheter in the proper position to prevent migration or dislodgement of the inflated occlusion balloon 660', but with a slightly different geometry to accommodate variations in the patient's anatomy. The distal portion 654 of the catheter shaft 652 has an approximately elliptical curve which subtends approximately 270–300 degrees of arc. The minor axis 646 of the ellipse is parallel to the shaft 652 of the catheter and has a length of about 50 to 65 mm. The major axis 648 of the ellipse is perpendicular to the shaft 652 of the catheter and has a length of about 55 to 70 mm. The elliptical curve can also be viewed as having a first segment 656 with a larger radius of curvature, a second segment 658 with smaller radius of curvature and a third segment 662 on which the occlusion balloon 660 is mounted. The curved distal portion 654 of the catheter 650 is somewhat out of plane with the catheter shaft, angling or spiraling anteriorly from the plane of the catheter shaft by about 10°–20°, as shown in FIG. 12B. In one presently preferred embodiment, the distal tip 664 of the catheter 650 has an offset 672 from the plane of the catheter shaft 652 of approximately 14 mm. The offset 672 of the spiral curve helps to center the catheter tip 664 within the ascending aorta in patients in whom the ascending aorta is angled anteriorly. The preferred degree of offset 672 can vary significantly depending on patient anatomy, with an anticipated range of from 0 to 25 mm of offset 672 to accommodate most patients. Again, this catheter curve is given as an example of one preferred embodiment. The precise angles and lengths of the curve should be chosen according to the geometry of the patient's anatomy based on fluoroscopic observation of the aortic arch. Providing the catheters in a family of curves which are variations of the curves shown in FIGS. 10A and 12A, etc. will allow the user to select the proper catheter curve for the patient after observing the geometry of the aorta fluoroscopically.

A cross section of the catheter shaft is shown in FIG. 12C. The catheter shaft 652 is made from a multilumen extrusion of a flexible plastic or elastomer, such as polyurethane, polyethylene, polyvinylchloride or a polyamide polyether block copolymer, preferably in the range of 55 to 72 Shore D durometer. In this illustrative embodiment, the multilumen catheter shaft 652 has a cardioplegia infusion lumen 666, a distal pressure monitoring lumen 668, and a balloon inflation lumen 670. The balloon inflation lumen 670 is in fluid communication with the interior of the inflatable occlusion balloon 660. The infusion lumen 666 and the distal pressure monitoring lumen 668 each connect with separate ports at or near the distal tip of the catheter 664, distal to the occlusion balloon 660. The catheter shaft 652 can be made in a range of sizes, for instance with an external diameter of 3.5 to 4 mm or 10.5 to 12 French (Charrière scale) for use with blood/cardioplegia techniques, or with an external diameter of 3.3 mm or 10 French (Charrière scale) or smaller for use with crystaloid cardioplegia techniques.

Figure 13:
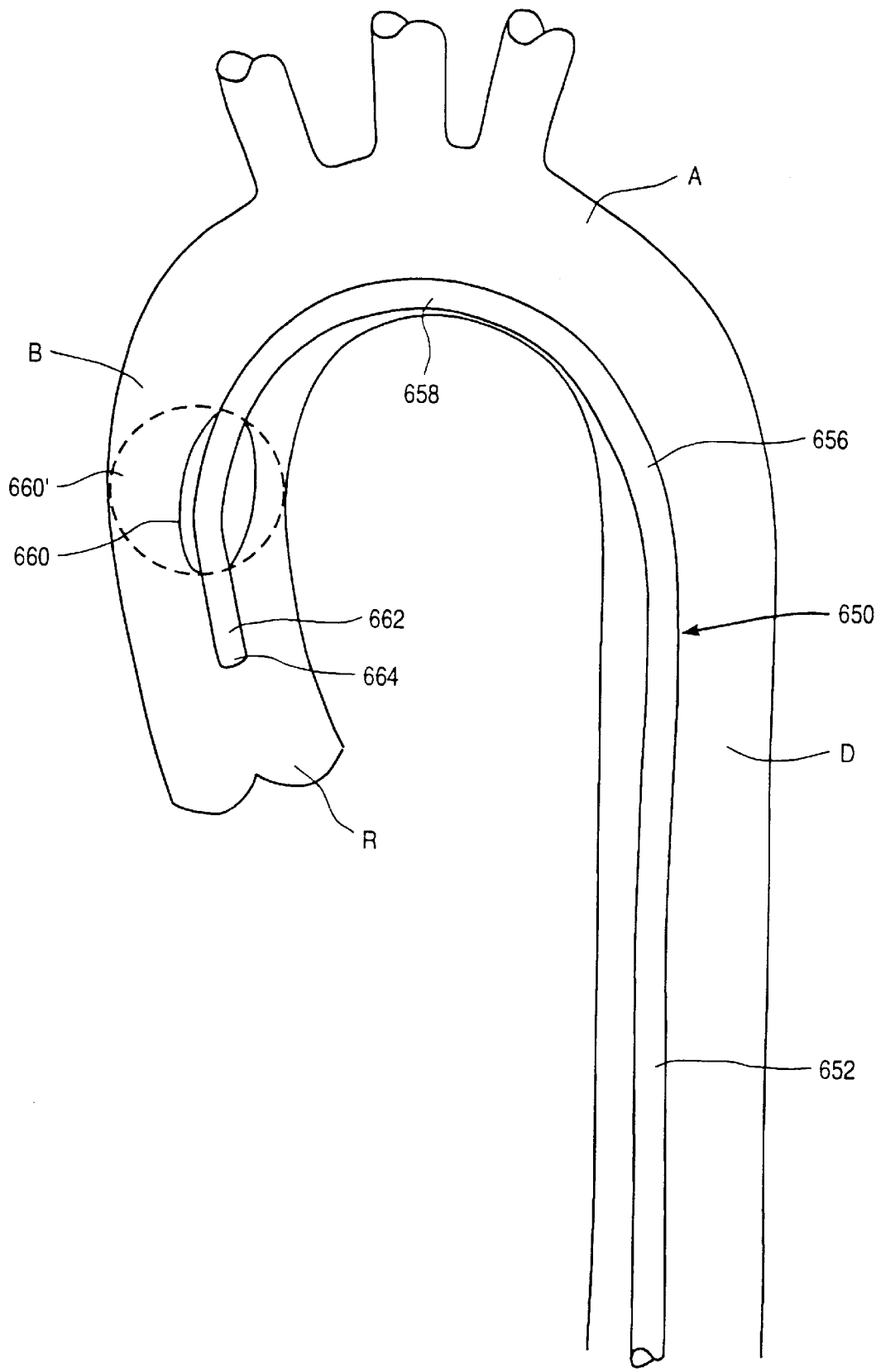
FIG. 13 is a schematic partly cut-away representation of a patient's aortic arch with the endoaortic partitioning catheter of FIG. 12A positioned in the ascending aorta.

FIG. 13 is a schematic partly cut-away representation of a patient's aortic arch A with the endoaortic partitioning catheter 650 of FIG. 12A positioned in the ascending aorta B. In use, a guidewire and a dilator (not shown) are inserted into the infusion lumen 666 to straighten out the distal curve 654 of the catheter 650. The catheter 650 is introduced into a peripheral arterial access site such as the femoral artery and advanced until the distal end 664 of the catheter 650 is at the apex of the aortic arch A. Then, the dilator is withdrawn as the catheter is advanced over the aortic arch A to allow the distal portion 652 of the catheter 650 to resume its curve within the ascending aorta B. When the catheter 650 is in proper position in the ascending aorta B, the second segment 658 of the curved shaft conforms to the aortic arch A to hold the distal tip 664 of the catheter centered just above the aortic root R. Due to its curvature, the second segment 658 of the catheter shaft tends to hug the inside curve of the aortic arch A which helps to prevent the catheter shaft from occluding or interfering with blood flow into the brachiocephalic artery or other arteries which have their takeoff from the aortic arch. The first curved segment 656 of the catheter shaft 652 resides in the descending aorta D, somewhat straightened by its contact with the aortic walls. The angled or spiral curve of the catheter shaft 652 assists in centering the distal tip 664 of the catheter 650 within the lumen of the ascending aorta B which is often angled anteriorly within the patient.

In order to reduce the external diameter of the catheter shaft in the embodiments of FIGS. 10A–10C and 12A–12C, particularly for use in conjunction with the dual purpose arterial cannula and introducer sheath described below in reference to FIGS. 31–34, while maintaining the maximum flow rate performance in the catheter, it is desirable to reduce the wall thickness of the multilumen extrusion as much as possible. In order to improve the kink resistance of the thin-walled catheter shaft in the precurved distal portion (604 in FIG. 10A, 654 in FIG. 12A) it has been found to be advantageous to dip coat the precurved distal portion with a soft, flexible polymer. For example a coating approximately 0.005–0.020 inches thick of a polyurethane with a hardness of 80 Shore A durometer on the precurved distal portion of the catheter shaft has been shown to significantly improve the kink resistance of the catheter shaft. If the coating is applied before mounting the polyurethane occlusion balloon on the catheter shaft, the coating also improves the heat bondability of the occlusion balloon to the shaft. Coating only the distal portion of the catheter shaft has the advantage that it does not increase the external diameter of the catheter shaft in the proximal portion which will reside within the blood flow lumen of the dual purpose arterial cannula and introducer sheath during perfusion. Since the proximal portion of the catheter shaft is not precurved and because it resides in the relatively straight descending aorta during use, it is not necessary to fortify the kink resistance of the shaft in this region.

One important function of the catheter curves shown in FIGS. 10A and 12A is for centering the tip of the catheter within the ascending aorta before and after the occlusion balloon is inflated to insure even distribution of the cardioplegic fluid to the coronary arteries when it is injected through the infusion lumen into the aortic root. In many cases, the compound curve of the catheter is needed to maintain the catheter tip within the center of the aortic lumen. It has been found that in some cases a simple 180° U-shaped curve results in off-center placement of the catheter tip despite the concentricity of the inflated balloon because of the curve of the ascending aorta. Another approach to centering the distal tip of the catheter within the lumen of the ascending is illustrated by the embodiment of the aortic partitioning catheter 700 shown in FIG. 14.

Figure 14:
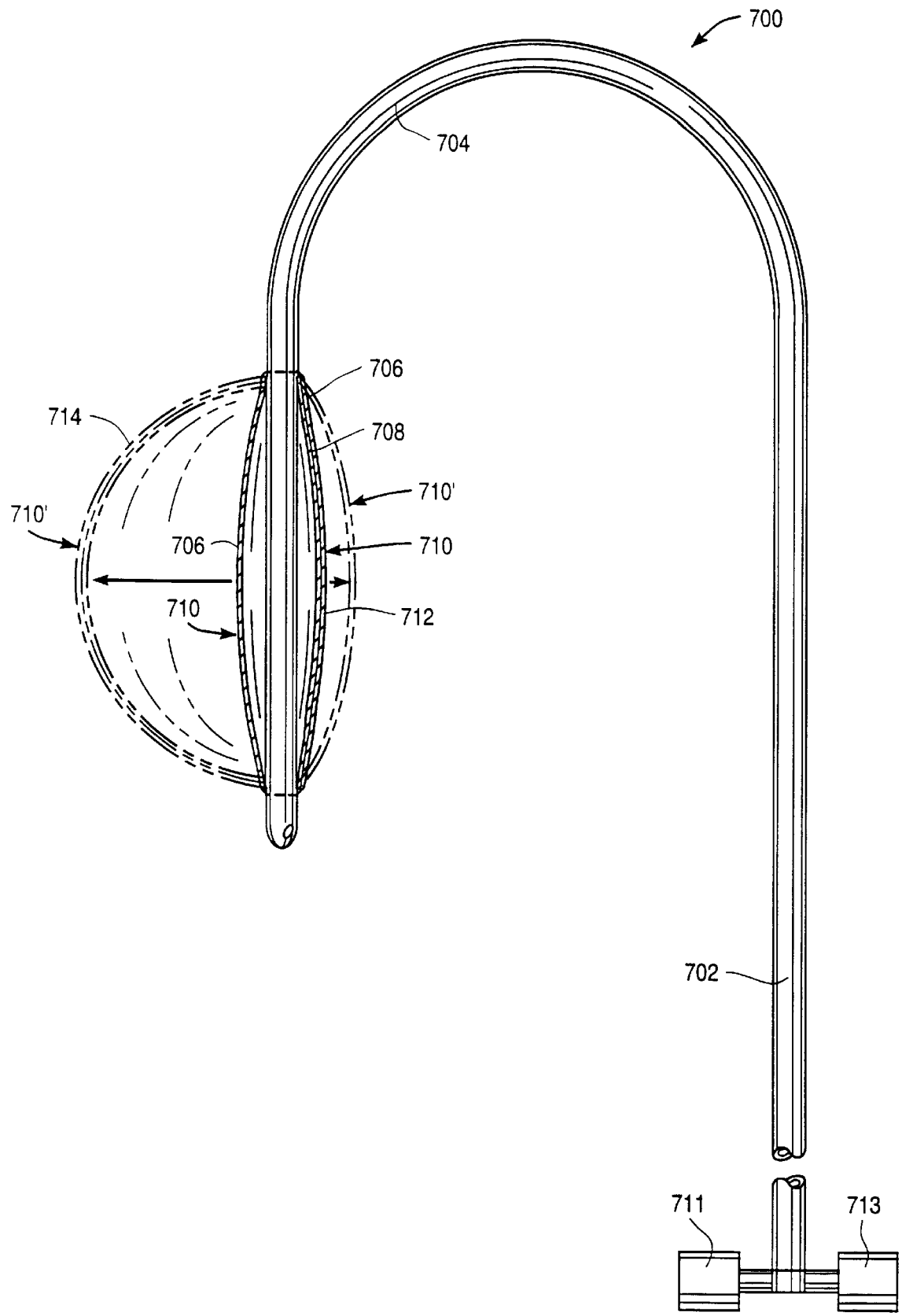
FIG. 14 is a front view of an eighth embodiment of the endoaortic partitioning catheter having an eccentric aortic occlusion balloon.

FIG. 14 is a front view of an embodiment of the endoaortic partitioning catheter 700 having an eccentric aortic occlusion balloon 710. The occlusion balloon has a symmetrical deflated profile, shown by solid lines 710. The asymmetrical inflated profile, shown by phantom lines 710', is achieved by molding the occlusion balloon with a thicker wall 712 on one side of the balloon 710. The thicker wall 712 of the balloon is oriented toward the inside of the distal curve 704 when mounted on the catheter shaft 702. When the occlusion balloon 710' is inflated, the thicker wall 712 resists expansion while the thinner wall 714 of the balloon more easily expands to its full potential, resulting in the intended eccentric inflated balloon profile 710'. One preferred method for manufacturing the occlusion balloon 710 of FIG. 14 is by a two-stage dip molding process. In the first stage of the process, a balloon mold, in the form of a dipping mandrel having the desired interior shape of the balloon, is oriented vertically and dipped into a solution or a suspension containing an elastomeric balloon material, such as polyurethane, silicone or latex. This creates a relatively even coating of the balloon material over the surface of the mandrel. This first coating 706 is then allowed to dry on the mandrel. Once the first coating 706 is dry, the orientation of the dipping mandrel is rotated to a horizontal position and one side of the balloon mandrel is dipped into the elastomer solution to create a second coating 708 of balloon material on one side of the balloon 710. The balloon mandrel is held in the horizontal orientation until the solvent evaporates from the elastomer solution. If the elastomer used to mold the balloon 710 is a thermoplastic elastomer, such as a thermoplastic polyurethane, the balloon can be removed from the dipping mandrel once it has dried. If the elastomer is a thermoset material, such as latex, silicone, or a thermoset polyurethane, further curing of the material may be required before the balloon 710 can be removed from the dipping mandrel. It should be noted that the second coating 708 on the balloon 710 may be made of a different material from the first coating 706. For instance, a stronger or less distensible material may be used for the second coating 708 to increase the resistance of the thicker wall 712 of the balloon 710 to inflation. It should also be noted that molding each coating of the balloon may require multiple iterations of the dipping and drying steps, depending on the composition and concentration of the polymer solution. For example, the currently preferred process for manufacturing polyurethane balloons typically requires about 6–8 iterations of the dipping and drying steps to make a finished balloon with a wall thickness of approximately 0.005–0.020 inches.

Figure 16:
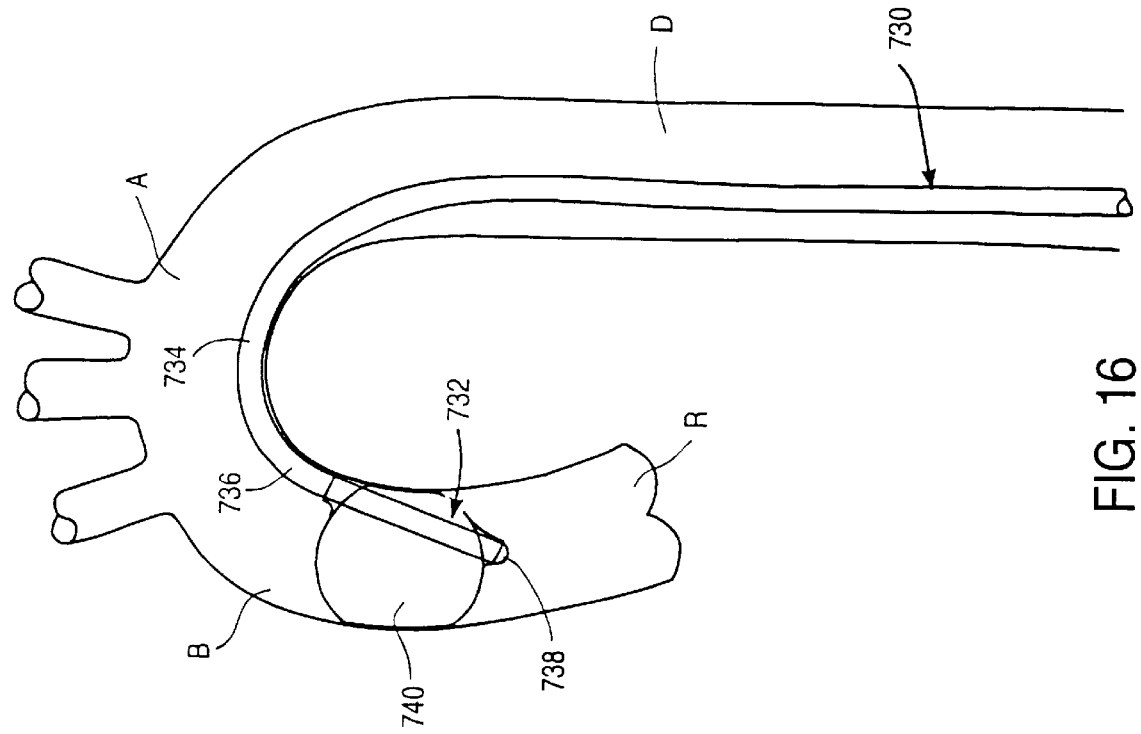
FIG. 16 is a schematic partly cut-away representation of a patient's aortic arch with an endoaortic partitioning catheter having an eccentric occlusion balloon positioned in the ascending aorta.
Figure 15:
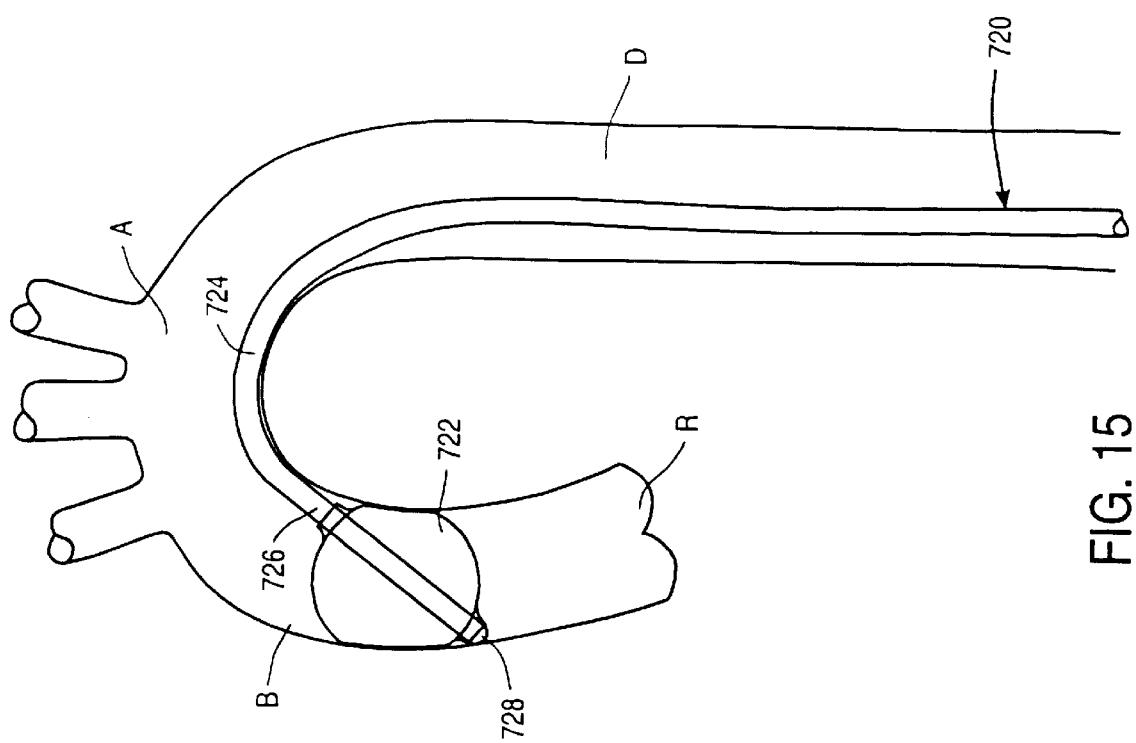
FIG. 15 is a schematic partly cut-away representation of a patient's aortic arch with an endoaortic partitioning catheter having a concentric occlusion balloon positioned in the ascending aorta.

FIGS. 15 and 16 illustrate how an eccentric balloon, like the eccentric occlusion balloon 710 of the catheter embodiment of FIG. 14, operates to center the tip of the aortic partitioning catheter within the ascending aorta of a patient.

FIG. 15 is a schematic partly cut-away representation of a patient's aortic arch A with an endoaortic partitioning catheter 720 having a concentric occlusion balloon 722 positioned in the ascending aorta B. The endoaortic partitioning catheter 720 has a 180° U-shaped catheter curve 724 with a concentric occlusion balloon 722 mounted on a straight distal portion 726 of the catheter 720. FIG. 15 shows the effect of placing the U-shaped catheter curve into a patient having a curved ascending aorta B. Note how, when the catheter 720 is pulled proximally to stabilize the catheter within the aortic arch A, the distal end 728 of the catheter is not centered in the aortic lumen despite the concentricity of the balloon 722 because of the mismatch between the catheter curve and the curve of the ascending aorta B.

FIG. 16 is a schematic partly cut-away representation of a patient's aortic arch A with an endoaortic partitioning catheter 730 having an eccentric occlusion balloon 732 positioned in the ascending aorta B. The aortic partitioning catheter 730 has a U-shaped distal curve 734 which subtends an arc of approximately 180°+/−45°. Mounted on a straight distal portion 736 of the catheter shaft is an occlusion balloon 732 which, when inflated, has an eccentric balloon profile with the larger portion 740 of the balloon facing the outside of the catheter curve 734 so that it will be oriented toward the right side of the patient. The eccentric inflated profile of the balloon 732 assists in centering the distal tip 738 of the catheter 730 within the aortic lumen when the ascending aorta B is curved. Note how the eccentric balloon 732 compensates for the mismatch between the catheter curve and the curve of the ascending aorta B to result in the distal tip 738 of the catheter 730 being well centered in the aortic lumen just above the aortic root R.

Figure 17:
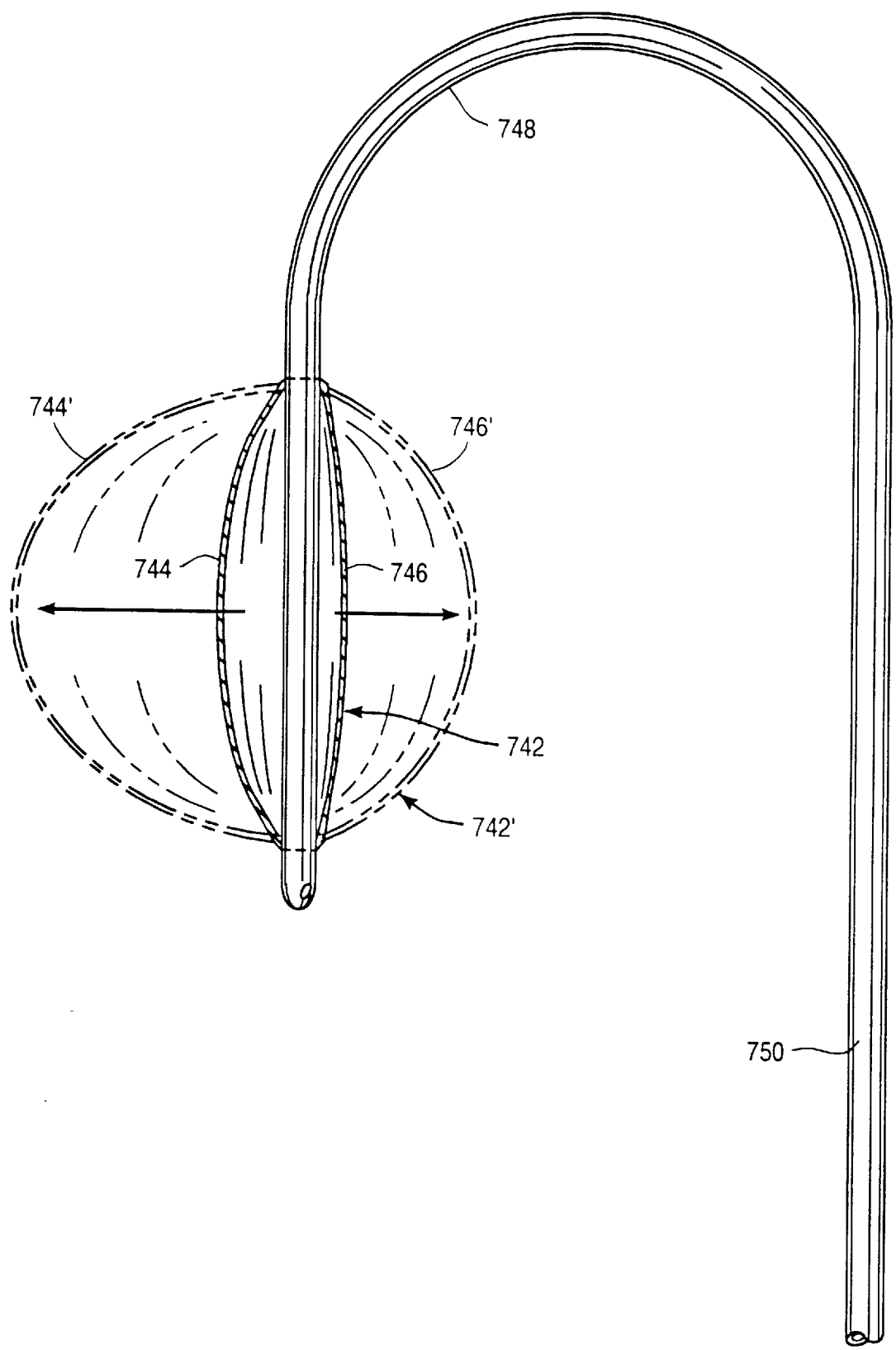
FIG. 17 is a front view of an ninth embodiment of the endoaortic partitioning catheter having an eccentric aortic occlusion balloon.

FIG. 17 shows an alternative construction for an occlusion balloon 742 with an eccentric inflated profile 742'. In this embodiment, the elastomeric balloon 742 is molded on a dipping mandrel which is machined with an asymmetrical profile. In contrast to the previous example, the molded balloon 742 has a uniform wall thickness, but it has an asymmetrical deflated profile with a larger side 744 and a smaller side 746. The balloon 742 is mounted on the catheter with the larger side 744 oriented toward the outside of the distal curve 748 of the catheter 750. When inflated, the larger side 744 of the balloon expands to a greater radius 744' than the smaller side 746', giving the intended eccentric inflated profile, as shown by phantom lines 742'.

Figure 18A:
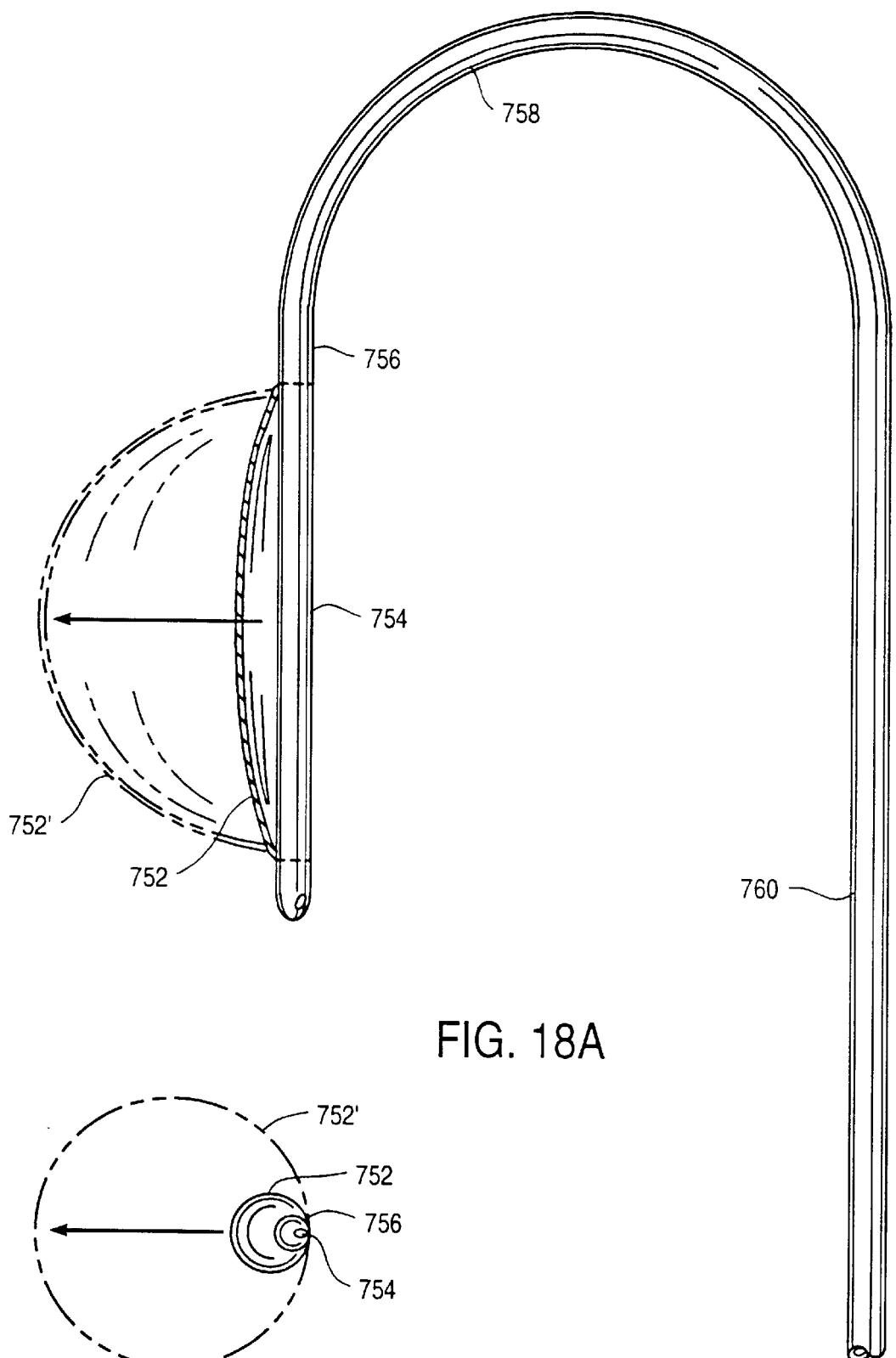
FIG. 18A is a front view of a tenth embodiment of the endoaortic partitioning catheter having an eccentric aortic occlusion balloon.
Figure 18B:
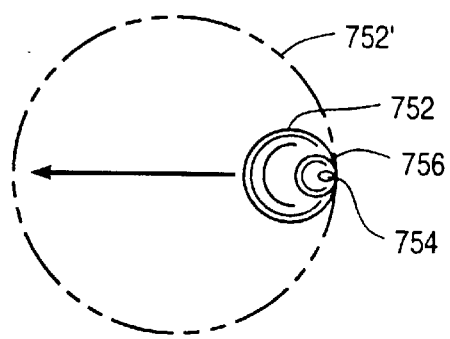
FIG. 18B is an end view of the catheter of FIG. 18A.

FIGS. 18A and 18B show another alternative construction for an occlusion balloon 752 with an eccentric inflated profile 752'. In this embodiment, the elastomeric occlusion balloon 752 is mounted on the catheter 760 in such a way that the side 754 of the balloon oriented toward the inside of the distal curve 758 of the catheter is bonded directly to the catheter shaft 756 along the length of the balloon 752 using a suitable adhesive. When the occlusion balloon 752 is inflated, only the side of the balloon oriented toward the outside of the distal curve 758 of the catheter shaft is allowed to expand, creating an eccentric inflated balloon profile, as shown by phantom lines 752'.

FIGS. 19A–19D and 20A–20D show alternative constructions of an eccentric occlusion balloon made of a nondistensible balloon material, such as polyethylene, polyethylene terephthalate polyester, polyester copolymers, polyamide or polyamide copolymers. Using a nondistensible balloon material such as these allows more precise control over the final shape and dimensions of the inflated occlusion balloon, as compared to the elastomeric balloons previously described. The nondistensible balloons can be thermoformed from tubing extruded from a nonelastomeric polymer, using known methods. Alternatively, the balloons can be dipped or rotomolded of a nonelastomeric polymer in solution. It is presently preferred to mold the inelastic balloon material using a hollow or negative mold of the exterior inflated balloon shape rather than a positive mold of the interior shape as used for the elastomeric balloons, because the molded inelastic balloons may be difficult to remove from a positive mold.

Figure 19A:
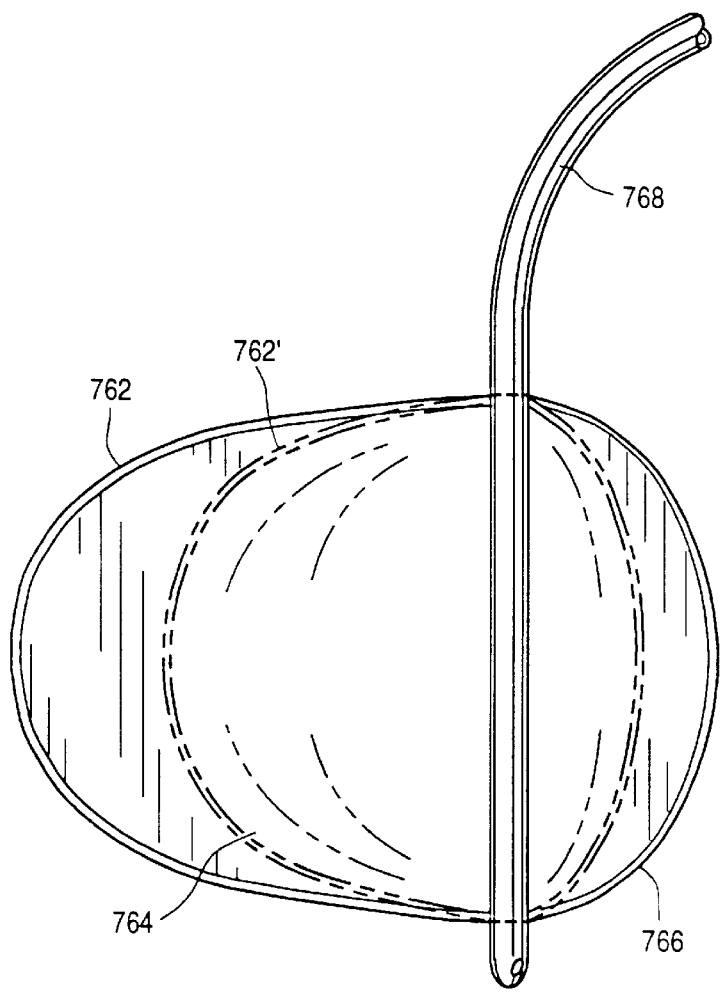
FIG. 19A is a front view of an eleventh embodiment of the endoaortic partitioning catheter having a nondistensible aortic occlusion balloon.
Figure 19C:
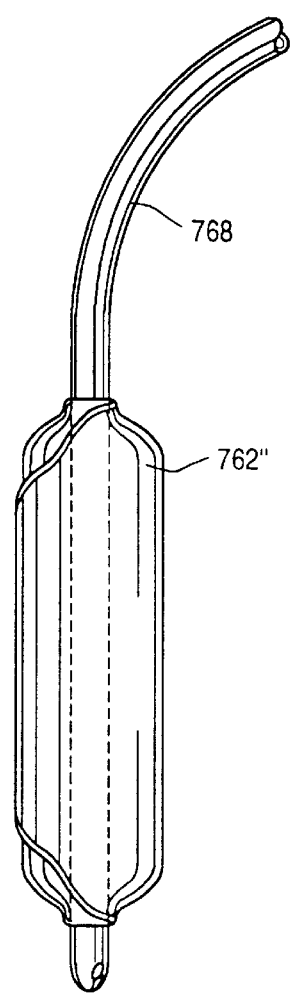
FIG. 19C is a side view of the catheter of FIG. 19A with the occlusion balloon wrapped around the catheter shaft.
Figure 19B:
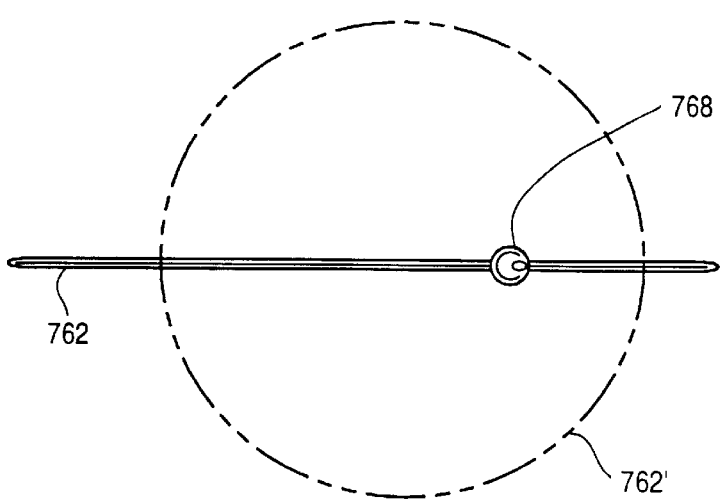
FIG. 19B is an end view of the catheter of FIG. 19A.
Figure 19D:
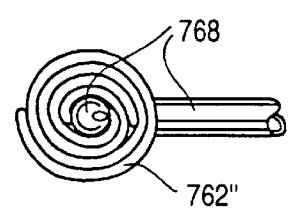
FIG. 19D is an end view of the catheter of FIG. 19C.

FIGS. 19A–19D show a first example of a nondistensible eccentric occlusion balloon 762. FIG. 19A shows a side view of the occlusion balloon in the deflated state 762 and inflated state 762'. FIG. 19B shows an end view of the same occlusion balloon in the deflated 762 and inflated states 762'. The occlusion balloon 762 is molded in an asymmetrical shape with a large side 764 and a smaller side 766. The occlusion balloon 762 is mounted on the catheter shaft 768 with the larger side 764 oriented toward the outside of the distal curve of the catheter. The occlusion balloon tends to flatten out, as shown by solid lines 762, when it is deflated. In order to reduce the deflated profile of the balloon for introduction into a peripheral artery, the flattened balloon 762" is wrapped around the catheter shaft 768 as shown in a side view in FIG. 19C and an end view in FIG. 19D.

FIGS. 20A–20D show a second example of a nondistensible eccentric occlusion balloon 780. FIG. 20A shows a side view of the occlusion balloon in the deflated state 780 and inflated state 780'. FIG. 20B shows an end view of the same occlusion balloon in the deflated state 780 and inflated state 780'. The occlusion balloon 780 is molded in an asymmetrical shape with a large side 782 and a smaller side 784. The occlusion balloon 780 is mounted on the catheter shaft 786 with the larger side 782 oriented toward the outside of the distal curve of the catheter. In this embodiment, the smaller side 784 of the occlusion balloon is adhesively bonded to the catheter shaft 786 along the length of the balloon 780 so that the inflated balloon 780' expands only toward the outside of the distal curve of the catheter. The occlusion balloon flattens out, as shown by solid lines 780, when it is deflated. In order to reduce the deflated profile of the balloon for introduction into an artery, the flattened balloon 780" is wrapped around the catheter shaft as shown in a side view in FIG. 20C and an end view in FIG. 20D.

The eccentrically shaped occlusion balloons of FIGS. 14 and 16–20 serve to help center the distal tip of the aortic partitioning catheter within the ascending aorta for uniform distribution of cardioplegic fluid injected through the infusion lumen and for aligning the tip of the catheter with the center of the aortic valve when other instruments are introduced through the infusion lumen. The degree of concentricity of the occlusion balloon can be varied from perfectly concentric to completely eccentric, or one-sided, using the embodiments and methods described in connection with FIGS. 14 and 16–20. Specially shaped occlusion balloons can also be used with the aortic partitioning catheter of the present invention for maximizing the working space within the ascending aorta between the aortic valve and the occlusion balloon. This aspect of the invention will be of particular significance when the catheter system is used for arresting the heart so that surgery or other interventional procedures can be performed on the patient's aortic valve. Whether the aortic valve surgery is performed by thoracoscopic methods, endovascular methods or open chest surgical methods, it will be beneficial to be able to occlude the ascending aorta as required for establishing cardiopulmonary bypass without obstructing surgical access to the aortic valve. This aspect of the invention will also find particular utility when performing port-access CABG surgery with a saphenous vein bypass graft or other free graft which must be anastomosed to the ascending aorta because the occlusion balloon will not interfere with the anastomosis procedure. FIGS. 21–24 show four variations of specially shaped balloons developed for this purpose. These balloons can be manufactured from elastomeric materials or from nondistensible, inelastic materials as previously described.

Figure 21:
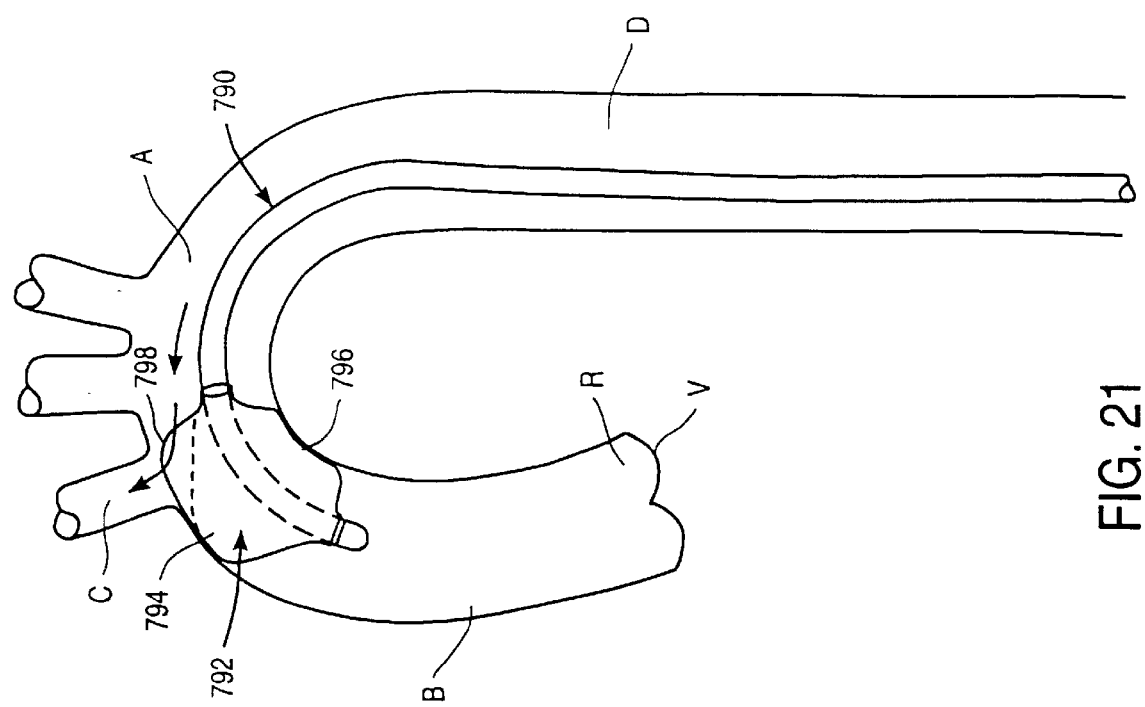
FIG. 21 is a schematic partly cut-away representation of a patient's aortic arch with an endoaortic partitioning catheter having a shaped occlusion balloon positioned in the ascending aorta.

FIG. 21 is a schematic partly cut-away representation of a patient's aortic arch A with a first variation of an endoaortic partitioning catheter 790 having a shaped occlusion balloon 792 positioned in the ascending aorta B. The occlusion balloon 792 has a generally cylindrical outer geometry that has been modified by curving it to match the curvature of the aortic arch A. Thus, the surface of the occlusion balloon facing the outside curve of the aortic arch A has a convex curvature 794 to match the concave curvature of the aortic wall at that point and the surface of the occlusion balloon facing the inside curve of the aortic arch A has a concave curvature 796 to match the convex curvature of the opposite aortic wall. The geometry of the occlusion balloon 792 is further modified by molding a groove or indentation 798 into the proximal edge of the convexly curved outer surface 794 of the balloon 792. The indentation 798 is positioned to allow blood flow past the occlusion balloon 792 into the brachiocephalic artery C. This allows the occlusion balloon 792 of the aortic partitioning catheter 790 to be placed as far downstream in the ascending aorta as possible without occluding flow to the brachiocephalic artery C from the cardiopulmonary bypass system. The working space between the aortic valve V and the occlusion balloon 792 is maximized to allow maneuvering of surgical instruments, interventional catheters or a valve prosthesis within the ascending aorta B. Although it does not serve to occlude the aortic lumen, the proximal portion of the occlusion balloon 792 contacts the aortic wall and helps to stabilize the inflated balloon within the aorta to keep the distal end of the catheter centered and to help prevent unintended displacement of the inflated balloon.

Figure 22:
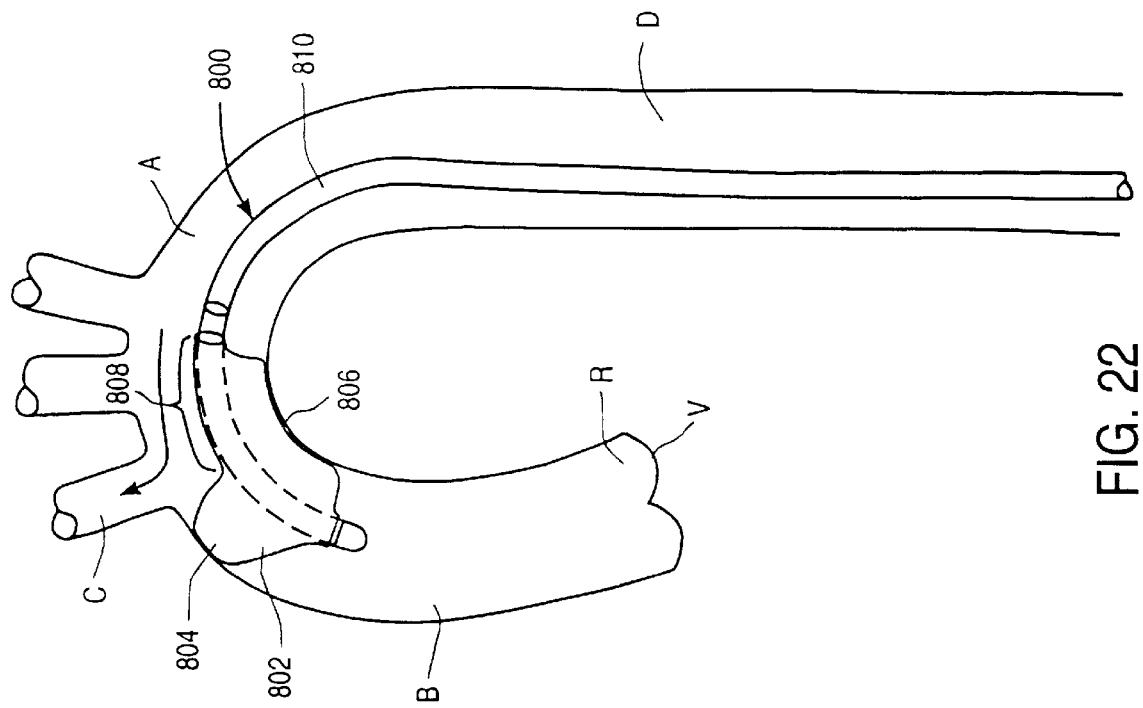
FIG. 22 is a schematic partly cut-away representation of a patient's aortic arch with an endoaortic partitioning catheter having a shaped occlusion balloon positioned in the ascending aorta.

FIG. 22 is a schematic partly cut-away representation of a patient's aortic arch A with a second variation of an endoaortic partitioning catheter 800 having a shaped occlusion balloon 802 positioned in the ascending aorta B. As in the previous example, the occlusion balloon 802 has a generally cylindrical outer geometry that has been modified by curving it to match the curvature of the aortic arch A. The surface of the occlusion balloon facing the outside curve of the aortic arch A has a convex curvature 804 to match the concave outer curvature of the aortic wall and the surface of the occlusion balloon facing the inside curve of the aortic arch A has a concave curvature 806 to match the convex inner curvature of the opposite aortic wall. The geometry of the occlusion balloon 802 is further modified by molding a large ramp-shaped indentation 808 into the proximal side of the convexly curved outer surface 804 of the balloon 802. The wall of the occlusion balloon 802 can be adhesively attached to the catheter shaft 810 along the length of the ramp-shaped indentation 808 to help maintain the geometry of the balloon when subjected to inflation pressure. The ramp-shaped indentation 808 is positioned to allow blood flow past the occlusion balloon 802 into the brachiocephalic artery C. This allows the occlusion balloon 802 of the aortic partitioning catheter 800 to be placed as far downstream in the ascending aorta as possible without occluding flow to the brachiocephalic artery C in order to maximize the working space between the aortic valve V and the occlusion balloon 802. The broad ramp-shaped indentation 808 in the occlusion balloon 802 lessens the need for careful placement of the occlusion balloon 802 with respect to the brachiocephalic artery C without danger of occluding it. The concavely curved inner surface 806 of the occlusion balloon 802 provides an extended contact surface with the wall of the aortic arch A to stabilize the inflated occlusion balloon 802 and to discourage unintended movement or dislodgement of the occlusion balloon 802. As in the previous embodiment, the proximal portion of the occlusion balloon 802 contacts the aortic wall and helps to stabilize the inflated balloon within the aorta to keep the distal end of the catheter centered and to help prevent unintended displacement of the inflated balloon.

Figure 23A:
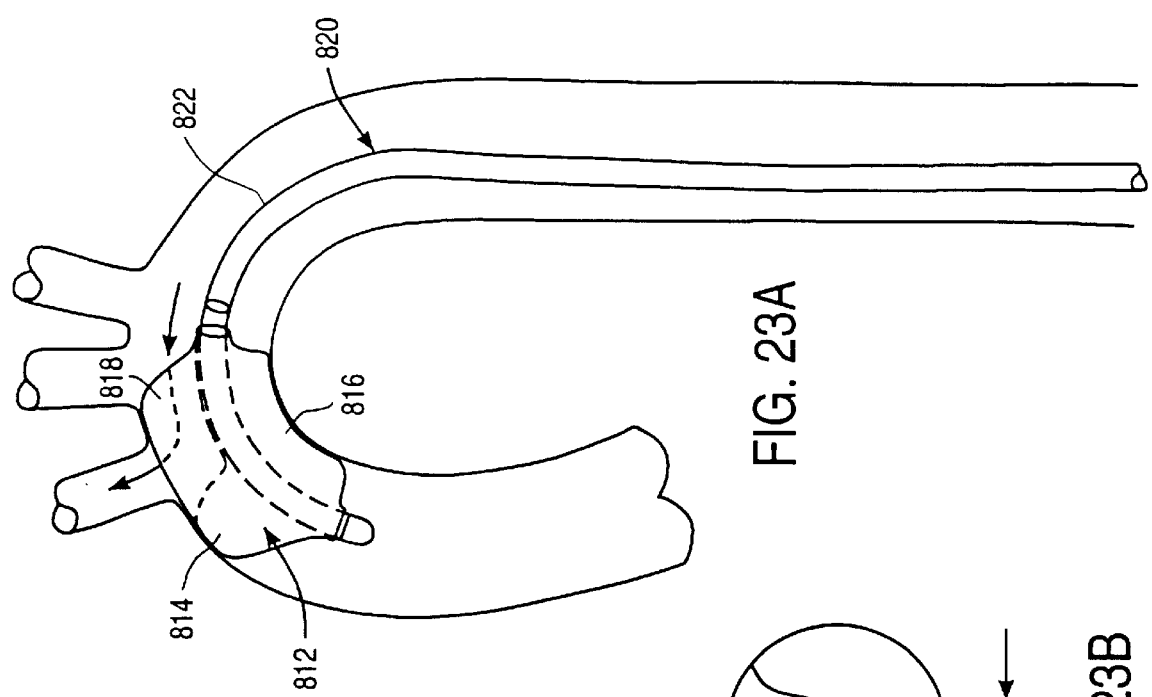
FIG. 23A is a schematic partly cut-away representation of a patient's aortic arch with an endoaortic partitioning catheter having a shaped occlusion balloon positioned in the ascending aorta.
Figure 23B:
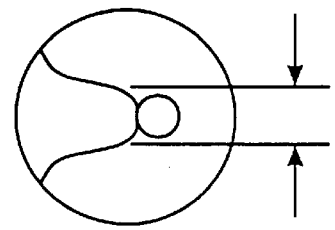
FIG. 23B is a transverse cross section of the shaped occlusion balloon of FIG. 23A.

FIG. 23A is a schematic partly cut-away representation of a patient's aortic arch A with a third variation of an endoaortic partitioning catheter 820 having a shaped occlusion balloon 812 positioned in the ascending aorta B. FIG. 23B is a transverse cross section of the shaped occlusion balloon of FIG. 23A. This occlusion balloon 812 also has a generally cylindrical outer geometry that has been modified by curving it to match the curvature of the aortic arch A. The surface of the occlusion balloon facing the outside curve of the aortic arch A has a convex curvature 814 to match the concave outer curvature of the aortic wall and the surface of the occlusion balloon facing the inside curve of the aortic arch A has a concave curvature 816 to match the convex inner curvature of the opposite aortic wall. The geometry of the occlusion balloon 812 is further modified by molding an extended groove or invagination 818 into the proximal side of the convexly curved outer surface 814 of the balloon 812. The extended groove 818 should have a width at least as wide as the ostium of the brachiocephalic artery C. The wall of the occlusion balloon 812 can be adhesively attached to the catheter shaft 822 along the length of the extended groove 818 to help maintain the geometry of the balloon when subjected to inflation pressure. The extended groove 818 is positioned to allow blood flow past the occlusion balloon 812 into the brachiocephalic artery C. This allows the occlusion balloon 812 of the aortic partitioning catheter 800 to be placed even farther downstream in the ascending aorta without occluding flow to the brachiocephalic artery C in order to maximize the working space between the aortic valve V and the occlusion balloon 812. Again, the concavely curved inner surface 816 of the occlusion balloon 812 provides an extended contact surface with the wall of the aortic arch A to stabilize the inflated occlusion balloon 812 and to discourage unintended movement or dislodgement of the occlusion balloon 812.

Figure 24:
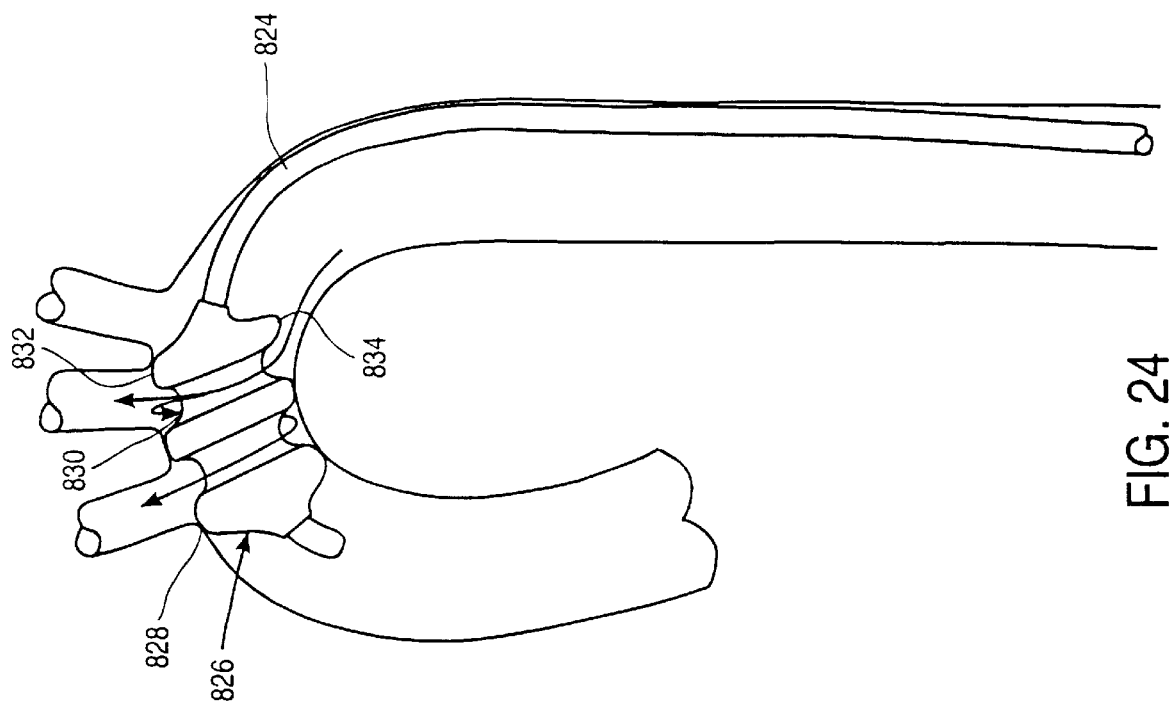
FIG. 24 is a schematic partly cut-away representation of a patient's aortic arch with an endoaortic partitioning catheter having a shaped occlusion balloon positioned at the apex of the aortic arch.

FIG. 24 is a schematic partly cut-away representation of a patient's aortic arch A with a fourth variation of an endoaortic partitioning catheter 824 having a shaped occlusion balloon 826 positioned at the apex of the aortic arch A. In an effort to further maximize the working space between the aortic valve V and the occlusion balloon 826 the geometry of the occlusion balloon 826 has been modified so that it can be placed at the very apex of the aortic arch A without compromising blood flow to the brachiocephalic, common carotid or subclavian arteries. The occlusion balloon 826 has a generally cylindrical outer geometry modified with a helical groove 830 that starts at the proximal end 834 of the balloon and spirals around the balloon 826 in the distal direction. In this illustrative embodiment, the spiral groove 830 forms approximately two complete turns encircling the occlusion balloon 826 and is delimited by an annular ring 828 that forms a seal with the aortic wall at the distal end of the balloon 826 to isolate the heart and the coronary arteries the systemic blood flow which is supported by the cardiopulmonary bypass system. The spiral groove 830 forms a flow path for oxygenated blood from the descending aorta to the brachiocephalic, common carotid or subclavian arteries C. A spiral ridge 832 that runs along the spiral groove 830 contacts the aortic wall and stabilizes the inflated occlusion balloon 826 to prevent unintended movement of the occlusion balloon 812 without occluding blood flow to the head and neck arteries. This same effect can be accomplished using functionally equivalent balloon geometries. For instance, this effect could be achieved with a shaped balloon having an annular ring at the distal end of the balloon to seal against the aortic wall, isolating the heart and the coronary arteries from systemic blood flow, and a multiplicity of bumps or ridges at the proximal end to contact the aortic wall and stabilize the balloon, with the space between the bumps providing a blood flow path to the head and neck arteries branching from the aortic arch.

Figure 25A:
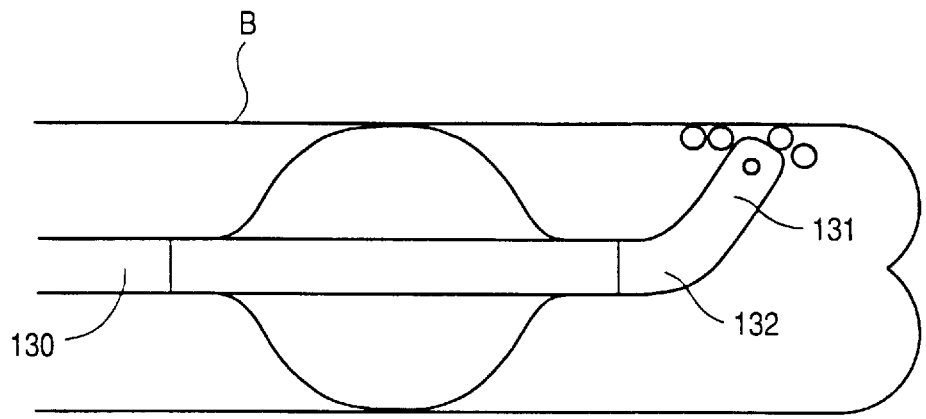
FIG. 25A illustrates an endoaortic partitioning catheter with a curved tip for de-airing the heart and ascending aorta.
Figure 25B:
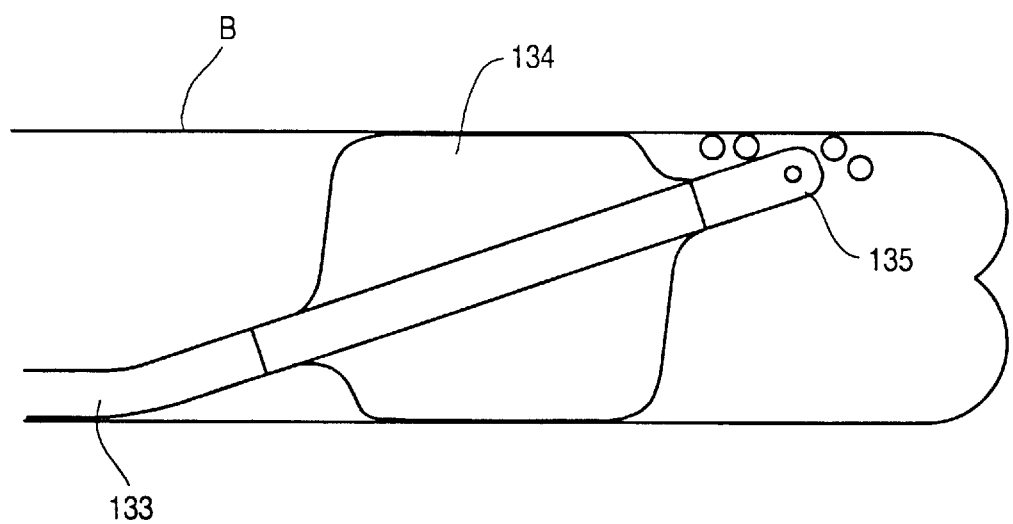
FIG. 25B illustrates an alternate embodiment of an endoaortic partitioning catheter for de-airing the heart and ascending aorta.

Another aspect of the present invention is illustrated in FIGS. 25A and 25B. In this embodiment, the function of de-airing the heart and the ascending aorta at the completion of the interventional procedure has been combined with the endoaortic partitioning catheter 130. The catheter 130 is configured so that the distal tip 131 of the catheter is positioned near the anterior wall of the ascending aorta B. This can be accomplished by making a curve 132 in the distal portion of the catheter shaft that brings the tip 131 of the catheter near the anterior wall of the ascending aorta B, as shown in FIG. 25A. Alternatively, the occlusion balloon 134 can be shaped so that when the balloon 134 is inflated, the distal tip 135 of the catheter 133 is directed toward the anterior wall of the ascending aorta B, as shown in FIG. 25B. The advantage of this modification of the endoaortic partitioning catheter is that, when the patient is placed in a supine position, the distal tip of the catheter is at the highest point in the ascending aorta so that any air bubbles that enter the heart, the coronary arteries or the aortic root during the course of surgery can be vented out through a lumen in the catheter prior to deflating the occlusion balloon to reverse the cardioplegic arrest.

Figure 26:
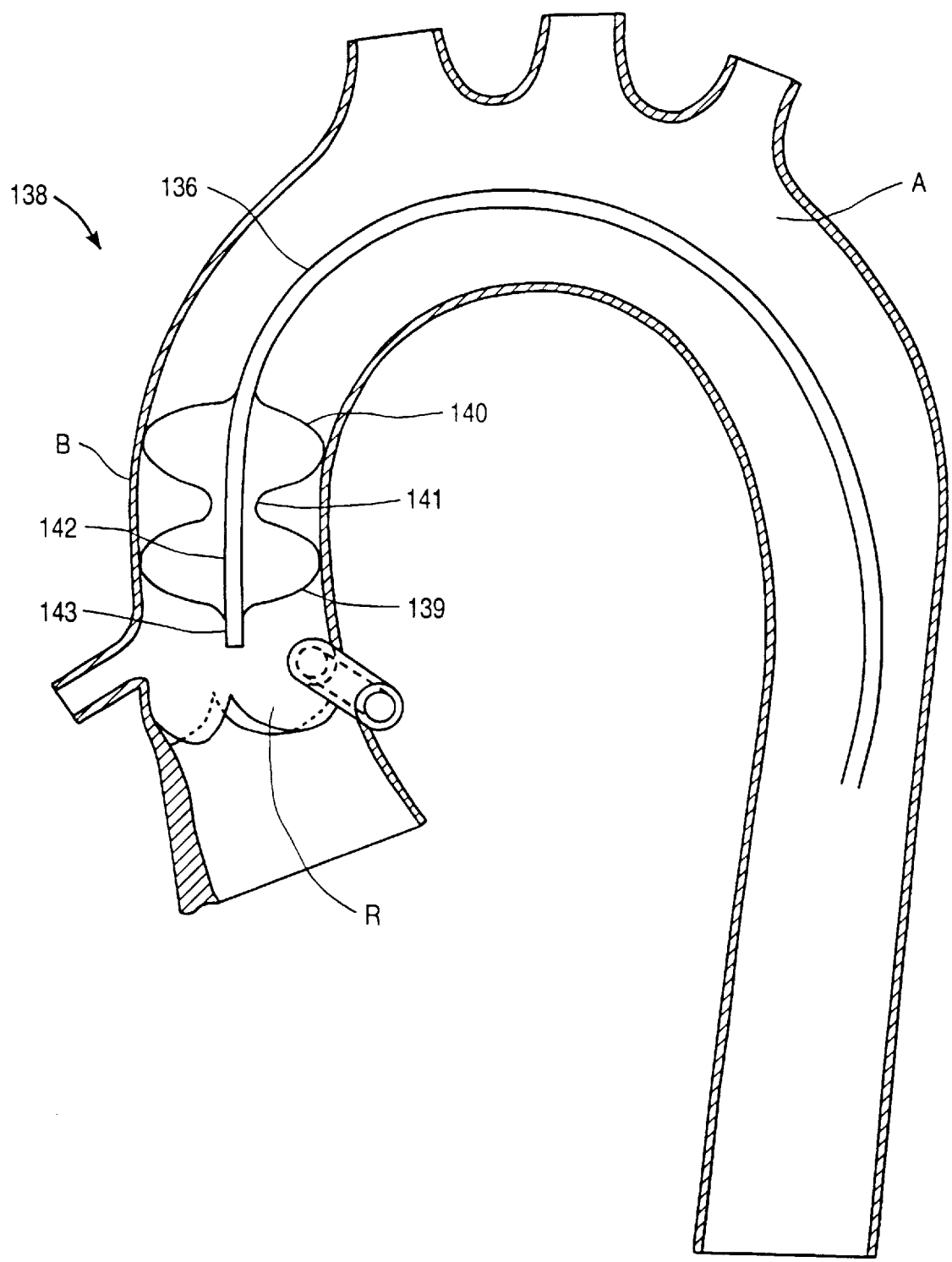
FIG. 26 illustrates an endoaortic partitioning catheter having a dumbbell-shaped occlusion balloon for centering the catheter tip within the ascending aorta.

FIG. 26 shows another application of shaped balloons for the purpose of centering the tip 137 of the endoaortic partitioning catheter 136 within the ascending aorta B. The expandable occlusion balloon 138 has a distal occlusion means 139 with an expanded diameter sufficient to occlude the ascending aorta B and a proximal stabilizing means 140 with an expanded diameter sufficient to contact the inner surface of the ascending aorta B. Between the occlusion means 139 and the stabilizing means 140 is an area of reduced diameter 141. When expanded, the occlusion means 139 blocks substantially all systolic and diastolic blood flow through the ascending aorta B. The stabilizing means 140 contacts the inner surface of the ascending aorta B and orients the distal segment 142 of the catheter shaft so that it is parallel with the axis of the ascending aorta B, reliably centering the catheter tip 143 within the aortic lumen just superior to the aortic root R.

One particular embodiment for achieving this geometry is shown in FIG. 26. In this embodiment, the occlusion balloon 138 has a dumbbell shape when expanded. The occlusion means is provided by a distal lobe 139 of the dumbbell shaped balloon 138, and the stabilizing means is provided by a proximal lobe 140 of the balloon, with a waist 141 of reduced diameter between the proximal 140 and distal 139 lobes. The dumbbell shaped occlusion balloon 138 thus has two rings of contact with the inner surface of the ascending aorta B for better stabilization and orientation of the balloon in the proper position. Additional advantages of this configuration are that by providing two rings of contact with the inner surface of the ascending aorta B, the dumbbell shaped balloon 138 can achieve a better and more reliable seal and greater resistance to displacement of the inflated balloon.

Another particular embodiment for achieving a similar geometry would have two separate, but closely spaced, expandable balloons mounted on the distal segment of the catheter shaft. When expanded, the more distal balloon serves as an occlusion means, and the more proximal balloon serves as a stabilizing means for orienting the distal segment of the catheter parallel to the axis of the aortic lumen. It should be noted that the stabilizing means need not occlude the ascending aorta. However, for proper effect, it should contact the inner surface of the ascending aorta at at least three points around the inner circumference of the ascending aorta. Thus, the stabilizing means may have other non-spherical geometries that do not fully occlude the ascending aorta. For instance, multiple smaller balloons could be mounted circumferentially around the catheter shaft so that, when the balloons are inflated, they contact the inner surface of the ascending aorta at at least three points. Likewise, an expandable, non-balloon stabilizing means can also be used for contacting the inner surface of the ascending aorta for stabilizing and orienting the distal tip of the catheter.

Figure 27:
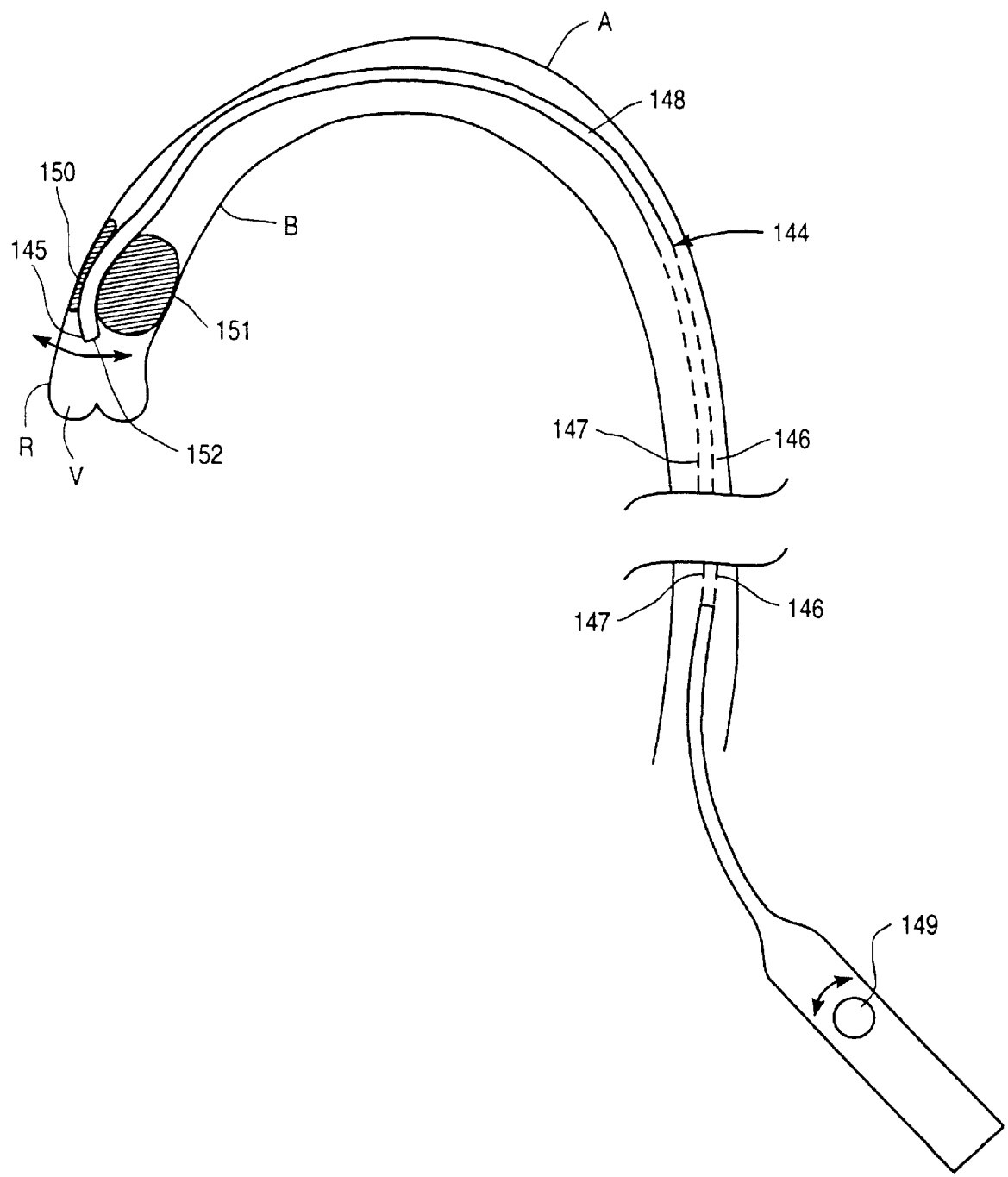
FIG. 27 illustrates an endoaortic partitioning catheter having a steerable distal tip for centering the catheter tip within the ascending aorta.

Another approach to centering the distal tip of the endoaortic partitioning catheter within the ascending aorta, shown in FIG. 27, works independently of balloon geometry. In this embodiment, the distal tip 145 of the endoaortic partitioning catheter 144 is made steerable by one or more control wires 146, 147 extending from the proximal end of the catheter 144 to the distal end through one or more lumens in the side wall of the catheter shaft 148. The distal end of the control wires 146, 147 connect to a rigid ring or other anchoring device embedded in the wall of the catheter shaft 148 near the distal tip 145 of the catheter 144. The proximal end of the control wires 146, 147 connect to a control means 149 at the proximal end of the catheter. For catheters 144 having one degree of freedom (i.e. 1–2 control wires) in the steerability of the distal tip 145, the control means 149 can be a control knob or lever or similar control device. For catheters 144 having two degrees of freedom (i.e. 4 or more control wires) in the steerability of the distal tip 145, the control means 149 can be a joy stick or similar control device. The shaft 148 of the catheter should be made with a flexible distal segment 150 which is relatively more flexible than the proximal portion of the catheter shaft 148. This concentrates the deflection of the catheter shaft in the distal section 150 when one or more of the control wires 146, 147 are tensioned by the control means 149 to steer the distal tip 145 of the catheter 144.

The steering mechanism can be used to deflect the distal tip 145 of the catheter shaft away from the aortic wall as the catheter is advanced through the aortic arch A and into the ascending aorta B. This reduces the likelihood of any trauma caused to the aortic wall by the catheterization and reduces the chances of dislodging any calcifications or other emboli from the aortic wall as the catheter 144 passes. Once the catheter 144 is in place in the ascending aorta B and the occlusion balloon 151 is inflated, the position of the catheter tip 145 can be verified fluoroscopically and the steering mechanism used to direct the tip 145 of the catheter toward the center of the aortic lumen in spite of any curvature in the ascending aorta B or eccentricities in the occlusion balloon 151. If any diagnostic or therapeutic instruments are to be delivered through the inner lumen 152 of the endoaortic partitioning catheter 144 the steering mechanism can be used for centering the distal tip 145 of the catheter 144 with respect to the aortic valve V or for directing the instruments to other anatomical features within the heart or the aortic root R. The steering mechanism can also be used for directing the catheter tip 145 toward the anterior wall or the highest point in the ascending aorta for deairing the heart and the ascending aorta at the completion of the interventional procedure before deflating the occlusion balloon to reverse the cardioplegic arrest, as described above in relation to FIG. 25.

Figure 28:
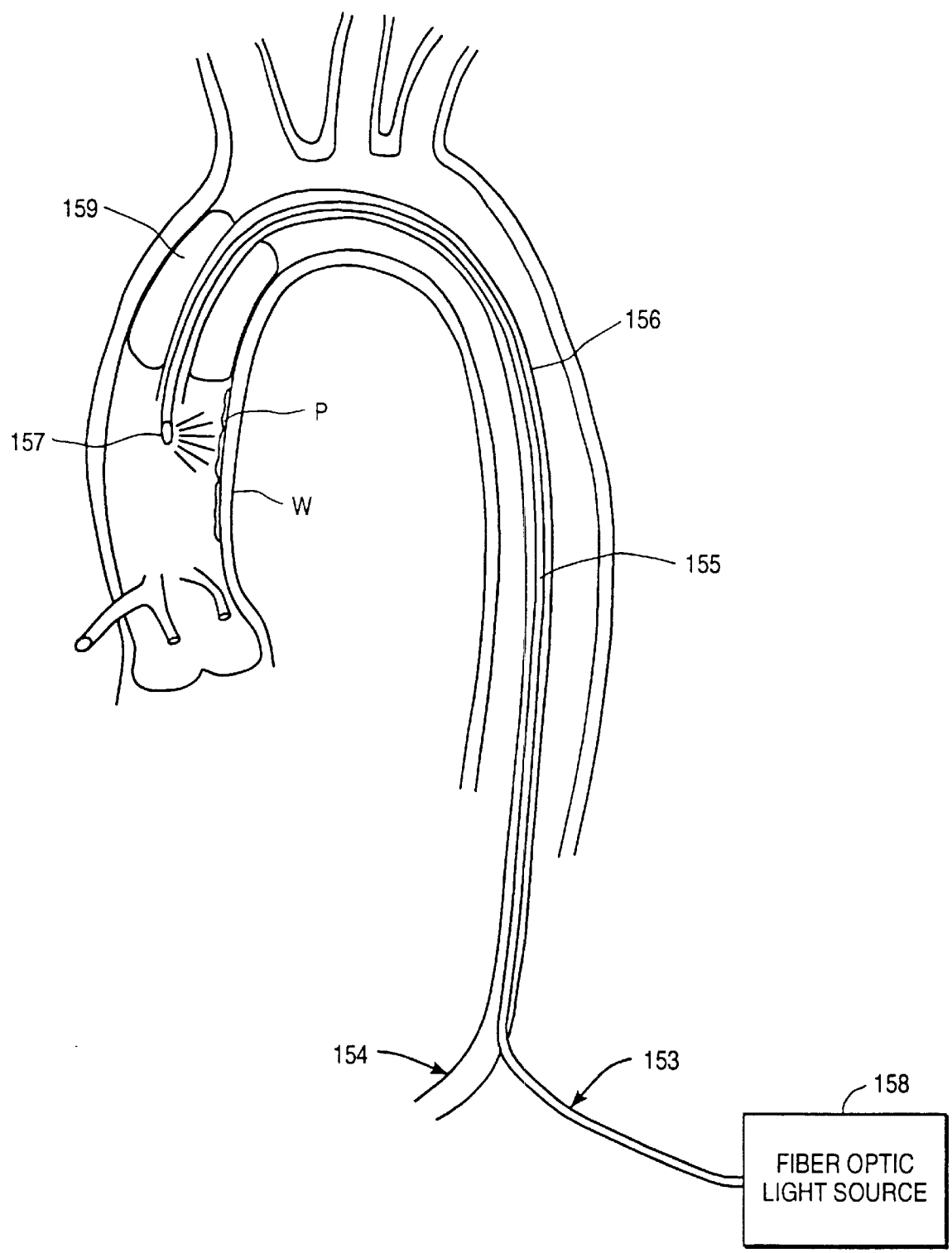
FIG. 28 illustrates an endoaortic partitioning catheter including a fiberoptic bundle for transillumination of the aortic wall and/or for facilitating non-fluoroscopic placement of the catheter.

Another aspect of the present invention is illustrated in FIG. 28. In this embodiment, a fiberoptic illumination device 153 has been combined with the endoaortic partitioning catheter 154. The fiberoptic illumination device 153 can serve two distinct purposes. The first function of the fiberoptic illumination device 153 can be for transillumination of the aortic wall W for detecting plaque and calcifications P in the aortic wall and for identifying the optimal point for creating a proximal anastomosis of a coronary bypass vein graft. In this embodiment, a fiberoptic bundle 155 is extended through the shaft 156 of the endoaortic partitioning catheter 154 to the distal end. The fiberoptic bundle 155 may be built into the wall of the catheter shaft 156 or a separate fiberoptic bundle 155 can be removably inserted through the infusion lumen of the catheter 154. At the distal end of the fiberoptic bundle 155 is a light diffuser 157 or a means for directing a broad lateral beam of light. The proximal end of the fiberoptic bundle is connected to a high intensity source of visible light 158. When the light beam or diffuse illumination passes through the wall W of the aorta, calcifications and heavy atherosclerotic plaque P can be detected as shadows in the aortic wall W. The exterior of the aorta can be observed with a thoracoscope inserted through an intercostal access port into the patient's chest. The light source for the thoracoscope should be turned off while performing the transillumination so that the light coming through the aortic wall can be clearly seen. When this technique is used in open-chest bypass surgery, the lights in the operating room should be dimmed so that the light coming through the aortic wall can be seen. A clear, brightly lit section of the aortic wall W without shadows will indicate a relatively plaque free area of the aorta suitable for making the distal anastomosis. If a separate fiberoptic bundle 155 is inserted through the infusion lumen of the catheter 154, it can be manipulated from outside of the patient's body to scan the entire ascending aorta B to find the optimum anastomosis site or to find multiple anastomosis sites for multi-vessel bypass operations.

The second function of the fiberoptic illumination device 153 can be for facilitating placement of the endoaortic partitioning catheter 154 without the need for fluoroscopic guidance. In this embodiment, a fiberoptic bundle 155 is extended through the shaft 156 of the endoaortic partitioning catheter 154 to the distal end. Again, the fiberoptic bundle 155 may be built into the wall of the catheter shaft 156 or a separate fiberoptic bundle 155 can be removably inserted through the infusion lumen of the catheter 154. Located at the distal end of the fiberoptic bundle 155 is a means 157 for directing a narrow lateral beam of light to create a spot or a 360° ring of light around the tip of the catheter. The proximal end of the fiberoptic bundle 155 is connected to a high intensity source of visible light 158. When the endoaortic partitioning catheter 154 is inserted into the ascending aorta B, the position of the catheter tip can be determined by the position of the spot or ring of light where it shines through the aortic wall W. When the endoaortic partitioning catheter 154 is in the correct position, the occlusion balloon 159 can be inflated and a cardioplegic agent infused to arrest the heart.

These two functions of the fiberoptic illumination device 153 can be combined into one device if the optical elements are chosen to deliver a beam which is a compromise between the broad beam needed for aortic wall transillumination and the narrow beam preferred for the catheter location function. Alternatively, an optical system could be chosen which is selectively capable of delivering a broad or narrow lateral beam of light.

In other alternatively embodiments, the occlusion balloon 158 can be illuminated from the interior with the fiberoptic illumination device 153 to monitor balloon placement, inflation and migration. The effectiveness of the illumination can be enhanced by incorporating reflective or fluorescent material in the balloon or the inflation fluid.

Being able to detect the precise position of the endoaortic partitioning catheter 154 without the need for fluoroscopic imaging has the potential of simplifying the catheter placement procedure and the equipment needed in the operating room. Other non-fluoroscopic means for detecting the position of the catheter tip include placing a metallic or magnetic marker at the tip of the catheter and using a thoracoscopically placed Hall effect proximity detector or magnetometer in the chest cavity to detect the position of the catheter tip through the aortic wall. Another means of detecting the position of the catheter tip within the ascending aorta is by ultrasonic imaging. An endoscopic ultrasonic imaging probe can be introduced through an access port in the chest or a transoesophageal ultrasound probe can be used. The imaging of the catheter can be enhanced by placing an echogenic marker near the tip of the catheter. A material with significantly higher or lower acoustic impedance than the catheter and the surrounding tissue and blood can serve as an echogenic marker. For example, a metal ring with a roughened exterior surface or an air-filled pocket or ring of closed cell foam mounted on or embedded in the tip of the catheter will serve as an echogenic marker. The catheter tip can be observed with ultrasonic imaging as the catheter is advanced into the ascending aorta to assure proper placement of the occlusion balloon.

Figure 29:
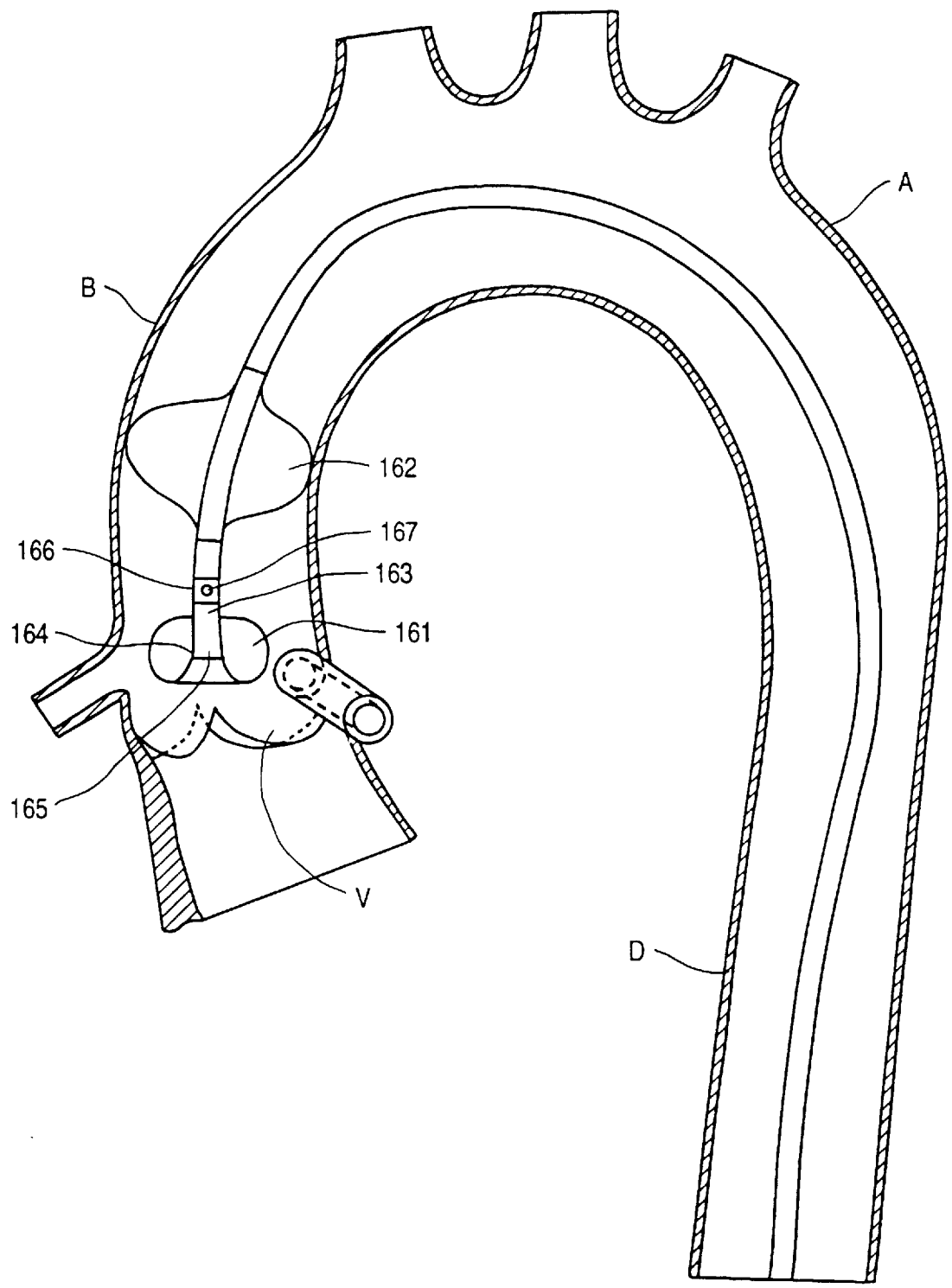
FIG. 29 illustrates an endoaortic partitioning catheter having an inflatable bumper balloon for protecting the aortic wall from the catheter tip and for facilitating non-fluoroscopic placement of the catheter.

Another approach for facilitating placement of the endoaortic partitioning catheter without the need for fluoroscopic guidance is illustrated in FIG. 29. This embodiment of the endoaortic partitioning catheter 160 has a second exandable member 161 mounted on the distal end of the catheter distal to the first exandable occlusion member 162. In a particular embodiment, the distal expandable member 161 is an inflatable balloon having a proximal balloon neck 163 which is attached to the catheter shaft 166 and a distal balloon neck 164 which is inverted and attached to the distal tip 165 of the catheter shaft. When the distal expandable member 161 is inflated, it expands to surround and protect the distal tip 165 of the catheter. If an expandable balloon is used for the first exandable occlusion member 162 the first 162 and second 161 expandable members can be inflated through a single inflation lumen within the catheter shaft 166. Preferably, however a separate second inflation lumen is provided for individually inflating the distal expandable member 162. The distal expandable member 162 preferably has a smaller expanded diameter than the first exandable occlusion member 161 so that it does not occlude the lumen of the ascending aorta B.

In operation, the endoaortic partitioning catheter 160 is inserted and advanced into the descending aorta D. Then, the distal expandable member 161 is inflated to act as a soft protective bumper for the distal end 165 of the catheter 160. The catheter 160 can be advanced over the aortic arch A and into the ascending aorta B with very little concern about causing trauma to the aortic wall or dislodging any calcifications or other emboli from the aortic wall as the catheter passes. When the catheter 160 is in the ascending aorta B, it is advanced slowly until the distal expandable member 161 comes into contact with the aortic valve V. The soft cushion provided by the inflated distal expandable member 161 prevents any damage to the aortic valve V. The operator will be able to feel that the catheter 160 has stopped advancing from the proximal end of the catheter which is outside of the patient's body and will know that the first exandable occlusion member 162 is in proper position in the ascending aorta B between the coronary ostia and the brachiocephalic artery without the need for fluoroscopic verification. The first exandable occlusion member 162 can be inflated to occlude the ascending aorta B and a cardioplegic agent infused through the perfusion lumen that exits the catheter through a port 167 distal to the first exandable occlusion member 162.

Figure 30A:
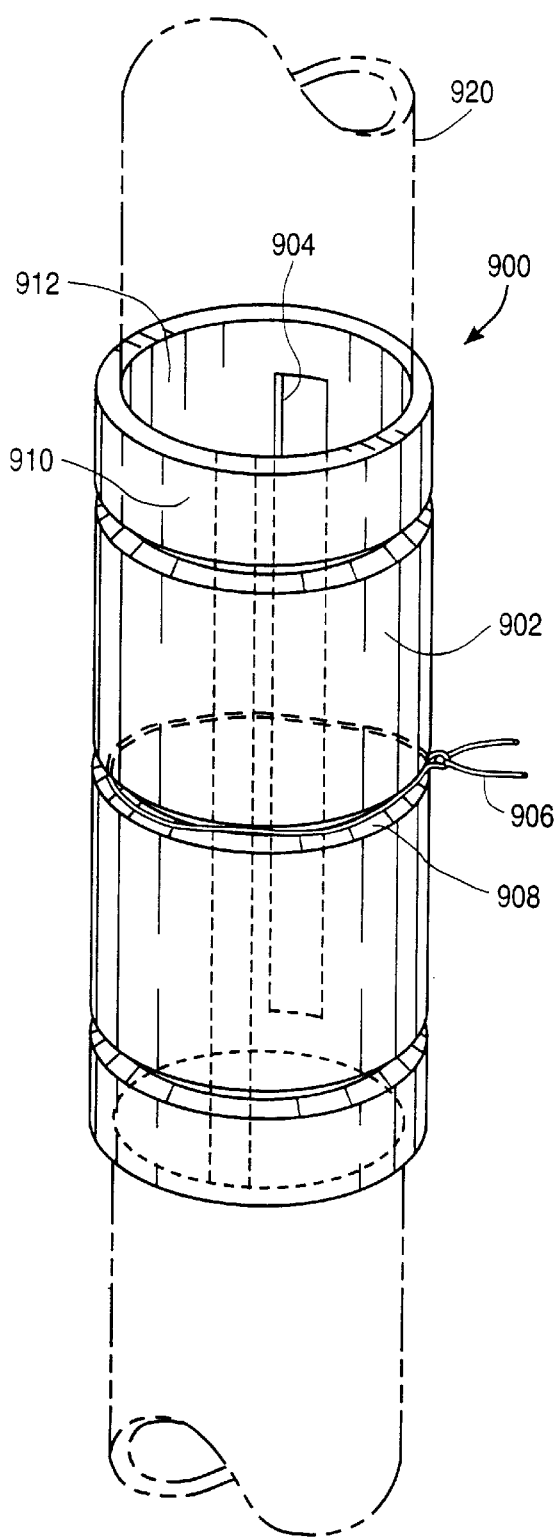
FIG. 30A is a rear three-quarter view of a frictional locking suture ring for use with the endoaortic partitioning catheter.
Figure 30B:
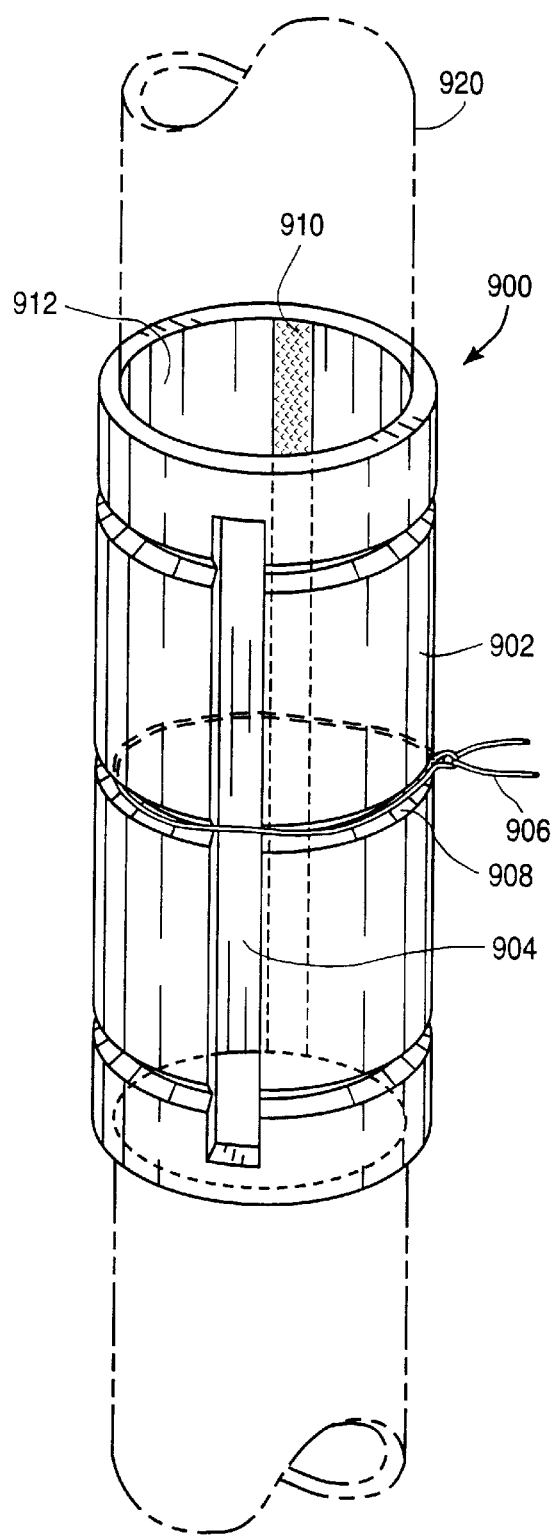
FIG. 30B is a front three-quarter view of the frictional locking suture ring of FIG. 30A.
Figure 31:
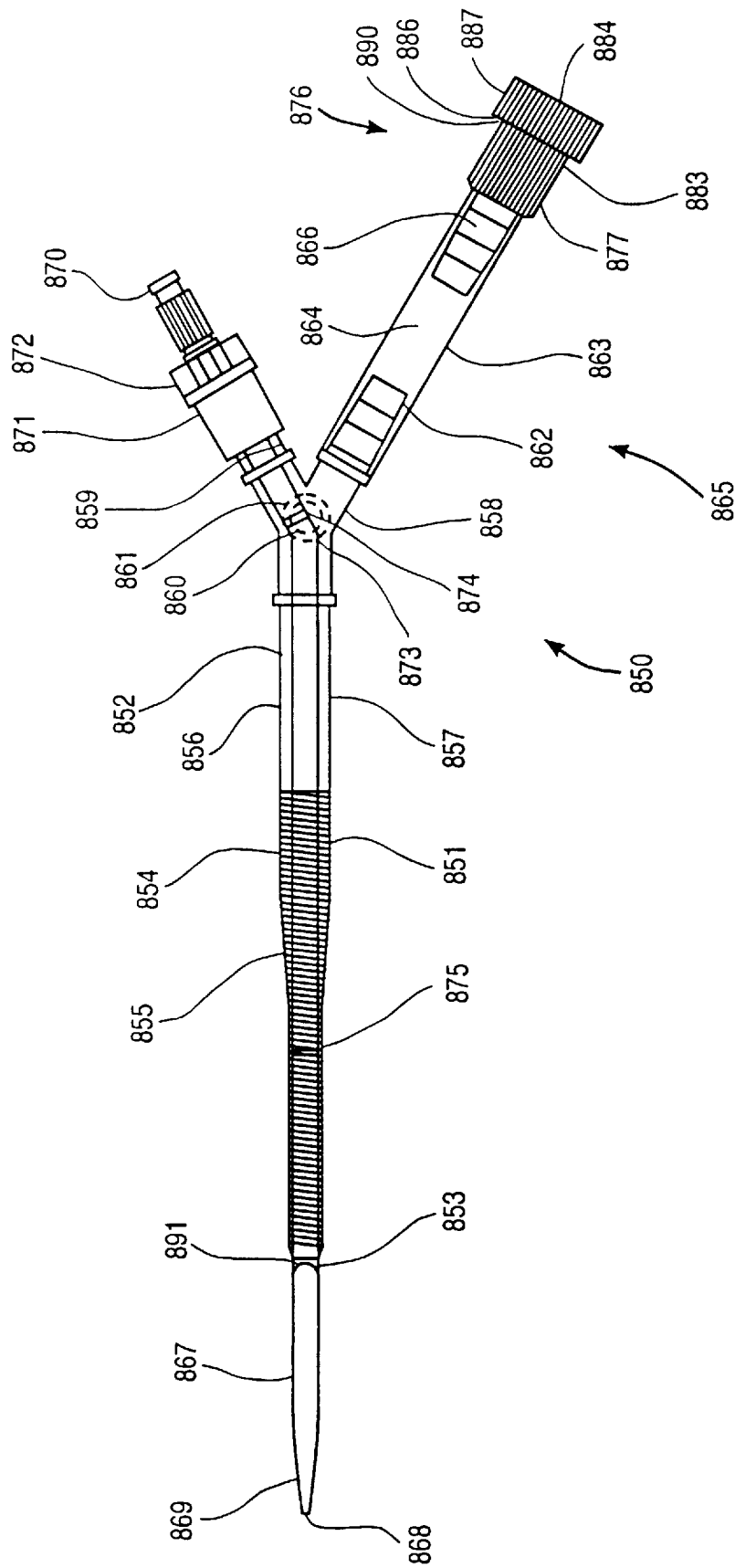
FIG. 31 is a front view of a dual function arterial cannula and introducer sheath for use with the endoaortic partitioning catheter.
Figure 32:
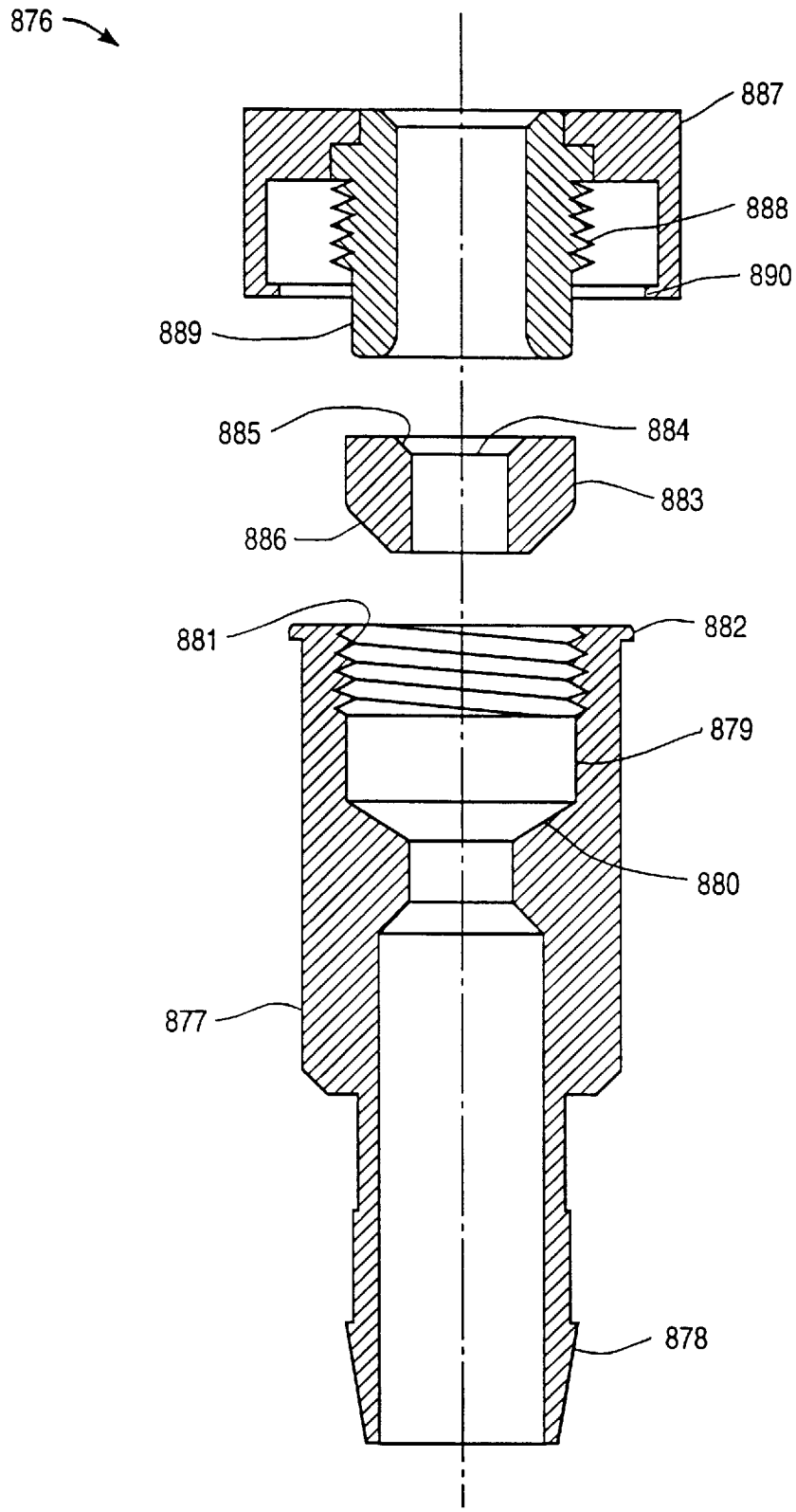
FIG. 32 is a cross sectional view of the hemostasis fitting of the dual function arterial cannula and introducer sheath of FIG. 31.

FIGS. 30A and 30B are detail drawings of an additional feature of the invention which is a frictional locking suture ring 900 for use with the endoaortic partitioning catheter. For indwelling catheters, such as the endoaortic partitioning catheter, it is often desirable to fasten the catheter to the patient or to the surgical drapes to prevent undesired migration or dislodgement of the catheter from its correct position. The frictional locking suture ring 900 of FIGS. 30A and 30B is provided as part of the invention to facilitate anchoring the catheter in place to avoid unintentional movement of the catheter after it has been positioned in the ascending aorta. Typical suture rings on introducer sheaths, central venous catheters and other indwelling catheters are located at a fixed position near the proximal hub of the catheter. This is generally adequate for catheters where the precise placement of the distal tip of the catheter is not critical. With the endoaortic partitioning catheter, however, the precise placement of the distal tip of the catheter within the ascending aorta is highly critical and the distance from the point of insertion of the catheter into the peripheral arterial access site to the ascending aorta is highly variable from patient to patient. Therefore, a standard, fixed-position suture ring would be wholly inadequate in the present application. The frictional locking suture ring of FIGS. 30A and 30B allows the endoaortic partitioning catheter to be precisely positioned and reliably anchored in place with any desired length of the catheter shaft inserted at the access site.

The frictional locking suture ring 900 is preferably made from a tube 902 of a resilient, high-tack polymer, preferably an extrudable or injection moldable thermoplastic elastomer, such as a thermoplastic polyurethane with a hardness in the range of 70–90 Shore A durometer or Kraton™ (Shell Chemical Co.) thermoplastic elastomer with a hardness of about 40 Shore A durometer. The length of the tube 902 is typically from 2–3 cm. The internal diameter of the tube 902 is slightly larger than the external diameter of the shaft of the endoaortic partitioning catheter 920. In an exemplary embodiment for use with a 4 mm diameter or 12 French catheter, the internal diameter of the tube 902 is preferably about 4.5–4.8 mm, providing a diametrical clearance of approximately 0.5–0.8 mm. The external diameter of the tube 902 is typically about 6.5–7.0 mm. There is a longitudinal slot 904 about 1.2–2.0 mm wide through the side of the tube 902.

The frictional locking suture ring 900 is placed over the exterior of the endoaortic partitioning catheter 920 with the shaft of the catheter running through the lumen of the tube. Because of the diametrical clearance between the exterior of the catheter 920 and the interior of the tube 902, the suture ring 900 is free to move along the length of the catheter 920. However, when a suture 906 or other ligature is tied around the suture ring 900, the tube 902 compresses around the exterior of the catheter 920 and the high friction due to the tackiness of the suture ring material creates a firm, nonslip grip on the catheter shaft 920. To facilitate securing the suture 906 to the suture ring 900, a circumferential groove 908 is provided on the exterior of the tube 902. In the illustrative embodiment shown in FIGS. 30A and 30B, there are three circumferential grooves 908 around the tube at positions near the proximal end, the center and the distal end of the longitudinal slot 904 to provide places for tying a suture 906 around the suture ring 900. In an injection molded embodiment of the suture ring 900, other suture attachment means, such as one or more eyelets, can easily be provided on the exterior of the tube 902.

In order to increase the frictional grip between the frictional locking suture ring 900 and the shaft of the endoaortic partitioning catheter 920, a strip of high friction material 910 may be provided on the interior of the tube 902. In the illustrative embodiment of FIGS. 30A and 30B a 1.0 mm wide strip of high friction tape 910 has been adhesively bonded to the interior of the tube 902. A suitable material for use in this application is a self-adhesive high friction tape available from 3M Manufacturing Co., Inc. which is made of a polyurethane film with mineral particles embedded in the exterior surface to enhance the frictional properties. The high friction tape 910 is mounted in the tube 902 with the high friction gripping surface oriented toward the lumen 912 of the tube 902. When a suture 906 is tied around the exterior of the frictional locking suture ring 900, the high friction surface of the tape 910 is pressed against the exterior of the catheter shaft 920 to increase the grip on the catheter.

Preferably, the frictional locking suture ring 900 is placed over the catheter shaft from the distal end during manufacturing. In use, the suture ring 900 initially resides in an out of the way position at the proximal end of the catheter near the proximal hub while the catheter 920 is being introduced and maneuvered into position within the patient's aorta. Once the distal end of the catheter has been maneuvered to the proper position, the catheter 920 can be secured in position by sliding the suture ring 900 along the catheter shaft 920 until it is close to the introduction site. A suture 906 is tied around exterior of the suture ring 900 to create a frictional grip between the suture ring 900 and the catheter shaft 920. The suture 906 is then stitched through the patient's skin dose to the insertion site and tied. This securely fastens the catheter 920 in the desired position relative to the patient's body with the correct length of catheter inserted into the patient's vasculature. If preferred, separate sutures can be used for tying the suture ring 900 and stitching it to the patient. Alternatively, the suture ring 900 can be secured to the surgical drapes covering the patient, though this is less preferred because there can be relative movement between the drapes and the catheter introduction site that could result in movement of the catheter from its desired position.

If it becomes necessary to reposition the catheter 920 at any time during the procedure, the frictional grip can be released by untying or cutting the suture 906 around the suture ring 900. The catheter 920 can be repositioned by sliding it through the lumen 912 of the suture ring and then it can be secured in the new position by retying the suture 906 around the suture ring 900. When it is time to remove the catheter 920, the suture 906 fastening the suture ring 900 to the patient can be cut and the suture ring 900 withdrawn with the catheter 920.

In a further aspect of the invention, illustrated in FIGS. 30–34, the endoaortic partitioning catheter 895 is coupled to an arterial bypass cannula 850 that is specially adapted to serve as a dual purpose arterial bypass cannula and introducer sheath so as to allow the catheter 895 and the cannula 850 to be introduced through the same arterial puncture. The smaller diameter endoaortic partitioning catheters made possible by the embodiments described in relation to FIGS. 5–9, are particularly suitable for use in combination with the special arterial bypass cannula 850. The arterial bypass cannula 850 is configured for connection to a cardiopulmonary bypass system for delivering oxygenated blood to the patient's arterial system. The arterial bypass cannula 850, shown in FIG. 26, has a cannula body 851 which is preferably made of a transparent, flexible, biocompatible polyurethane elastomer or similar material. In one preferred embodiment, the cannula body 851 has a 45° beveled distal end 853, a proximal end 852, a blood flow lumen 857 extending between the proximal end 852 and the distal end 853, and an outflow port 891 at the distal end 853. Alternatively, the cannula body 851 can have a straight cut distal end with chamfered or rounded edge. Optionally, a plurality of additional outflow ports may be provided along the length of cannula body 851, particularly near distal end 853. The cannula body 851 is tapered from the proximal end 852 to the distal end 853 and, in one preferred embodiment, the tapered cannula body 851 is reinforced with a coil of flat stainless steel wire 854 embedded in the wall of the cannula body 851. Adjacent to the proximal end 852 of the cannula body 851, proximal to the reinforcing coil 851, is a clamp site 851 which is a flexible section of the tubular cannula body 851 that can be clamped with an external clamp, such as a Vorse type tube occluding clamp, forming a hemostatic seal to temporarily stop blood flow through the lumen 857 of the cannula 850. In a preferred embodiment, the cannula body 851 has a length between about 10 cm and 60 cm, and preferably between about 15 cm and 30 cm. In one particular embodiment, the cannula body 851 has a distal external diameter of approximately 7 mm or 21 French (Charrière scale) and a distal internal diameter of approximately 6.0 mm or 18 French. In a second particular embodiment, the cannula body 851 has a distal external diameter of approximately 7.7 mm or 23 French (Charrière scale) and a distal internal diameter of approximately 6.7 mm or 20 French. Preferably, the proximal end 852 of the cannula body 851 of either embodiment has an internal diameter of approximately ⅜ inch or 9.5 mm. The choice of which embodiment of the arterial bypass cannula 850 to use for a given patient will depend on the size of the patient and the diameter of the artery chosen for the arterial cannulation site. Generally, patients with a larger body mass will require a higher infusion rate of oxygenated blood while on cardiopulmonary bypass, therefore the larger arterial bypass cannula 850 should be chosen if the size of the artery allows.

Figure 34:
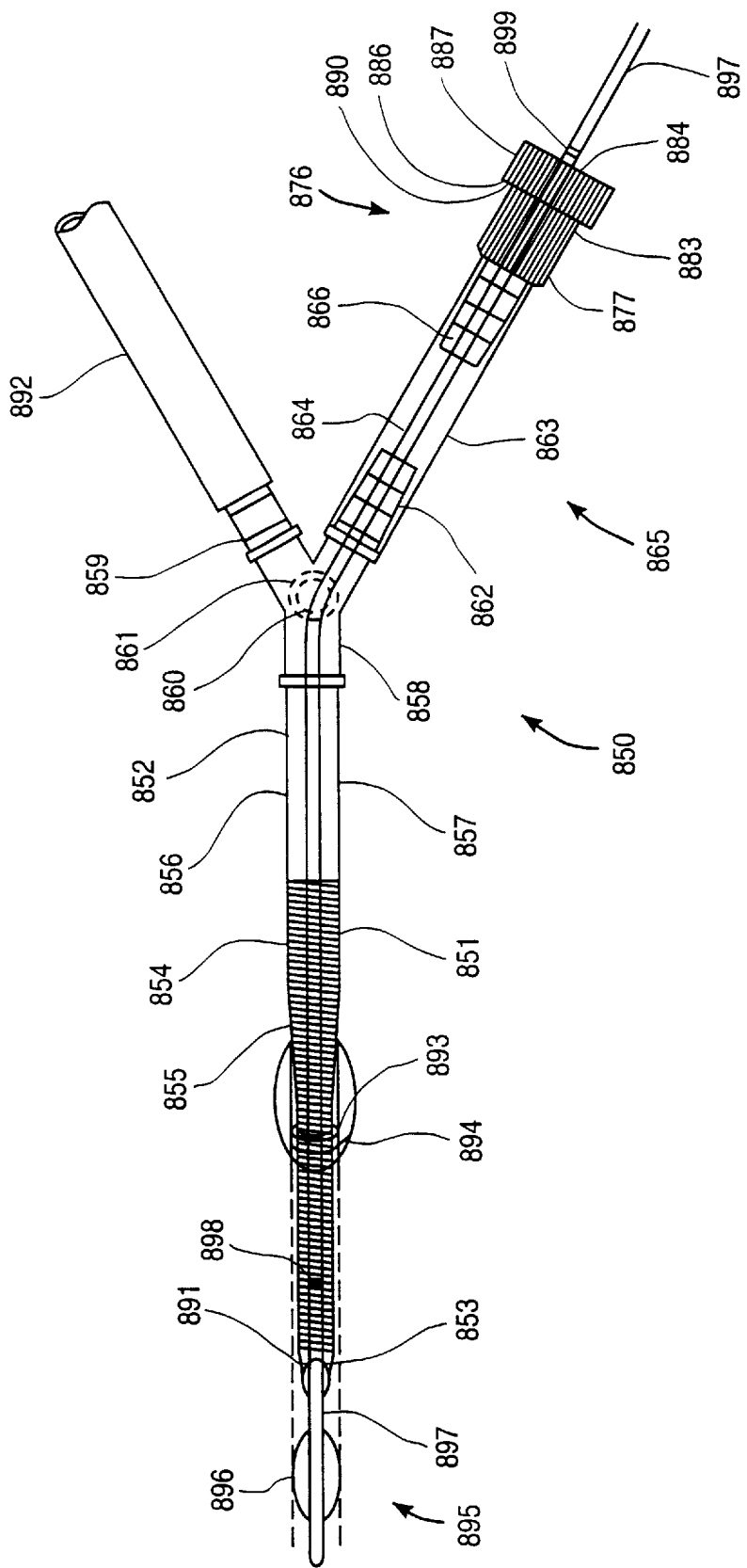
FIG. 34 illustrates the cannula of FIGS. 31 and 32 with the endoaortic partitioning catheter introduced into the patient's femoral artery.

An adapter assembly 865 is connected to the proximal end 852 of the cannula body 851. In one preferred embodiment, the adapter assembly 865 and the cannula body 851 are supplied preassembled as a single, sterile, ready-to-use unit. Alternatively, the adapter assembly 865 can be packaged and sold as a separate unit to be connected to the cannula body 851 at the point of use. The adapter assembly 865 has a Y-fitting 858 which is connected to the proximal end 852 of the cannula body 851. The Y-fitting 858 has a first branch ending in a barbed connector 859 which is configured for fluid connection to tubing 892 from a cardiopulmonary bypass system, as shown in FIG. 34. To prepare the arterial bypass cannula 850 for insertion into a peripheral artery, such as a patient's femoral artery or brachial artery, by an arterial cutdown or by a percutaneous Seldinger technique, a connector plug 871, which is molded of a soft, elastomeric material, is placed over the barbed connector 859. A tapered dilator 867 is passed through a wiper-type hemostasis seal 872 in the connector plug 871. The wiper-type hemostasis seal 872 is a hole through the elastomeric connector plug 871 that has a slight interference fit with the external diameter of the dilator 867. A series of ridges can be molded within the hemostasis seal 872 to reduce the sliding friction on the dilator 867 while maintaining a hemostatic seal. The dilator 867 has a tapered distal tip 869, a proximal hub 870 with a luer lock connector, and a guidewire lumen, sized for an 0.038 inch diameter guidewire, that runs from the distal tip 869 to the proximal hub 870. The diameter of the dilator 867 is such that the dilator 867 substantially fills the cannula lumen 857 at the distal end 853 of the cannula body 851. The length of the dilator 867 is such that the distal tip 869 of the dilator 867 extends approximately 4 to 5 cm beyond the beveled end 853 of the cannula body 851 when the dilator hub 870 is against the connector plug 870. The dilator 867 may assume a bend 873 in it at the point where the dilator 867 passes through the Y-fitting 858 when the dilator 867 is fully inserted. One or more depth markers 874, 875 can be printed on the dilator 867 with a nontoxic, biocompatible ink. One depth marker 874 may be placed so that, when the marker 874 is just proximal to the hemostasis seal 872 on the elastomeric connector plug 871, the tapered distal tip 869 of the dilator 867 is just emerging from the beveled end 853 of the cannula body 851. In one particular embodiment, the tapered dilator 867 is made of extruded polyurethane with a radiopaque filler so that the position of the dilator can be verified fluoroscopically.

A second branch of the Y-fitting 858 is connected to an extension tube 862 which terminates in a hemostasis valve 876 configured to receive the endoaortic partitioning catheter 895 therethrough. The extension tube 862 has a flexible middle section which serves as a proximal clamp site 864 that can be clamped with an external clamp, such as a Vorse type tube occluding clamp, forming a hemostatic seal to temporarily stop blood flow through the lumen 863 of the extension tube 862. The lumen 863 of the extension tube 862 between the proximal clamp site 864 and the hemostasis valve 876 serves as a catheter insertion chamber 866, the function of which will be more fully explained in connection with FIG. 33.

In a preferred embodiment of the arterial bypass cannula 850, the hemostasis valve 876 is a type of compression fitting known in the industry as a Tuohy-Borst adapter. The Tuohy-Borst adapter 876 is shown in greater detail in FIG. 32. The Tuohy-Borst adapter 876 has a compressible tubular or ring-shaped elastomeric seal 883 that fits within a counterbore 879 in the fitting body 877. The elastomeric seal 883 is preferably made from a soft, resilient, self-lubricating elastomeric material, such as silicone rubber having a hardness of approximately 20–25 Shore A durometer. The elastomeric seal 883 has a central passage 884 with a beveled entry 885 on the proximal end of the passage 884. The elastomeric seal 883 has a beveled distal surface 886 angled at about 45° which fits against a tapered seat 880 in the bottom of the counterbore 879 that is angled at about 60°. A threaded compression cap 887 screws onto the fitting body 877. The threaded cap 887 has a tubular extension 887 which fits within the counterbore 879 in the fitting body 877. An externally threaded section 888 on the proximal end of the tubular extension 887 engages an internally threaded section 881 within the proximal end of the counterbore 879. When the threaded cap 887 is screwed down onto the fitting body 877, the tubular extension 889 bears on the elastomeric seal 883 forcing it against the tapered seat 880 of the counterbore 879. The resultant force on the elastomeric seal 883 squeezes the elastomeric seal 883 inward to close off the passage central 884 to make a hemostatic seal. When the threaded cap 887 is unscrewed again from the fitting body 877, the central passage 884 of the elastomeric seal 883 opens up again. The deliberate 15° mismatch between the angle of the beveled distal surface 886 of the elastomeric seal 883 and the tapered seat 880 of the counterbore 879 prevents the elastomeric seal 883 from binding and causes the central passage 884 to open up reliably when the threaded cap 887 is unscrewed from the fitting body 887. An internal ridge 890 within the threaded cap 887 engages in a snap fit with an external ridge 882 on the proximal end of the fitting body 877 to keep the threaded cap 887 from being inadvertently separated from the fitting body 877 if the threaded cap 887 is unscrewed to the point where the threads 888, 881 are no longer engaged.

In one particular embodiment, the central passage 884 of the elastomeric seal 883 has an internal diameter of about 5 mm to allow clearance for inserting a catheter 895 with a shaft diameter of 3–4 mm through the Tuohy-Borst adapter 876 without damaging the occlusion balloon 896 mounted on it. The Tuohy-Borst adapter 876 is adjustable through a range of positions, including a fully open position for inserting the balloon catheter 896, a partially closed position for creating a sliding hemostatic seal against the shaft 897 of the catheter 895, and a completely closed position for creating a hemostatic seal with no catheter in the central passage 884. In an alternative embodiment, the central passage 884 of the elastomeric seal 883 can be sized to have a slight interference fit with the shaft 897 of the catheter 895 when uncompressed. In this embodiment, the Tuohy-Borst adapter 876 has positions which include a fully open position for creating a sliding hemostatic seal against the shaft 897 of the catheter 895, and a completely closed position for creating a hemostatic seal with no catheter in the central passage 884. In a second alternative embodiment, a separate ring-like wiper seal (not shown) is added in series with the Tuohy-Borst adapter 876 to create a passive sliding hemostatic seal against the shaft 897 of the catheter 895 without the necessity of tightening the threaded cap 887. Additionally, the Tuohy-Borst adapter 876, in either embodiment, may have a tightly closed position for securing the catheter shaft 897 with respect to the patient. In other alternative embodiments, other known hemostasis valves may be substituted for the Tuohy-Borst adapter 876 as just described.

In a particularly preferred embodiment, the internal surface of the lumen 863 of the extension tube 862 and/or the internal surface of the lumen 857 of the cannula body 851 are coated with a highly lubricious biocompatible coating, such as polyvinyl pyrrolidone, to ease the passage of the endoaortic partitioning catheter 895, and especially the occlusion balloon 896, through these lumens. Other commercially available lubricious biocompatible coatings can also be used, such as Photo-Link™ coating available from BSI Surface Modification Services of Eden Prairie, Minn.; sodium hyaluronate coating available from Biocoat of Fort Washington, Pa.; and proprietary silicone coatings available from TUA of Sarasota, Fla. Similarly, a distal portion of the exterior of the cannula body 851 can be coated with one of these lubricious biocompatible coatings to facilitate insertion of the arterial bypass cannula 850 into the artery at the cannulation site. Furthermore, the endoaortic partitioning catheter 895 itself, in any of the embodiments described herein, can be coated with one of these lubricious biocompatible coatings to facilitate its insertion and passage through the arterial bypass cannula 850 and the patient's vasculature. Preferably, the occlusion balloon 896 of the endoaortic partitioning catheter 895 should be free of any lubricious coating so that there is sufficient friction between the expanded occlusion balloon and the interior aortic wall to prevent accidental dislodgement or migration of the occlusion balloon 896.

Figure 33:
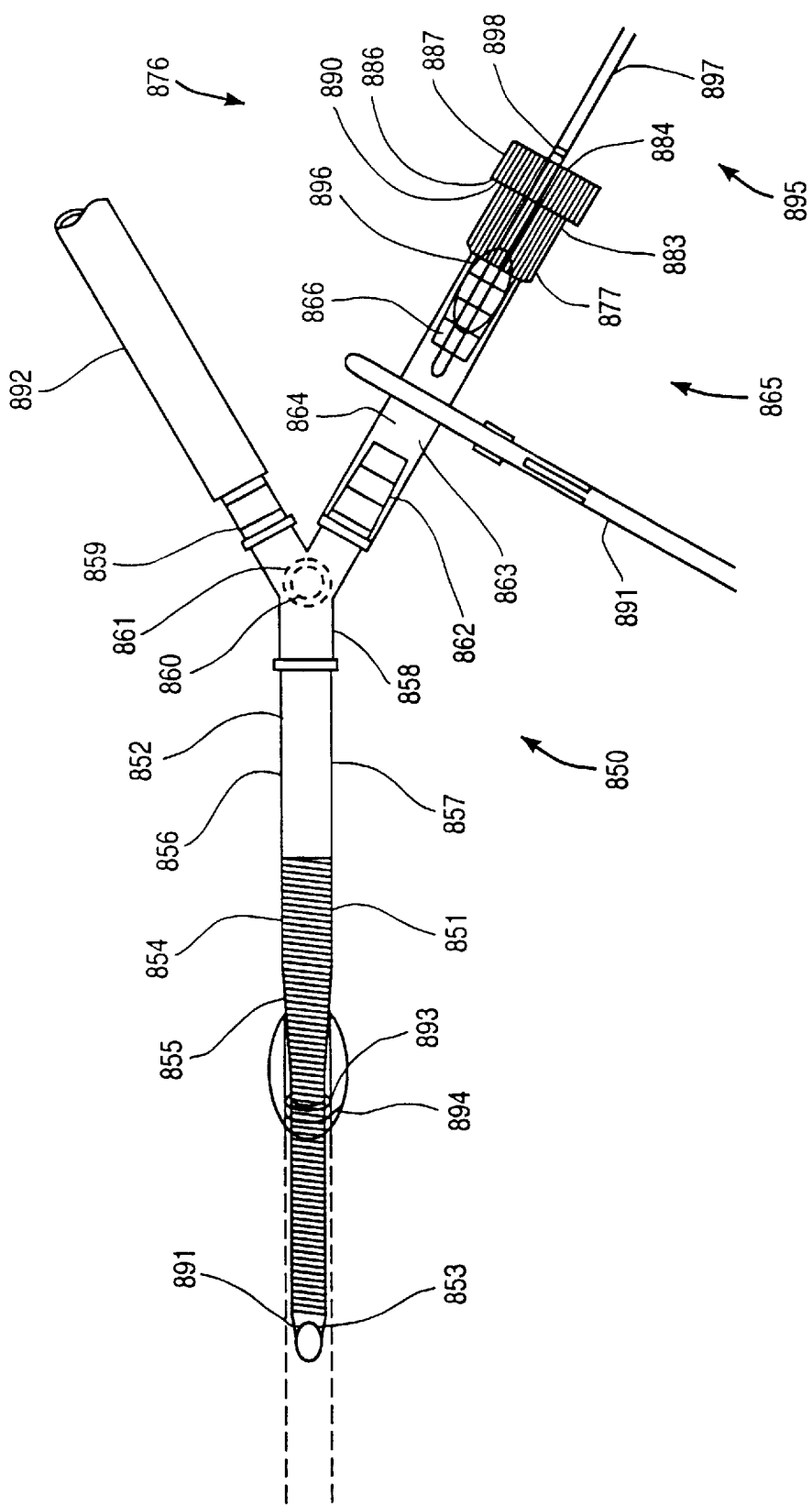
FIG. 33 illustrates the cannula of FIG. 31 with an endoaortic partitioning catheter introduced into the catheter insertion chamber.

In operation, the arterial bypass cannula 850 is prepared for insertion as shown in FIG. 26, with the tapered dilator 867 in place in the blood flow lumen 857 of the cannula body 851 and with the Tuohy-Borst fitting 876 completely closed. An arterial cutdown is made into an artery, preferably the patient's femoral artery, at the cannulation site or a guidewire is placed percutaneously using the Seldinger technique and the dilator 867 and the distal end 853 of the cannula body 851 are inserted into the lumen of the artery with the bevel up. A suture 894 can be tied around the artery 893 where the cannula body 851, as shown in FIG. 33, inserts to avoid bleeding from the artery 893 at the cannulation site. The dilator 867 is then withdrawn from the cannula body 851, allowing blood to flash back and fill the lumen 857 of the cannula body 851. When the tip 868 of the dilator 867 is proximal to the distal clamp site 856 an external clamp is applied to the distal clamp site 856 to stop further blood flow. The dilator 867 is completely withdrawn and the connector plug 871 is removed so that a tube 892 from the cardiopulmonary bypass system can be attached to the barbed connector 859 of the Y-fitting 858, as shown in FIG. 33. Air is bled from the arterial bypass cannula 850 by elevating the extension tube 862 and opening the Tuohy-Borst fitting 876 slightly and releasing the external on the distal clamp site 856 to allow the blood to flow out through the Tuohy-Borst fitting 876. Alternatively, air can be bled out of the arterial bypass cannula 850, through an optional vent fitting with a luer cap (not shown) that can be provided on the Y-fitting 858. The optional vent fitting can be also used as a port for monitoring perfusion pressure within the arterial bypass cannula 850. Once the air is bled out of the system, the external clamp can be removed from the distal clamp site 856 the cardiopulmonary bypass system pump can be turned on to perfuse the patient's arterial system with oxygenated blood at a rate of about 3 to 6 liters/minute, preferably at a pump pressure of less than about 500 mmHg.

To introduce the endoaortic partitioning catheter 895 into the arterial bypass cannula 850, an external clamp 891 is placed on the proximal clamp site 864, as shown in FIG. 33, to stop blood from flowing out through the extension tube 862 and the Tuohy-Borst adapter 876 is opened all the way by unscrewing the threaded cap 887 to open up the passage 884 through the elastomeric seal 883.

The distal end of the endoaortic partitioning catheter 895 with the occlusion balloon 896 mounted thereon is inserted through the passage 884 of the Tuohy-Borst adapter 876 into the insertion chamber 866 of the arterial bypass cannula 850. Optionally, first and second depth markers 898, 899 may be printed on the shaft 897 of the endoaortic partitioning catheter 895 with a nontoxic, biocompatible ink. The first depth marker 898 on the catheter 895 indicates when the occlusion balloon 896 is entirely distal to the elastomeric seal 883. When the first depth marker 898 is positioned just proximal to the threaded cap 887, the Tuohy-Borst adapter 876 should be tightened to create a sliding, hemostatic seal around the catheter shaft 897. Now, the clamp 891 can be removed to allow the catheter 895 to be advanced distally through the arterial bypass cannula 850.

Before the endoaortic partitioning catheter 895 enters the blood flow lumen 857 within the Y-fitting 858, the perfusion rate from the cardiopulmonary bypass system pump should be temporarily turned down to a rate of about 1 to 2 liters/minute to avoid hemolysis, tubing disruptions or other complications due to the additional flow resistance caused by the occlusion balloon 896 as it passes through the blood flow lumen 857. The catheter 895 can now be advanced distally until the occlusion balloon 986 is distal to the distal end 853 of the cannula body 851. A second depth marker 899 on the catheter 895 indicates when the occlusion balloon 896 is entirely distal to the distal end 853 of the cannula body 851. When the second depth marker 898 reaches the proximal end of the threaded cap 887, as shown in FIG. 34, the perfusion rate from the cardiopulmonary bypass system pump should be returned to a rate of about 3 to 6 liters/minute. The endoaortic partitioning catheter 895 can now be advanced into the ascending aorta for partitioning the heart and inducing cardioplegic arrest according to the methods described above. When the endoaortic partitioning catheter 895 is in position within the ascending aorta the Tuohy-Borst adapter 876 can be tightened around the catheter 895 to act as a friction lock to hold the catheter in place.

After completion of the surgical procedure on the heart, the endoaortic partitioning catheter 895 can be removed from the arterial bypass cannula 850 by reversing the sequence of operations described above. The arterial bypass cannula 850 can remain in place until the patient has been weaned from cardiopulmonary bypass, then the arterial bypass cannula 850 can be removed and the arterial puncture site repaired.

It should be noted that for the venous side of the cardiopulmonary bypass system, a similar dual purpose venous bypass cannula and introducer sheath with the above-described features can be used for accessing the femoral vein and for introducing a venting catheter or other devices into the venous side of the circulatory system. In a venous configuration the dual purpose venous bypass cannula and introducer sheath preferably has an external diameter of about 21 to 32 French units, an internal diameter of about 19 to 30 French units, and a length of about 50 to 75 cm.

FIGS. 35A–35C illustrate another means of steering the distal tip 171 of the endoaortic partitioning catheter 170 for centering the catheter tip within the ascending aorta B. The endoaortic partitioning catheter 170 is shown positioned within the patient's aortic arch A in FIG. 35A. The distal tip 171 of the catheter 170 is made steerable by a multichamber occlusion balloon 172 mounted on the distal portion 173 of the catheter which is shown partially cut away in FIG. 35A. The distal portion 173 of the catheter 170 has a distal curve which may be a 180°±45° arc or a 270°±45° arc, as described in previous embodiments. The multichamber occlusion balloon 172 has a first chamber 174 and a second chamber 175. The balloon 172 is mounted so that the first chamber 174 is oriented toward the outside of the distal curve and the second chamber 175 is oriented toward the inside of the distal curve. A first inflation lumen 176 in the catheter 170 connects to the first chamber 174 through a first inflation port 178. A second inflation lumen 177 in the catheter 170 connects to the second chamber 175 through a second inflation port 179. An infusion lumen 181 connects with one or more infusion ports 182 at the distal tip 171 of the catheter 170.

As shown in the cross section of the deflated occlusion balloon 172 in FIG. 35B, a partition wall 180 separates the first 174 and second 175 chambers of the balloon 172. The first 174 and second 175 chambers of the balloon 172 may be differentially inflated through the inflation lumens 176, 177. For example, the cross section of FIG. 35C shows the first chamber 174 of the multichamber occlusion lumen 172 inflated to a greater degree than the second chamber 175. Because the first chamber 174 is oriented toward the outside of the distal curve of the catheter 170, the distal tip 171 of the catheter 170 is forced toward the inside of the aortic arch A, that is, toward the left side of the patient, as in FIG. 35A. Alternatively, the second chamber 175 can be inflated to a greater degree than the first chamber 174 to force the distal tip 171 of the catheter 170 toward the outside of the aortic arch A, that is, toward the right side of the patient. Thus, the distal tip 171 of the catheter 170 can be steered to center the tip 171 within the lumen of the ascending aorta B under fluoroscopic observation by inflating and deflating the individual chambers of the multichamber occlusion balloon 172. It should be noted that the multichamber occlusion balloon 172 is not limited to only two chambers. The multichamber occlusion balloon 172 can be made with three, four or more chambers to give the distal tip 171 greater degrees of steerability.

Figure 36:
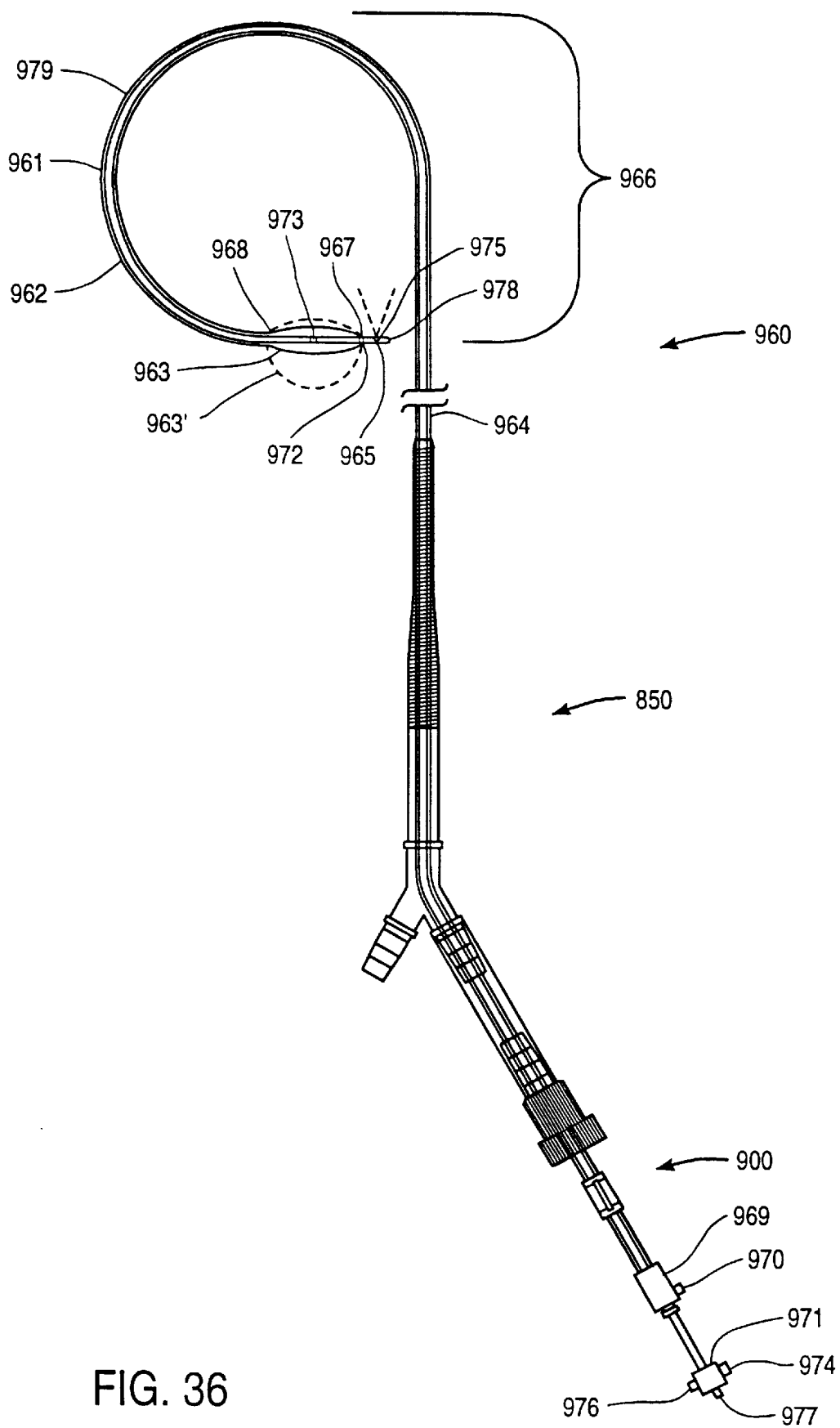
FIG. 36 illustrates a multifunction embodiment of the endoaortic partitioning catheter combined with a dual function arterial cannula and introducer sheath and a frictional locking suture ring.

It should be noted that while several aspects of the present invention have been illustrated and discussed separately in the foregoing description, many of these aspects can be advantageously combined into a single, multifunction embodiment. As an illustrative example, FIG. 36 shows a multifunction embodiment of the endoaortic partitioning catheter 960 combining several of the inventive aspects previously discussed. The shaft 964 of the catheter 960 has a coaxial construction with an inner 961 and outer 962 tubular member, similar to the embodiments described in connection with FIGS. 5A–5D and 6A–6D. The catheter shaft 964 may be made with varying degrees of stiffness along the length of the shaft 964, culminating in a soft atraumatic tip 965 which may be highly loaded with a radiopaque filler. The catheter shaft 964 may be made with a precurved distal portion 966 similar to FIGS. 10A–10B, or with a precurved distal portion 966 which is out of plane with the proximal portion of the catheter shaft 964, as in FIGS. 11A–11B. An expandable occlusion balloon 963 is mounted on the distal portion 966 of the catheter shaft 964. The occlusion balloon 963 preferably has a low profile deflated state with an ellipsoidal shape, similar to that shown in FIG. 6A. In addition, the occlusion balloon 963 may have an eccentric or asymmetrical inflated profile 963', similar to any of the embodiments discussed in relation to FIGS. 14–26, or FIG. 35 which would also provide a steering means for the distal tip of the catheter, as would the steering mechanism of FIG. 27.

The occlusion balloon 963 is mounted with its distal balloon neck 967 attached to the inner tubular member 961 and its proximal balloon neck attached to the outer tubular member 962. The inner tubular member 961 is attached at its proximal end to a first hub 971 and the outer tubular member 962 is attached at its proximal end to a second 969 hub 971 which are axially slidably and/or rotatable with respect to one another, similar to the embodiments described in relation to FIGS. 8A–8D and 9A–9B. An infusion fitting 977, such as a luer lock, on the first hub 971 is connected to an infusion lumen 978 which terminates at the distal end of the catheter 960. An inflation fitting 970, preferably a luer lock, on the second hub 971 is connected to an inflation lumen 979 defined by an annular space between the inner 961 and outer 962 tubular members which communicates with the interior of the occlusion balloon 963.

The second hub 969 may be moved proximal and/or rotated with respect to the first hub 971 to minimize the deflated profile of the occlusion balloon 963. The lower deflated profile of the occlusion balloon 963 facilitates easy insertion of the catheter 960 through a dual function arterial cannula and introducer sheath 850, similar to that described in relation to FIGS. 31–34. When the endoaortic partitioning catheter 960 is combined with the dual function arterial cannula and introducer sheath 850, the shaft 964 of the catheter 960 should be made with an additional 20–25 cm of length for a total shaft length of approximately 100–115 cm. The diameter of the catheter shaft 964 should also be minimized as much as possible to reduce the amount of cross sectional area the catheter shaft 964 takes up in the blood flow lumen of the arterial cannula 850. To this end, this combined embodiment is made with a distal pressure transducer 972 and a balloon pressure monitoring transducer 973 mounted on the inner tubular member 961, as described in relation to FIGS. 7A–7C. The distal pressure transducer 972 and the balloon pressure monitoring transducer 973 are electrically connected to an electrical connector 974 on the first hub 971. Also on the first hub 971 is a fiberoptic connector 976 which connects to a fiberoptic bundle 975 which terminates with a means for directing a lateral beam of light at the distal end of the catheter 960 for aortic transillumination and/or for facilitating nonfluoroscopic placement of the catheter 960. The fiberoptic bundle 975 may also be made as a separate unit for insertion through the infusion lumen 978 of the catheter 960 to further reduce the catheter shaft diameter while maintaining maximum functionality. The diameter of the catheter shaft 964 can thus be reduced to as small as 8 to 10.5 French (2.7–3.5 mm diameter).

Additionally the endoaortic partitioning catheter 960 may be combined with a frictional locking suture ring 900 for anchoring the catheter 960 in the proper position after placement, as described in relation to FIGS. 30A–30B.

Thus, it can be seen that the methods and devices described herein provide a system for partitioning a patient's heart and coronary arteries from the remainder of the arterial system by occluding the ascending aorta between the coronary ostia and the brachiocephalic artery, for inducing cardioplegic arrest and for maintaining the patient on cardiopulmonary bypass entirely through minimally invasive transluminal access. While the above is a complete description of the presently preferred embodiments of the invention, various alternatives, modifications and equivalents may be used. Therefore, the above description should not be taken as limiting the scope of the invention, which is defined by the appended claims.

What is claimed is:

1. An aortic occlusion catheter, comprising:

a shaft having a first lumen; and means for occluding a patient's ascending aorta between the coronary ostia movable from an expanded shape to a collapsed shape, the occluding means also being shaped such that it can be seated across the opening to the brachiocephalic artery while permitting blood flow into the brachiocephalic artery;

the first lumen having an outlet positioned distal to the occluding means and having a size sufficient to deliver cardioplegic fluid to the patient's heart at a rate sufficient to arrest the patient's heart.

2. The catheter of claim 1, wherein:

the occluding means has a flow path therethrough for permitting the flow of blood to the brachiocephalic artery when the occluding means is in the expanded shape and positioned in the patient's ascending aorta.

3. The catheter of claim 1, wherein:

the occluding means is shaped such that it can be seated across the opening to the patient's carotid artery.

4. The catheter of claim 1, further comprising:

a source of cardioplegic fluid coupled to the first lumen.

* * * * *